United States Patent
Went et al.

(10) Patent No.: US 10,646,456 B2
(45) Date of Patent: *May 12, 2020

(54) METHODS OF ADMINISTERING AMANTADINE

(71) Applicant: Adamas Pharma, LLC, Emeryville, CA (US)

(72) Inventors: Gregory T. Went, Mill Valley, CA (US); Timothy J. Fultz, Jasper, GA (US); Natalie McClure, Portola Valley, CA (US)

(73) Assignee: Adamas Pharma, LLC, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,770

(22) Filed: Nov. 13, 2018

(65) Prior Publication Data

US 2019/0307707 A1    Oct. 10, 2019

Related U.S. Application Data

(63) Continuation of application No. 14/307,195, filed on Jun. 17, 2014, now Pat. No. 10,154,971.

(60) Provisional application No. 61/836,082, filed on Jun. 17, 2013.

(51) Int. Cl.
    *A61K 31/13*      (2006.01)
    *A61K 9/50*      (2006.01)
    *A61K 9/16*      (2006.01)

(52) U.S. Cl.
    CPC ............ *A61K 31/13* (2013.01); *A61K 9/5078* (2013.01); *A61K 9/1652* (2013.01); *A61K 9/5026* (2013.01); *A61K 9/5047* (2013.01)

(58) Field of Classification Search
    CPC .... A61K 31/13; A61K 9/1652; A61K 9/5026; A61K 9/5047; A61K 9/5078
    See application file for complete search history.

(56) References Cited

U.S. PATENT DOCUMENTS

| | | |
|---|---|---|
| 3,152,180 A | 10/1964 | Haaf |
| 3,391,142 A | 7/1968 | Mills et al. |
| 3,992,518 A | 11/1976 | Chien et al. |
| 4,122,193 A | 10/1978 | Scherm et al. |
| 4,148,896 A | 4/1979 | Smith, Jr. et al. |
| 4,273,774 A | 6/1981 | Scherm |
| 4,284,444 A | 8/1981 | Bernstein et al. |
| 4,346,112 A | 8/1982 | Henkel et al. |
| 4,606,909 A | 8/1986 | Bechgaard et al. |
| 4,767,628 A | 8/1988 | Hutchinson |
| 4,769,027 A | 9/1988 | Baker et al. |
| 4,812,481 A | 3/1989 | Reischig et al. |
| 4,828,836 A | 5/1989 | Elger et al. |
| 4,839,177 A | 6/1989 | Colombo et al. |
| 4,897,268 A | 1/1990 | Tice et al. |
| 5,057,321 A | 10/1991 | Edgren et al. |
| 5,061,703 A | 10/1991 | Bormann et al. |
| 5,086,072 A | 2/1992 | Trullas et al. |
| 5,186,938 A | 2/1993 | Sablotsky et al. |
| 5,190,763 A | 3/1993 | Edgren et al. |
| 5,192,550 A | 3/1993 | Edgren et al. |
| 5,213,808 A | 5/1993 | Bar-Shalom et al. |
| 5,221,536 A | 6/1993 | Edgren et al. |
| 5,330,766 A | 7/1994 | Morella et al. |
| 5,334,618 A | 8/1994 | Lipton |
| 5,358,721 A | 10/1994 | Guittard et al. |
| 5,366,738 A | 11/1994 | Rork et al. |
| 5,378,474 A | 1/1995 | Morella et al. |
| 5,382,601 A | 1/1995 | Nuernberg et al. |
| 5,395,626 A | 3/1995 | Kotwal et al. |
| 5,422,120 A | 6/1995 | Kim |
| 5,422,123 A | 6/1995 | Conte et al. |
| 5,576,022 A | 11/1996 | Yang et al. |
| 5,601,845 A | 2/1997 | Buxton et al. |
| 5,614,560 A | 3/1997 | Lipton |
| 5,660,848 A | 8/1997 | Moo-Young |
| 5,756,115 A | 5/1998 | Moo-Young et al. |
| 5,849,800 A | 12/1998 | Smith |
| 5,891,885 A | 4/1999 | Caruso |
| 5,912,013 A | 6/1999 | Rudnic et al. |
| 5,919,826 A | 7/1999 | Caruso |
| 6,046,232 A | 4/2000 | Kelleher et al. |
| 6,057,364 A | 5/2000 | Jasys et al. |
| 6,066,652 A | 5/2000 | Zenner et al. |
| 6,110,498 A | 8/2000 | Rudnic et al. |

(Continued)

FOREIGN PATENT DOCUMENTS

| | | |
|---|---|---|
| AU | 2002323873 B2 | 11/2006 |
| CA | 2323805 A1 | 9/1999 |

(Continued)

OTHER PUBLICATIONS

Adamas Pharmaceuticals (Jun. 10, 2013). "Adamas Pharmaceuticals to report positive phase 2/3 results for ADS-5102 for the treatment of Levodopa-induced Dyskinesia in Parkinson's disease," Located at http://ir.adamaspharma.com/releasedetail.cfm?releaseid=837891, 2 total pages.

Ahlskog, J.E. et al. (2001). "Frequency of levodopa-related dyskinesias and motor fluctuations as estimated from the cumulative literature," Mov Disord. 16:448-458.

Alisky et al., A case history illustrating how extended release cholinesterase inhibitors could improve management of Alzheimer's disease. J. Alzheimer's Dis. Dec. 2003, 5(6):477-78.

(Continued)

*Primary Examiner* — Sarah Pihonak
(74) *Attorney, Agent, or Firm* — Cooley LLP

(57) ABSTRACT

Methods of nighttime administration of amantadine to reduce sleep disturbances in patient undergoing treatment with amantadine are described, as well as compositions of extended release amantadine that are suitable for nighttime administration.

58 Claims, 9 Drawing Sheets

(56) References Cited

U.S. PATENT DOCUMENTS

| | | |
|---|---|---|
| 6,114,392 A | 9/2000 | Gilad et al. |
| 6,183,770 B1 | 2/2001 | Muchin et al. |
| 6,187,338 B1 | 2/2001 | Caruso et al. |
| 6,194,000 B1 | 2/2001 | Smith et al. |
| 6,217,905 B1 | 4/2001 | Edgren et al. |
| 6,251,430 B1 | 6/2001 | Zhang et al. |
| 6,284,276 B1 | 9/2001 | Rudnic et al. |
| 6,290,990 B1 | 9/2001 | Grabowski et al. |
| 6,372,255 B1 | 4/2002 | Saslawski et al. |
| 6,384,083 B1 | 5/2002 | Ludwig et al. |
| 6,392,104 B1 | 5/2002 | Ishii et al. |
| 6,444,702 B1 | 9/2002 | Wang et al. |
| 6,479,553 B1 | 11/2002 | McCarthy |
| 6,491,949 B2 | 12/2002 | Faour et al. |
| 6,569,463 B2 | 5/2003 | Patel et al. |
| 6,620,845 B2 | 9/2003 | Wang et al. |
| 6,635,268 B2 | 10/2003 | Peery et al. |
| 6,715,485 B1 | 4/2004 | Djupesland |
| 6,717,012 B2 | 4/2004 | Wang et al. |
| 6,743,211 B1 | 6/2004 | Prausnitz et al. |
| 6,746,689 B2 | 6/2004 | Fischer et al. |
| 6,753,011 B2 | 6/2004 | Faour |
| 6,764,697 B1 | 7/2004 | Jao et al. |
| 6,852,889 B2 | 2/2005 | Wang et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 6,945,952 B2 | 9/2005 | Kwon |
| 6,962,717 B1 | 11/2005 | Huber et al. |
| 7,211,275 B2 | 5/2007 | Ying et al. |
| 7,619,007 B2 | 11/2009 | Went et al. |
| 7,718,677 B2 | 5/2010 | Quik et al. |
| 7,858,660 B2 | 12/2010 | Nguyen et al. |
| 7,981,930 B2 | 7/2011 | Nguyen et al. |
| 8,039,009 B2 | 10/2011 | Rastogi et al. |
| 8,058,291 B2 | 11/2011 | Went et al. |
| 8,168,209 B2 | 5/2012 | Went et al. |
| 8,173,708 B2 | 5/2012 | Went et al. |
| 8,252,331 B2 | 8/2012 | Meyer et al. |
| 8,263,125 B2 | 9/2012 | Vaya et al. |
| 8,268,352 B2 | 9/2012 | Vaya et al. |
| 8,283,379 B2 | 10/2012 | Went et al. |
| 8,293,794 B2 | 10/2012 | Went et al. |
| 8,313,770 B2 | 11/2012 | Pathak et al. |
| 8,329,752 B2 | 12/2012 | Went et al. |
| 8,338,485 B2 | 12/2012 | Went et al. |
| 8,338,486 B2 | 12/2012 | Went et al. |
| 8,357,397 B2 | 1/2013 | Bouwstra et al. |
| 8,362,085 B2 | 1/2013 | Went et al. |
| 8,389,008 B2 | 3/2013 | Baichwal et al. |
| 8,389,578 B2 | 3/2013 | Went et al. |
| 8,426,472 B2 | 4/2013 | Went et al. |
| 8,574,626 B2 | 11/2013 | Vergez et al. |
| 8,580,858 B2 | 11/2013 | Went et al. |
| 8,591,947 B2 | 11/2013 | Vergez et al. |
| 8,598,233 B2 | 12/2013 | Went et al. |
| 8,637,080 B2 | 1/2014 | Pastini et al. |
| 8,741,343 B2 | 6/2014 | Went et al. |
| 8,796,337 B2 | 8/2014 | Went et al. |
| 8,821,928 B2 | 9/2014 | Hemmingsen et al. |
| 8,889,740 B1 | 11/2014 | Went et al. |
| 8,895,614 B2 | 11/2014 | Went et al. |
| 8,895,615 B1 | 11/2014 | Went et al. |
| 8,895,616 B1 | 11/2014 | Went et al. |
| 8,895,617 B1 | 11/2014 | Went et al. |
| 8,895,618 B1 | 11/2014 | Went et al. |
| 8,920,837 B2 | 12/2014 | Pilgaonkar et al. |
| 8,987,333 B2 | 3/2015 | Went et al. |
| 9,072,697 B2 | 7/2015 | Went et al. |
| 9,867,791 B2 | 1/2018 | Went et al. |
| 9,867,792 B2 | 1/2018 | Went et al. |
| 9,867,793 B2 | 1/2018 | Went et al. |
| 9,877,933 B2 | 1/2018 | Went et al. |
| 10,154,971 B2 | 12/2018 | Went et al. |
| 2001/0031278 A1 | 10/2001 | Oshlack et al. |
| 2002/0071863 A1 | 6/2002 | Dong et al. |
| 2003/0045577 A1 | 3/2003 | Madhat |
| 2003/0082230 A1 | 5/2003 | Baichwal et al. |
| 2003/0158154 A1 | 8/2003 | Fleshner-Barak |
| 2003/0170302 A1 | 9/2003 | Seth et al. |
| 2003/0203055 A1 | 10/2003 | Rao et al. |
| 2004/0087658 A1 | 5/2004 | Moebius |
| 2004/0097484 A1 | 5/2004 | Cantillion et al. |
| 2004/0102525 A1 | 5/2004 | Kozachuk |
| 2004/0106681 A1 | 6/2004 | Rao et al. |
| 2004/0122090 A1 | 6/2004 | Lipton |
| 2004/0185097 A1 | 9/2004 | Kannan et al. |
| 2004/0224020 A1 | 11/2004 | Schoenhard |
| 2005/0031651 A1 | 2/2005 | Gervais et al. |
| 2005/0065219 A1 | 3/2005 | Lipton et al. |
| 2005/0119249 A1 | 6/2005 | Buntinx |
| 2005/0124701 A1 | 6/2005 | Went et al. |
| 2005/0153953 A1 | 7/2005 | Trippodi-Murphy et al. |
| 2005/0191349 A1 | 9/2005 | Boehm et al. |
| 2005/0202088 A1 | 9/2005 | Hanshermann et al. |
| 2005/0208132 A1 | 9/2005 | Sathyan et al. |
| 2005/0209218 A1 | 9/2005 | Meyerson et al. |
| 2005/0232990 A1 | 10/2005 | Boehm et al. |
| 2005/0245460 A1 | 11/2005 | Meyerson et al. |
| 2005/0245617 A1 | 11/2005 | Meyerson et al. |
| 2005/0267176 A1 | 12/2005 | Barberich |
| 2005/0271708 A1 | 12/2005 | Thombre |
| 2006/0008527 A1 | 1/2006 | Lagoviyer et al. |
| 2006/0051416 A1 | 3/2006 | Rastogi et al. |
| 2006/0052370 A1 | 3/2006 | Meyerson et al. |
| 2006/0062851 A1 | 3/2006 | Vergez et al. |
| 2006/0063810 A1 | 3/2006 | Vergez et al. |
| 2006/0142398 A1 | 6/2006 | Went et al. |
| 2006/0159763 A1 | 7/2006 | Meyer et al. |
| 2006/0189694 A1 | 8/2006 | Went et al. |
| 2006/0240043 A1 | 10/2006 | Meyerson et al. |
| 2006/0251717 A1 | 11/2006 | Firestone et al. |
| 2006/0252788 A1 | 11/2006 | Went et al. |
| 2007/0036843 A1 | 2/2007 | Hirsh et al. |
| 2007/0104778 A1 | 5/2007 | Zeng et al. |
| 2007/0184112 A1 | 8/2007 | Wong et al. |
| 2007/0270443 A1 | 11/2007 | Went et al. |
| 2008/0057123 A1 | 3/2008 | Grenier et al. |
| 2008/0089861 A1 | 4/2008 | Went et al. |
| 2008/0227743 A1 | 9/2008 | Nguyen et al. |
| 2008/0248107 A1 | 10/2008 | Pilgaonkar et al. |
| 2008/0260825 A1 | 10/2008 | Quick et al. |
| 2008/0274061 A1 | 11/2008 | Schollmayer et al. |
| 2008/0279819 A1 | 11/2008 | Went et al. |
| 2009/0041820 A1 | 2/2009 | Wu et al. |
| 2009/0169587 A1 | 7/2009 | Baichwal et al. |
| 2009/0196908 A1 | 8/2009 | Lee et al. |
| 2009/0220613 A1 | 9/2009 | Odidi et al. |
| 2009/0247481 A1 | 10/2009 | Nguyen et al. |
| 2010/0004251 A1 | 1/2010 | Barberich |
| 2010/0029723 A1 | 2/2010 | Quick et al. |
| 2010/0047342 A1 | 2/2010 | Went et al. |
| 2010/0092554 A1 | 4/2010 | Reess et al. |
| 2010/0092562 A1 | 4/2010 | Hollenbeck et al. |
| 2010/0137448 A1 | 6/2010 | Lipton et al. |
| 2010/0158895 A1 | 6/2010 | Quik et al. |
| 2010/0159001 A1 | 6/2010 | Cardinal et al. |
| 2010/0166735 A1 | 7/2010 | Quik et al. |
| 2010/0196463 A1 | 8/2010 | Quik et al. |
| 2010/0221324 A1 | 9/2010 | Petereit et al. |
| 2010/0221328 A1 | 9/2010 | Wertz et al. |
| 2010/0239635 A1 | 9/2010 | McClain et al. |
| 2010/0260838 A1 | 10/2010 | Went et al. |
| 2010/0266684 A1 | 10/2010 | Went et al. |
| 2010/0311697 A1 | 12/2010 | Went et al. |
| 2011/0053981 A1 | 3/2011 | Ieni et al. |
| 2011/0059169 A1 | 3/2011 | Went et al. |
| 2011/0064804 A1 | 3/2011 | Went et al. |
| 2011/0077276 A1 | 3/2011 | Quik et al. |
| 2011/0142905 A1 | 6/2011 | Bar-Shalom et al. |
| 2011/0189273 A1 | 8/2011 | Went et al. |
| 2011/0230432 A1 | 9/2011 | Nguyen et al. |
| 2011/0287094 A1 | 11/2011 | Penhasi et al. |

(56) References Cited

U.S. PATENT DOCUMENTS

| | | |
|---|---|---|
| 2012/0045506 A1 | 2/2012 | Baer et al. |
| 2012/0045508 A9 | 2/2012 | Went et al. |
| 2012/0046365 A1 | 2/2012 | Went et al. |
| 2012/0064167 A1 | 3/2012 | Hall et al. |
| 2012/0264783 A1 | 10/2012 | Went et al. |
| 2012/0264829 A1 | 10/2012 | Went et al. |
| 2012/0264978 A1 | 10/2012 | Went et al. |
| 2012/0288560 A1 | 11/2012 | Went et al. |
| 2013/0022676 A1 | 1/2013 | Mullen et al. |
| 2013/0059008 A1 | 3/2013 | Atkinson et al. |
| 2013/0115249 A1 | 5/2013 | Vergez et al. |
| 2013/0131110 A1 | 5/2013 | Went et al. |
| 2013/0165517 A1 | 6/2013 | Went et al. |
| 2013/0165527 A1 | 6/2013 | Went et al. |
| 2013/0317115 A1 | 11/2013 | Went et al. |
| 2014/0134243 A1 | 5/2014 | Went et al. |
| 2014/0135529 A1 | 5/2014 | Went et al. |
| 2014/0179797 A1 | 6/2014 | Went et al. |
| 2014/0193490 A1 | 7/2014 | Schoenhard |
| 2014/0242163 A1 | 8/2014 | Went et al. |
| 2014/0323582 A1 | 10/2014 | Went et al. |
| 2014/0336266 A1 | 11/2014 | Went et al. |
| 2014/0343152 A1 | 11/2014 | Went et al. |
| 2014/0343153 A1 | 11/2014 | Went et al. |
| 2014/0343154 A1 | 11/2014 | Went et al. |
| 2014/0343163 A1 | 11/2014 | Went et al. |
| 2014/0343164 A1 | 11/2014 | Went et al. |
| 2014/0356425 A1 | 12/2014 | Went et al. |
| 2015/0045438 A1 | 2/2015 | Went et al. |
| 2015/0045439 A1 | 2/2015 | Went et al. |
| 2015/0045446 A1 | 2/2015 | Went et al. |
| 2015/0045447 A1 | 2/2015 | Went et al. |
| 2015/0045448 A1 | 2/2015 | Went et al. |
| 2015/0051292 A1 | 2/2015 | Went et al. |
| 2015/0057355 A1 | 2/2015 | Went et al. |
| 2015/0087721 A1 | 3/2015 | Went et al. |
| 2015/0119465 A1 | 4/2015 | Went et al. |
| 2015/0126605 A1 | 5/2015 | Went et al. |
| 2015/0126612 A1 | 5/2015 | Went et al. |
| 2015/0150991 A1 | 6/2015 | Pilgaonkar et al. |
| 2015/0157579 A1 | 6/2015 | Went et al. |
| 2015/0297537 A1 | 10/2015 | Went et al. |
| 2016/0151307 A1 | 6/2016 | Went et al. |
| 2016/0220545 A1 | 8/2016 | Went et al. |
| 2016/0243035 A1 | 8/2016 | Went et al. |
| 2016/0243058 A1 | 8/2016 | Went et al. |
| 2016/0243093 A1 | 8/2016 | Went et al. |
| 2016/0243094 A1 | 8/2016 | Went et al. |
| 2016/0243095 A1 | 8/2016 | Went et al. |
| 2016/0250149 A1 | 9/2016 | Went et al. |
| 2016/0250161 A1 | 9/2016 | Went et al. |
| 2016/0256413 A1 | 9/2016 | Went et al. |
| 2016/0256414 A1 | 9/2016 | Went et al. |
| 2016/0263052 A1 | 9/2016 | Went et al. |
| 2016/0263053 A1 | 9/2016 | Went et al. |
| 2016/0263054 A1 | 9/2016 | Went et al. |
| 2016/0263055 A1 | 9/2016 | Went et al. |
| 2016/0263056 A1 | 9/2016 | Went et al. |
| 2016/0263057 A1 | 9/2016 | Went et al. |
| 2016/0263058 A1 | 9/2016 | Went et al. |
| 2017/0056340 A1 | 3/2017 | Went et al. |
| 2017/0151185 A1 | 6/2017 | Went et al. |
| 2017/0151186 A1 | 6/2017 | Went et al. |
| 2017/0151188 A1 | 6/2017 | Went et al. |
| 2017/0151189 A1 | 6/2017 | Went et al. |
| 2018/0263914 A1 | 9/2018 | Went et al. |
| 2018/0263928 A1 | 9/2018 | Went et al. |
| 2019/0008799 A1 | 1/2019 | Went et al. |
| 2019/0262285 A1 | 8/2019 | Went et al. |

FOREIGN PATENT DOCUMENTS

| | | |
|---|---|---|
| EP | 0 392 059 A1 | 10/1990 |
| EP | 0 502 642 A1 | 9/1992 |
| EP | 0 524 968 A1 | 2/1993 |
| EP | 0 870 757 A2 | 10/1998 |
| EP | 0 927 711 A1 | 7/1999 |
| EP | 1 600 156 A2 | 11/2005 |
| EP | 1 832 298 A1 | 9/2007 |
| EP | 1 845 968 A2 | 10/2007 |
| EP | 1 509 232 B1 | 11/2008 |
| EP | 2 343 057 A1 | 7/2011 |
| EP | 2 506 709 A2 | 10/2012 |
| EP | 1 827 385 B1 | 3/2013 |
| EP | 2 623 099 A1 | 8/2013 |
| GB | 1173492 A | 12/1969 |
| JP | S-584718 A | 1/1983 |
| JP | H-10-203966 A | 8/1998 |
| JP | 2002-506047 A | 2/2002 |
| JP | 2003-523989 A | 8/2003 |
| WO | WO-89/09051 A1 | 10/1989 |
| WO | WO-91/06291 A1 | 5/1991 |
| WO | WO-91/14445 A1 | 10/1991 |
| WO | WO-94/05275 A1 | 3/1994 |
| WO | WO-95/13796 A1 | 5/1995 |
| WO | WO-97/14415 A1 | 4/1997 |
| WO | WO-98/18457 A1 | 5/1998 |
| WO | WO-99/45963 A1 | 9/1999 |
| WO | WO-00/00197 A1 | 1/2000 |
| WO | WO-00/18378 A1 | 4/2000 |
| WO | WO-01/19901 A2 | 3/2001 |
| WO | WO-01/19901 A3 | 3/2001 |
| WO | WO-01/32148 A1 | 5/2001 |
| WO | WO-01/46291 A1 | 6/2001 |
| WO | WO-01/62706 A1 | 8/2001 |
| WO | WO-02/45710 A1 | 6/2002 |
| WO | WO-03/101458 A1 | 12/2003 |
| WO | WO-2004/012700 A2 | 2/2004 |
| WO | WO-2004/012700 A3 | 2/2004 |
| WO | WO-2004/037190 A2 | 5/2004 |
| WO | WO-2004/037190 A3 | 5/2004 |
| WO | WO-2004/037234 A2 | 5/2004 |
| WO | WO-2004/037234 A3 | 5/2004 |
| WO | WO-2004/087116 A2 | 10/2004 |
| WO | WO-2004/087116 A3 | 10/2004 |
| WO | WO-2005/072705 A1 | 8/2005 |
| WO | WO-2005/079773 A2 | 9/2005 |
| WO | WO-2005/079773 A3 | 9/2005 |
| WO | WO-2006/058059 A2 | 6/2006 |
| WO | WO-2006/058059 A3 | 6/2006 |
| WO | WO-2006/058236 A2 | 6/2006 |
| WO | WO-2006/058236 A3 | 6/2006 |
| WO | WO-2006/070781 A1 | 7/2006 |
| WO | WO-2006/089494 A1 | 8/2006 |
| WO | WO-2006/121560 A2 | 11/2006 |
| WO | WO-2006/121560 A3 | 11/2006 |
| WO | WO-2007/022255 A2 | 2/2007 |
| WO | WO-2007/022255 A3 | 2/2007 |
| WO | WO-2007/136737 A1 | 11/2007 |
| WO | WO-2008/112775 A1 | 9/2008 |
| WO | WO-2011/069010 A2 | 6/2011 |
| WO | WO-2011/069010 A3 | 6/2011 |
| WO | WO-2014/204933 A1 | 12/2014 |

OTHER PUBLICATIONS

Amantadine Drug Info (2017). Website (http://www.nlm.nih.gov/medlineplus/druginfo/meds/a682064.html; available at least by Dec. 7, 2008; accessed online Sep. 27, 2017, 5 pages.

Ambrozi, et al. Treatment of Impaired Cerebral Function in Psychogeriatric Patients with Memantine—Results of a Phase 11 Double-Blind Study. Pharmacopsychiat. 1988; 21(3): 144-46.

Anand et al., "Dissolution Testing: An FDA Perspective," AAPS Workshop, Physical Pharmacy and Biopharmaceutics, May 13, 2009, 1-32.

Antonelli, et al. Experimental studies and theoretical aspects on A2A/D2 receptor interactions in a model of Parkinson's disease. Relevance for L-dopa induced dyskinesias. Neural Sci 2006;248:16-22.

Aoki et al. (1985). Amantadine kinetics in healthy elderly men: implications for influenza prevention. Clin. Pharmacol. Ther. 37:137-44.

Aoki et al. Amantadine kinetics in healthy young subjects after long-term dosing. Clin. Pharmacol. Ther. 26:729-36.

(56) References Cited

OTHER PUBLICATIONS

Avery's Drug Treatment: Principles and Practice of Clinical Pharmacology and Therapeutics, 3rd Edition, 1987, edited by TrevorM. Speight, Chapter VIII, pp. 255-282.
AXURA Summary of Product Characteristics, 2002, p. 1-16.
Bandini, et al. The visuo-cognitive and motor effect of amantadine in non-Caucasian patients with Parkinson's disease. A clinical and electrophysiological study. J Neural Transm. 2002; 109(1):41-51.
Bara-Jimenez, et al. Effects of serotonin 5-HT1A agonist in advanced Parkinson's disease. Mov Disord 2005; 20:932-936.
Beers, M.H. and Berkow, R. Editors-in-chief, The Merck Manual of Diagnosis and Therapy, 17th Edition, pp. 1525-1544, 1999.
Benson, et al. Optimisation of Drug Delivery 3. Sustained/Controlled-Release Oral Drug Delivery. The Australian Journal of Hospital Pharmacy 27 (1997): 381-389.
Bentue-Ferrer, et al. Medication in Alzheimer's disease, Rev. Geriatr. 26(6):511-522 (2001), (with English summary).
Berman, et al. Antidepressant effects of ketamine in depressed patients. Biol. Psychiatry. 2000; 47:351-354.
Bhat, et al. Localization of the N-methyl-D-aspartate R1 receptor subunit in specific anterior pituitary hormone cell types of the female rat. Neuroendocrinol. 1995; 62(2):178-186.
Bibbiani, et al. Serotonin 5-HT1A agonist improves motor complications in rodent and primate parkinsonian models. Neurology 2001; 27: 1829-1834.
Blanpied, et al. Trapping Channel Block of NMDA-Activated Responses by Amantadine and Memantine, J. of Neurophysiology, 77: 309-323 (1997).
Bliss, et al. A synaptic model of memory: long-term potentiation in the hippocampus. Nature. 1993; 361:31-39.
Bonelli, R. Editorial comment—How to treat vascular dementia? Stroke. Oct. 2003, 34(10):2331-2332.
Bonnett, A. Involvement of Non-Dopaminergic Pathways in Parkinson's Disease: Pathophysiology and Therapeutic Implications. CNS Drugs, vol. 13, No. 5, May 2000, pp. 351-364(14).
Braga, et al. Making crystals from crystals: a green route to crystal engineering and polymorphism, Chemical Communications pp. 3635-3645 (2005).
Bredt, et al. Localization of nitric oxide synthase indicating a neural role for nitric oxide. Nature. 1990; 34 7:768-770.
Breimer, D.D. (1996). "An integrated pharmacokinetic and pharmacodynamics approach to controlled drug delivery," Journal of Drug Targeting 3(6):411-415.
Budziszewska, et al. Antidepressant drugs inhibit glucocorticoid receptor-mediated gene transcription—a possible mechanism. Br. J. Pharmacol. Jul. 2000; 130(6):1385-93.
Bravo, S.A. et al. (2014). Pathophysiology of L-dopa induced dyskinesia—changes in D1/D3 receptors and their signaling pathway, a synopsis of Parkinson's disease. In: Rana AQ, ed. A Synopsis of Parkinson's Disease. London, UK: InTech.
Brooks, D.J. (2008). "Optimizing levodopa therapy for Parkinson's disease with levodopa/carbidopa/entacapone: implications from a clinical and patient perspective," Neuropsychiatr Dis Treat. 4:39-47.
Cacabelos, et al. Pharmacological treatment of Alzheimer disease: From psychotropic drugs and cholinesterase inhibitors to pharmacogenomics. Drugs Today. 2000; 36(7):415-499.
Cder "Guidance for Industry Extended Release Oral Dosage Forms: Development, Evaluation, and Application of In Vitro/In Vivo Correlations" Sep. 1997, U.S. Department of Health and Human Services Food and Drug Administration pp. 1-24.
Cersosimo, et al. Amantadine for the treatment of levodopa dyskinesias in Parkinson's disease. Medicina (B Aires). 2000; 60(3):321-5. (with English translation).
Chen, et al. Open-channel block of N-methyl-D-aspartate (NMDA) responses by memantine: therapeutic advantage against NMDA receptor-mediated neurotoxicity. J. Neurosci. 1992; 12(11):4427-4436.
Choi, DW. Glutamate neurotoxicity and diseases of the nervous system. Neuron. 1988; 1:623-634.
Chung, et al. Clinical pharmacokinetics of doxazosin in a controlled-release gastrointestinal therapeutic system (GITS) formulation, Br. J. Clin. Pharmacol. 1999, 48:678-87.
Calabresi, P. et al. (2014). "Direct and indirect pathways of basal ganglia: a critical reappraisal," Nat Neurosci. 17:1022-30.
Chase, T.N. et al. (1993). "Motor response complications and the function of striatal efferent systems," *Neurology* 43(Suppl 6):S23-S27.
Chemical Abstracts Service Catalog (2006). Published 2006 by Chemical Abstracts Service, p. 52.
ClinicalTrials.Gov (2013). Extended release Amantadine safety and efficacy study in Levodopa-induced Dyskinesia (EASED Study), Located at http://clinicaltrials.gov/archive/nct01397422/2013_05_21, 3 total pages.
Colomiso, et al. Task Force Report on Scales to Assess Dyskinesia in Parkinson's Disease: Critique and Recommendations. Movement Disorders, 2010, p. 1-12.
Crosby, et al. Amantadine for dyskinesia in Parkinson's disease. Cochrane Database of Systematic Reviews 2003, Issue 2. Art. No. CD003467.
Crosby, et al. Amantadine in Parkinson's disease. Cochrane Database of Systematic Reviews 2003, Issue 1. Art. No. CD003468.
Cummings, J. L. Depression and Parkinson's Disease: A Review. The American Journal of Psychiatry. 1992; 149(4): 443-454.
Cutler, RG. Human longevity and aging: possible role of reactive oxygen species. Ann. New York Acad. Sci. 1991; 621: 1-28.
Da Silva-Junior, et al. Amantadine reduces the duration of levodopa-induced dyskinesia: A randomized, double-blind, placebo-controlled study. Parkinsonism Relat Disord. Nov. 2005;11(7):449-52.
Danysz, et al. Aminoadamantanes as NMDA receptor antagonists and antiparkinsonian agents—preclinical studies. Neurosci. Biobehav. Rev. 1997; 21 (4):455-468.
Das, et al. Controlled-Release of Oral Dosage Forms. "Formulation, Fill & Finish," 10-16 (2003).
Daneault, J-F. et al. (2016). "Clinical management of drug-induced dyskinesia in Parkinson's disease: why current approaches may need to be changed to optimise quality of life," Eur Med J. 1:62-69.
Daneault, J.F. et al. (2013). "Drug-induced dyskinesia in Parkinson's disease. Should success in clinical management be a function of improvement of motor repertoire rather than amplitude of dyskinesia?" BMC Med. 11:76.
Daugirdas, et al. Binding of amantadine to red blood cells. Ther Drug Monit. 1984; 6(4):399-401.
Declaration of Richard C. Moreton In Support of Defendants' Opening Claim Construction Brief. Mar. 26, 2015, pp. 1-17.
Declaration of Richard F. Bergstrom, Ph.D. Mar. 26, 2015, pp. 1-50.
Defendants' Opening Claim Construction Brief. Mar. 27, 2015, pp. 1-35.
Defendants' Reply Claim Construction Brief. Jul. 15, 2015, pp. 1-14.
Defendants' Second Revised Joint Initial Invalidity Contentions. Jan. 23, 2015, pp. 1-122.
Del Dotto, et al. Intravenous amantadine improves levadopa-induced dyskinesias: an acute double-blind placebo-controlled study. Mov Disord. May 2001; 16(3):515-20.
Di Monte, et al. Relationship among nigrostriatal denervation, parkinsonism, and dyskinesias in the MPTP primate model. Mov Disord. May 2000;15(3):459-66.
Ditzler, K. Efficacy and Tolerability of Memantine in Patients with Dementia Syndrome, Arnzneim.-Forsch./Drug Res. 41 (II), Nr. 8, 773-780 (1991), Bad Krozingen, Germany.
EBIXA Package leaflet, 2012, p. 1-7.
Engber, et al. NMDA receptor blockade reverses motor response alterations induced by levodopa. Neuroreport. Dec. 20, 1994; 5(18):2586-88.
Erkulwalter and Pillai, Southern Medical Journal, "Amantadine HCI for treatment of dementia," 79:9, Suppl. 2, 30 (1986).
Encarnacion, E.V. et al. (2008). "Levodopa-induced dyskinesias in Parkinson's disease: etiology, impact on quality of life, and treatments," Eur Neurol. 60:57-66.
European search report and search opinion dated Dec. 20, 2016 for EP Application No. 16176422.0.

(56) References Cited

OTHER PUBLICATIONS

European search report dated Apr. 22, 2013 for EP Application No. 10835150.3.
European search report dated Jun. 10, 2011 for EP 10179758.7.
European search report dated Sep. 27, 2010 for EP 10075323.5.
European search report dated Oct. 15, 2007 for Application No. 07000173.0.
Fachinfo-Service: Amantadin-CT 100 mg Filmtabletten. 2004, Rote Liste Service GmbH, Berlin, pp. 1-5. (with English translation).
Fahn, et al. Long-term evaluation of amantadine and levodopa combination in parkinsonism by double-blind crossover analyses. Neurology. Aug. 1975; 25(8):695-700.
Fahn, S. (2005). "Parkinson Study Group. Does levodopa slow or hasten the rate of progression of Parkinson's disease?" J Neurol. 252(Suppl 4):IV37-IV42.
FDA Medical Review for Namenda.RTM. NOA 21-487, Oct. 2, 2003, pp. 1-190.
Fehling, C. The effect of adding amantadine to optimum L-dopa dosage in Parkinson's syndrome. Acta Neural Scand. 1973;49(2):245-51.
Final Office Action dated Aug. 23, 2017, for U.S. Appl. No. 14/307,195, filed Jun. 17, 2014, 35 pages.
Finlay, C. et al. (2014). "Therapeutic potential of targeting glutamate receptors in Parkinson's disease," J Neural Transm (Vienna) 121:861-880.
Fleischhacker, et al. Memantine in the treatment of senile dementia of the Alzheimer type. Prag. Neuropsychopharmacol. Biol. Psychiatry. 1986; 10(1):87-93.
Forest Pharmaceuticals Inc. Namenda 2003 Label.
Forstl, H. Symptomatic therapy of Alzheimer dementia. Wien Med Wochenschr. 2002; 152(3-4):77-80 (with English translation).
Foster, et al. Neurobiology. Taking apart NMDA receptors. Nature. 1987; 329(6138):395-6.
Fox, et al. Memantine combined with an acetyl cholinesterase inhibitor—hope for the future? Neuropsychiatr. Dis. Treat. Jun. 2006; 2(2):121-25.
Franz et al., "Percutaneous Absorption on the Relevance of In Vitro Data," J. Invest. Derm. vol. 64, 1975, pp. 194-195.
Fredriksson, et al. Co-administration of memantine and amantadine with sub/suprathreshold doses of L-Dopa restores motor behaviour of MPTP-treated mice. J. Neural Transm. 2001; 108(2):167-87.
Fung et al., "Drugs for Parkinson's Disease," Australian Prescriber, 24(4) (2001), pp. 92-95.
Galinsky. Basic Pharmacokinetcs. Remington: The Practice and Science of Pharmacy, 20th Ed. (2000), Ch. 58, p. 1127-1144.
Garthwaite, et al. Endothelium-derived relaxing factor release on activation of NMDA receptors suggests role as intercellular messenger in the brain. Nature. 1988; 336(6197):385-88.
Gocovri [prescribing information]. Emeryville, CA: Adamas Pharma, LLC; 2017.
Goetz, C.G. et al. (2008). "The Unified Dyskinesia Rating Scale: presentation and clinimetric profile," Mov Disord. 23:2398-2403.
Goetz et al. Sarizotane as a treatment of dykinesias in parkinson's disease: a double-blind Placebo controlled trial. Mov Disord 2007;22:179-186.
Goetz, et al. Movement Disorder Society Task Force report on the Hoehn and Yahr staging scale: status and recommendations. Mov Disord. Sep. 2004;19(9):1020-8.
Goetz, et al. Movement Disorder Society-sponsored revision of the Unified Parkinson's Disease Rating Scale (MDS-UPDRS): scale presentation and clinimetric testing results. Mov Disord. Nov. 15, 2008;23(15):2129-70.
Gracies JM, Olanow CW; Current and Experimental Therapeutics of Parkinson's Disease; Neuropsychopharmacology: The Fifth Generation of Progress, p. 1802; American College of Neuropsychopharmacology (2002).
Greenamyre et al., "Antiparkinsonian effects of remacemide hydrochloride, a glutamate antagonist, in rodent and primate models of Parkinson's disease" Annals of Neurology, vol. 35, No. 6, 1994, pp. 655-661.
Greenberg, et al. Treatment of Major Depression and Parkinson's Disease with Combined Phenelzine and Amantadine. Am. J. Psychiatry. 1985; 142(2):273-274.
Greene, T.W. Protective Groups in Organic Synthesis. John Wiley & Sons, pp. 70-71 (1981).
Grynkiewicz, et al. A new generation of Ca2+ indicators with greatly improved fluorescence properties. J. Biol. Chem. 1985; 260(6):3440-3450.
Guidance for Industry—Bioavailability and Bioequivalence Studies Submitted in NDAs or INDs—General Considerations. U.S. Department of Health and Human Services Food and Drug Administration Center for Drug Evaluation and Research (CDER). Mar. 2014. Biopharmaceutics.
Guidance for Industry: Food Effect Bioavailability and Fed Bioequivalence Studies. U.S. Department of Health and Human Services, FDA, CDER, Dec. 2002.
Guidance for Industry. Waiver of In Vivo Bioavailability and Bioequivalence Studies for Immediate-Release Solid Oral Dosage Forms Based on a Biopharmaceutics Classification System. U.S. Department of Health and Human Services, FDA, CDER, Aug. 2000.
Guidance for Industry: Bioavailability and Bioequivalence Studies for Orally Administered Drug Products—General Considerations. U.S. Department of Health and Human Services, FDA, CDER, Mar. 2003.
Guide to MS Medications, Multiple Sclerosis Society of Canada, 2004, p. 9.
Guideline on the investigation of bioequivalence. Committee for Medicinal Products for Human Use CHMP), CPMP/EWP/QWP/1401/98 Rev. 1, Jan. 20, 2010.
Guttman, et al. Current concepts in the diagnosis and management of Parkinson's disease. CMAJ. Feb. 4, 2003;168(3):293-301.
Hartmann, et al. Tolerability of memantine in combination with cholinesterase inhibitors in dementia therapy. Int. Clin. Physchopharmacol, 2003, 18(2):81-85.
Hauser, R.A. et al. (2000). "A home diary to assess functional status in patients with Parkinson's disease with motor fluctuations and dyskinesia," Clin. Neuropharmacol. 23:75-81.
Hayden, F.G. et al. (1983). "Differences in side effects of amantadine hydrochloride and rimantadine hydrochloride relate to differences in pharmacokinetics," Antimicrob Agents Chemother. 23:458-464.
Hayden, et al. Comparative single-dose pharmacokinetics of amantadine hydrochloride and rimantadine hydrochloride in young and elderly adults. Antimicrob Agents Chemother. Aug. 1985;28(2):216-21.
Hayden, et al. Comparative Toxicity of Amantadine Hydrochloride and Rimantadine Hydrochloride in Healthy Adults. Antimicrobial Agents and Chemotherapy, vol. 19, No. 2, Feb. 1981, p. 226-233.
Hechtner, M.C. et al. (2014). "Quality of life in Parkinson's disease patients with motor fluctuations and dyskinesias in five European countries," Parkinsonism Relat Disord. 20:969-974.
Hoffman, A. Pharmacodynamic aspects of sustained release preparations. Adv Drug Deliv Rev. Sep. 7, 1998;33(3): 185-199.
Ing et al., "Toxic Effects of Amantadine in Patients with Renal Failure," CMA Journal, Mar. 1979, vol. 120, pp. 695-697.
International Search Report dated Sep. 30, 2014, for PCT Application No. PCT/US2014/42690, filed on Jun. 17, 2014, 3 pages.
International search report dated Feb. 7, 2011 for PCT/US2010/058789.
International search report dated Aug. 9, 2006 for PCT Application No. PCT/US2005/42780.
International search report dated Apr. 5, 2002 for PCT Application No. US2001/48516.
International search report dated May 8, 2006 for PCT Application No. US2005/42424.
International Search Report for PCT/US2006/013506, dated Jan. 12, 2007, Feb. 23, 2007 Corrected.
Jackson, et al. Chemoprophylaxis of viral respiratory diseases. Pan American Health Organization. 1967;595-603.
Jackson, "Prevention and control of influenza by chemoprophylaxis and chemotherapy. Prospects from examination of recent experience," JAMA, 235(25), (1976), 2739-2742.
Jain, et al. Polymorphism in Pharmacy, Indian Drugs 23(6):315-29 (1986).

(56) References Cited

OTHER PUBLICATIONS

Jenner, P. Preventing and controlling dyskinesia in Parkinson's disease—a view of current knowledge and future opportunities. Mov Disord. 2008;23 Suppl 3:S585-98.
Jones, R.W. Drug treatment of Alzheimer's disease. Reviews in Clinical Gerontology (2002) vol. 12, pp. 165-173.
Karcz-Kubicha, et al. Anxiolytic activity of glycine-B antagonists and partial agonists—no relation to intrinsic activity in the patch clamp. Neuropharmacol. 1997; 36(10):1355-67.
Khlebtovsky, A. et al. (2012). "Patient and caregiver perceptions of the social impact of advanced Parkinson's disease and dyskinesias," J Neural Transm (Vienna) 119:1367-1371.
Klockgether, et al. NMDA antagonists potentiate antiparkinsonian actions of L-dopa in monoamine-depleted rats. Ann. Neural. Oct. 1990; 28(4):539-46.
Klockgether, et al. Excitatory amino acids and the basal ganglia: implications for the therapy of Parkinson's disease. Trends Neurosci. 1989; 12(8):285-286.
Konitsiotis, et al. AMPM receptors blockade improves levodopa-induced dyskinesia in MPTP monkeys. Neurology 2000;54: 1589-1595.
Kornhuber, et al. Amantadine and Memantine are NMDA receptor antagonists with neuroprotective properties. J. Neural Transm. Suppl. 1994; 43:91-104.
Kornhuber, et al. Cerebrospinal fluid and serum concentrations of the N-methyl-D-aspartate (NMDA) receptor antagonist memantine in man. Neurosci. Lett. 1995; 195(2): 137-39.
Kornhuber, et al. Effects of the 1-amino-adamantanes at the MK-801-binding site of the NMDA-receptor-gated ion channel: a human postmortem brain study. Eur J. Pharmacol. 1991; 206(4):297-300.
Kornhuber, et al. Memantine displaces [3H]MK-801 at therapeutic concentrations in postmortem human frontal cortex. Eur. J. Pharmacol. 1989; 166(3):589-90.
Lees, A.J. (1989). "The on-off phenomenon," J. Neurol. Supplement, pp. 29-37.
Letter from British Library dated Aug. 11, 2008 re MMW Fortschritte.
Lewitt, et al. Adenosine A2A receptor antagonist istradefylline (KW-6002) reduces "off" time in Parkinson's disease: a double-blind, randomized, multicenter clinical trial (6002-US-005). Ann Neural 2008;63:295-302.
Longer, M. A. Sustained-Release Drug Delivery Systems. In Remington's Pharmaceutical Sciences (1990) (Mack Publishing Company, 1990, 18th Ed.; Chapter 91: 1676-1693.
Luginger, et al. Beneficial effects of amantadine on L-dopa-induced dyskinesias in Parkinson's disease. Mov Disord. Sep. 2000;15(5):873-8.
Manson, et al. Idazoxan is ineffective for levodopa-induced dyskinesias in Parkinson's disease. Mov Disord 2000;15:336-337.
Marcea et al., Effect of memantine versus dh-Ergotoxin on Cerebra-organic Psycho-syndrome. Therapiewoche. 1988, 38:3097-3100 (with English summary).
McLean, et al. Prophylactic and therapeutic efficacy of memantine against seizures produced by soman in the rat. Toxicol Appl Pharmacol. Jan. 1992; 112(1):95-103.
MedlinePlus: Amantadine citation retrieved from https://www.nlm.nih.gov/medlineplus/druginfo/meds/a682064.html. Accessed Jan. 25, 2016. Published Sep. 1, 2010.
Merims, et al. Riluzole for levodopa-induced dyskinesias in advanced Parkinson's disease. Lancet. May 22, 1999; 353(9166):1764-65.
Metman, et al. A trial of dextromethorphan in parkinsonian patients with motor response complications. Mov. Disord. May 1998;13(3):414-17.
Metman, et al. Amantadine as treatment for dyskinesias and motor fluctuations in Parkinson's disease. Neurology. May 1998; 50(5):1323-26.
Metman, et al. Amantadine for levodopa-induced dyskinesias: a 1-year follow-up Study. Arch Neural 1999;56: 1383-1386.
Morrison, D. et al. (2007). A randomized, crossover study to evaluate the pharmacokinetics of amantadine and oseltamlvlr administered alone and in combination, PLoS ONE 2(12):e1305.
Moryl, et al. Potential antidepressive properties of amantadine, memantine and bifemelane. Pharmacol. Toxicol. 1993; 72(6):394-397.
Müller, T. et al. (2007). "Prevalence and treatment strategies of dyskinesia in patients with Parkinson's disease," J Neural Transm (Vienna). 114:1023-1026.
Namenda label. ND 21-487, pp. 1-20. Forest Pharmaceuticals, Inc.
Navarro, R. et al. (May 20-24, 2017). "An assessment of the persistence and medical possession ratio of adjunctive treatments to levodopa in patients with Parkinson's disease (PD)," Presented at: ISPOR 22nd Annual International Meeting, Boston, MA.
Neutel, et al. (1996). "Novel delivery system for verapamil designed to achieve maximal blood pressure control during the early morning," American Heart Journal 132:1202-1206.
ND 21-487 Namenda Approved Labeling. 2003; p. 1-20.
Non-Final Office Action dated Oct. 26, 2016, for U.S. Appl. No. 14/307,195, filed Jun. 17, 2014, 24 pages.
Non-Final Office Action dated May 3, 2018, for U.S. Appl. No. 14/307,195, filed Jun. 17, 2014, 14 pages.
Note for guidance on modified release oral and transdermal dosage forms: Section II (Pharmacokinetic and clinical evaluation). Committee for proprietary medicinal products, CPMP/EWP/280/96, Jul. 28, 1999.
Notice of allowance dated Jan. 23, 2015 for U.S. Appl. No. 14/451,262.
Notice of allowance dated May 18, 2015 for U.S. Appl. No. 14/591,641.
Notice of allowance dated Jan. 24, 2013 for U.S. Appl. No. 11/286,448.
Notice of allowance dated Apr. 11, 2014 for U.S. Appl. No. 12/959,321.
Notice of allowance dated Jun. 4, 2014 for U.S. Appl. No. 13/958,153.
Notice of allowance dated Oct. 9, 2014 for U.S. Appl. No. 14/328,440.
Notice of allowance dated Oct. 9, 2014 for U.S. Appl. No. 14/451,242.
Notice of allowance dated Oct. 9, 2014 for U.S. Appl. No. 14/451,250.
Notice of allowance dated Oct. 10, 2014 for U.S. Appl. No. 14/451,282.
Notice of allowance dated Oct. 14, 2014 for U.S. Appl. No. 14/451,273.
Notice of allowance dated Oct. 15, 2014 for U.S. Appl. No. 14/451,226.
Notice of Allowance dated Dec. 7, 2017 for U.S. Appl. No. 15/428,878.
Notice of Allowance dated Nov. 17, 2017 for U.S. Appl. No. 15/428,899.
Notice of Allowance dated Nov. 16, 2017 for U.S. Appl. No. 15/428,980.
Notice of Allowance dated Oct. 26, 2017 for U.S. Appl. No. 15/430,084.
Notice of Allowance dated Oct. 1, 2018, for U.S. Appl. No. 14/307,195, filed Jun. 17, 2014, 12 pages.
Oertel, W. et al. (2017). "Randomized, placebo-controlled trial of ADS-5102 (amantadine) extended-release capsules for levodopa-induced dyskinesia in Parkinson's disease (EASE LID 3)," Mov Disord. 32:1701-1709.
Office action dated Jan. 12, 2017 for U.S. Appl. No. 14/863,035.
Office action dated Mar. 16, 2015 for U.S. Appl. No. 14/591,687.
Office action dated Mar. 16, 2015 for U.S. Appl. No. 14/591,707.
Office action dated Mar. 17, 2015 for U.S. Appl. No. 14/591,641.
Office action dated Mar. 20, 2015 for U.S. Appl. No. 14/523,688.
Office action dated Mar. 24, 2015 for U.S. Appl. No. 14/523,477.
Office action dated Mar. 24, 2015 for U.S. Appl. No. 14/523,565.
Office action dated Mar. 24, 2015 for U.S. Appl. No. 14/523,607.
Office action dated Mar. 27, 2015 for U.S. Appl. No. 14/523,535.
Office action dated Mar. 31, 2015 for U.S. Appl. No. 14/523,589.
Office action dated Apr. 1, 2015 for U.S. Appl. No. 14/523,674.
Office action dated Apr. 3, 2015 for U.S. Appl. No. 14/591,662.
Office action dated May 31, 2016 for U.S. Appl. No. 14/863,035.
Office action dated Jun. 10, 2015 for U.S. Appl. No. 14/267,597.
Office action dated Jul. 1, 2016 for U.S. Appl. No. 14/857,509.
Office action dated Jul. 6, 2016 for U.S. Appl. No. 14/863,051.
Office action dated Jul. 18, 2016 for U.S. Appl. No. 14/863,002.
Office action dated Jul. 27, 2016 for U.S. Appl. No. 14/863,067.

(56) References Cited

OTHER PUBLICATIONS

Office action dated Aug. 1, 2016 for U.S. Appl. No. 14/865,773.
Office Action dated Aug. 15, 2016 for U.S. Appl. No. 14/856,398.
Office Action dated Aug. 18, 2016 for U.S. Appl. No. 14/865,830.
Office action dated Aug. 25, 2016 for U.S. Appl. No. 14/865,736.
Office action dated Sep. 22, 2014 for U.S. Appl. No. 14/451,262.
Office action dated Oct. 2, 2015 for U.S. Appl. No. 14/052,507.
Office action dated Nov. 28, 2016 for U.S. Appl. No. 14/856,406.
Office action dated Dec. 29, 2014 for U.S. Appl. No. 14/267,597.
Office action dated Jan. 5, 2009 for U.S. Appl. No. 11/286,448.
Office action dated Mar. 5, 2012 for U.S. Appl. No. 11/286,448.
Office action dated Mar. 7, 2012 for U.S. Appl. No. 12/959,321.
Office action dated Mar. 29, 2011 for U.S. Appl. No. 11/286,448.
Office action dated Apr. 15, 2013 for U.S. Appl. No. 12/840,132.
Office action dated Apr. 16, 2013 for U.S. Appl. No. 13/756,275.
Office action dated Apr. 29, 2013 for U.S. Appl. No. 12/959,321.
Office action dated May 7, 2012 for U.S. Appl. No. 12/959,321.
Office action dated May 20, 2014 for U.S. Appl. No. 13/958,153.
Office action dated Jul. 13, 2012 for U.S. Appl. No. 12/840,132.
Office action dated Jul. 22, 2010 for U.S. Appl. No. 11/286,448.
Office action dated Aug. 7, 2013 for U.S. Appl. No. 12/959,321.
Office Action dated Aug. 8, 2014 for U.S. Appl. No. 13/863,140.
Office action dated Sep. 16, 2009 for U.S. Appl. No. 11/286,448.
Office Action dated Sep. 22, 2014 for U.S. Appl. No. 14/328,440.
Office Action dated Sep. 22, 2014 for U.S. Appl. No. 14/451,226.
Office Action dated Sep. 22, 2014 for U.S. Appl. No. 14/451,242.
Office Action dated Sep. 22, 2014 for U.S. Appl. No. 14/451,250.
Office Action dated Sep. 22, 2014 for U.S. Appl. No. 14/451,273.
Office Action dated Sep. 23, 2014 for U.S. Appl. No. 14/451,282.
Office action dated Oct. 26, 2012 for U.S. Appl. No. 13/559,478.
Office action dated Nov. 20, 2013 for U.S. Appl. No. 13/958,153.
Office Action dated Jul. 19, 2017 for U.S. Appl. No. 15/428,899, filed Feb. 9, 2017, 18 pp.
Office Action dated Jul. 13, 2017 for U.S. Appl. No. 15/430,084, filed Feb. 10, 2017, 18 pp.
Office Action dated May 19, 2017 for U.S. Appl. No. 15/428,878, filed Feb. 9, 2017, 16 pp.
Office Action dated Jun. 16, 2017 for U.S. Appl. No. 15/428,980.
Olanow, C.W. et al. (2009). "The scientific and clinical basis for the treatment of Parkinson disease," Neurology 72(21Suppl 4):S1-S136.
Olanow, et al. Multicenter, openlabel, trial of sarizotan in Parkinson disease patients with levodopa-induced dyskinesias (the SPLENDID Study). Clin Neuropharmacol 2004;27:58-62.
Opposition by Adamas Pharmaceuticals, Inc. against the grant of European Patent 150923281 in the name of H. Lundbeck A/S dated Aug. 19, 2009.
Opposition by Dr. Gabriele Ahrens against the grant of European Patent 2 506 709 in the name of Adamas Pharmaceuticals, Inc. dated Apr. 20, 2017, 32 total pages.
Ozdilek, B. et al. (2012). "Motor and non-motor symptoms in Turkish patients with Parkinson's disease affecting family caregiver burden and quality of life," J Neuropsychiatry Clin Neurosci. 24:478-483.
Pact, et al. Amantadine for dyskinesia in patients affected by severe Parkinson's disease. Neurological Sciences 22.1 (2001): 75-76.
Pahwa R. et al. (Sep. 20-23, 2016). "ADS-5102 (amantadine HCl) Extended-release capsules improves activities of daily living in Parkinson's disease patients by reducing levodopa-induced dyskinesia: a post-hoc analysis from the phase 3 EASE LID study," Presented at: 4th World Parkinson Congress, Portland, OR.
Phawa, R. et al. (Jun. 16-20, 2013). "Randomized trial of extended release Amantadine in Parkinson's disease patients with Levodopa-induced Dyskinesia (EASED study)," 17th International Congress of Parkinson's disease and movement disorders (MDS), Sydney, Australia.
Pahwa, R. et al. (2017). "ADS-5102 (amantadine) extended-release capsules for levodopa-induced dyskinesia in Parkinson disease (EASE LID Study): a randomized clinical trial," JAMA Neurol. 74:941-949.
Pahwa, R. et al. (2015). "Amantadine extended release for levodopa-induced dyskinesia in Parkinson's disease (EASED Study)," Mov Disord. 30:788-795.
Pahwa, et al. Practice Parameter: treatment of Parkinson disease with motor fluctuations and dyskinesia (an evidence-based review): report of the Quality Standards Subcommittee of the American Academy of Neurology. Neurology. Apr. 11, 2006; 66(7):983-95.
Papa, et al. Levodopa-induced dyskinesias improved by a glutamate antagonist in Parkinsonian monkeys. Ann Neural. May 1996;39(5):574-8.
Parkes, D. (1974). Amantadine. Adv. Drug. Res. 8:11-81.
Parkes, J. D. Clinical pharmacology of amantadine and derivatives. Early Diagnosis and Preventive Therapy in Parkinson's Disease. Springer Vienna, 1989. 335-341.
Parkes, et al. Amantadine dosage in treatment of Parkinson's disease. The Lancet. 1970; 295:1130-1133.
Parkes, et al. Treatment of Parkinson's disease with amantadine and levodopa. A one-year study. Lancet. May 29, 1971;1(7709):1083-7.
Parsons et al.: 'Glutamate in CNS disorders as a target for drug development: an update', XP002908604 Retrieved from STN Database accession No. 131:13198 & Drug News Perspect. vol. 11, No. 9, 1998, pp. 523-569.
Parsons, et al. Memantine is a clinically well tolerated N-methyl-D-aspartate (NMDA) receptor antagonist—a review of preclinical data. Neuropharmacology, 38:735-767 (1999).
Pharmaceutical Dosage Forms: Tablets, Second Edition, Revised and Expanded, published by Marcel Dekker, Inc., edited by Lieberman, Lachman, and Schwartz. 1990; pp. 462-472.
Pharmacokinetics, Drugs and the Pharmaceutical Sciences, Gibaldi and Perrier Eds., vol. 1, (1975), pp. 101-102.
PK-Merz® film-coated tablet, "Summary of Product Characteristics." 2003, p. 1-11.
Qiu, Y. et al. (2000). "Research and development aspects of oral controlled-release dosage forms," Chapter 23, Handbook of Pharmaceutical Controlled Release Technology, Marcel Dekker, Inc., pp. 465-503.
Raisch, D.W. et al. (2005). "The new drug approval process and clinical trial design," Chapter 48 in *Remington: The science and practice and pharmacy*, 21st edition, Lippincott Williams & Wilkins, pp. 965-975.
Rajput, et al. New use for an old drug: amantadine benefits levodopa induced dyskiensias. Mov Disord 1998;13:851-854.
Rascol, et al. Idazoxan, an alpha-2 antagonist, and L-DOPA-induced dyskinesias in patients with Parkinson's disease. Mov Disord 2001; 16:708-713.
Rausch, et al. Effects of L-deprenyl and amantadine in an MPTP-model of parkinsonism. J. Neural Transm. 1990; 32:269-275.
Reisberg, et al. Memantine in moderate-to-severe Alzheimer's disease, N. Eng. J. Med. 2003; 348(14):1333-1341.
Remington's The Science and Practice of Pharmacy, 21st Ed., pp. 944-945, 1179, 1199-1202 (2006).
Restriction Requirement dated Aug. 28, 2018, for U.S. Appl. No. 15/985,300, filed May 21, 2018, 6 pages.
Riederer, et al. Pharmacotoxic psychosis after memantine in Parkinson's disease. Lancet. 1991; 338: 1022-1023.
Ruzicka, et al. Amantadine infusion treatment of motor fluctuations and dyskinesias in Parkinson's disease. J Neural Trans 2000; 102: 1297-1306.
Reply Declaration of Richard F. Bergstrom, Ph.D. Jul. 15, 2015, pp. 1-14.
Rollins. Clinical Pharmacokinetics. Remington: The Practice and Science of Pharmacy, 20th Ed. (2000), Ch. 59, p. 1145-1155.
Sakai, Saari. How to Read or Understand a Prescription. Insomnia. Journal of Recipe 2008 7(2), p. 16-28 (with English translation).
Sansom, L.R. Oral extended-release products. Aust. Prescr. 1999, 22:88-90.
Savery, F. Amantadine and a fixed combination of levodopa and carbidopa in the treatment of Parkinson's disease. Dis Nerv Syst. Aug. 1977;38(8):605-8.
Schmidt, et al. Excitatory amino acids and Parkinson's disease. Trends Neurosci. 1990; 13(2):46-47.

(56) References Cited

OTHER PUBLICATIONS

Schneider, et al. Effects of oral memantine administration on Parkinson symptoms. Results of a placebo-controlled multicenter study. Dtsch. Med. Wschr. 1984; 109(25):987-990. (with English abstract).
Schwab, et al. Amantadine in Parkinson's Disease Review of More Than Two Years' Experience. JAMA, vol. 222, No. 7, Nov. 13, 1972, p. 792-795.
Schwab, et al. Amantadine in the treatment of Parkinson's disease. JAMA. May 19, 1969;208(7):1168-70.
Shafer, S.L. (1991). "Targeting the effect site with a computer controlled infusion pump," Advanced methods of pharmacokinetic and pharmacodynamics systems analysis, Plenum Press, New York, NY., pp. 185-197.
Shannon, et al. Amantadine and motor fluctuations in chronic Parkinson's disease. Clin Neuropharmacol. Dec. 1987;10(6):522-6.
Shefrin, SL. Therapeutic advances in idiopathic Parkinsonism. Expert Opin. Investig. Drugs. Oct. 1999; 8(10):1565-1588.
Siemers, E. Recent progress in the treatment of Parkinson's disease. Comprehensive Therapy. 1992; 18(9):20-24.
Schermer M. (2011). "Ethical issues in deep brain stimulation," Front Integr Neurosci. 5:17.
Silver, et al. Livedo reticularis in Parkinson's disease patients treated with amantadine hydrochloride. Neurology. Jul. 1972;22(7):665-9.
Silverman, R. The Organic Chemistry of Drug Design and Drug Action, published 1992 by Academic Press, pp. 19-21 and 352-397.
Snow, et al. The effect of amantadine on levodopa-induced dyskinesias in Parkinson's disease: a double-blind, placebo-controlled study. Clin Neuropharmacol. Mar.-Apr. 2000;23(2):82-5.
Spieker, et al. The NMDA antagonist budipine can alleviate levodopa-induced motor fluctuations. Mov. Disord. May 1999; 14(3):517-19.
Standaert, et al. Chapter 22: Treatment of central nervous system degenerative disorders. Goodman and Gilman's The Pharmacological Basis of Therapeutics 10th Ed., Hardman Limbird and Gilman Eds., McGraw-Hill, New York, 2001.
Stedman's Medical Dictionary. 27th ed. Lippincott, Williams and Wilkins. Baltimore 2000.
Stegemann, S. (2002). "Hard gelatin capsules today—and tomorrow," Capsugel Quality, $2^{nd}$ edition, pp. 3-23.
Sviridov, et al. C-hydroxyalkylation of N-adamantylanilines by hexafluoroacetone and methyl trifluoropyruvate. Izv. Akad. Nauk. SSSR, Ser. Khim. 1989; 10:2348-2350 (with English translation).
Symmetrel. Amantadine hydrochloride. Retrieved from the internet: URL—http://www.pbs.gov.au/meds%2Fpi%2Fnvpsymor10611.pdf (retrieved on Jul. 25, 2012). Published Jun. 29, 2011.
Symmetrel [prescribing information]. (2009). Chadds Ford, PA: Endo Pharmaceuticals Inc.
Tal, M. A novel antioxidant alleviates heat hyperalgesia in rats with an experimental painful peripheral neuropathy. Neuroreport. May 31, 1996; 7(8):1382-84.
Tariot, et al. Memantine treatment in patients with moderate to severe Alzheimer disease already receiving donepezil: a randomized controlled trial. JAMA, 2004, 291 (3):317-324.
Tempel, D. Memantine in the organic brain syndrome psycho. Therapiewoche. 1989;39:946-952 (with English summary).
Thanvi, et al. Long term motor complications of levodopa: clinical features, mechanisms, and management strategies. Postgrad Med J. Aug. 2004;80(946):452-8.
The Merck Manual of Diagnosis and Therapy, 17th Edition, published 1999 by Merck Research Laboratories, pp. 1393-1400.
Third Party Submission in Published Application Under 37 C.F.R. 1.99 dated Apr. 20, 201 O regarding U.S. Appl. No. 12/512,701, filed Jul. 30, 2009. 149 pgs.
Thomas, et al. Duration of amantadine benefit on dyskinesia of severe Parkinson's disease. Neural Neurosurg Psychiatry 2004;75:141-143.
Timmer, et al. Pharmacokinetic evaluation of gepirone immediate-release capsules and gepirone extended-release tablets in healthy volunteers. J Pharm Sci. Sep. 2003;92(9):1773-8.
Timmins, et al. Optimization and characterization of a pH-independent extended-release hydrophilic matrix tablet. Pharm Dev Technol. Feb. 1997;2(1):25-31.
Toda, H. et al. (2016). "Update on deep brain stimulation for dyskinesia and dystonia: a literature review," Neurol Med Chir (Tokyo). 56:236-248.
Toutain, et al. Bioavailability and its assessment. J Vet Pharmacol Ther. Dec. 2004;27(6):455-66.
Troy, et al. Bioavailability of once-daily venlafaxine extended release compared with the immediate-release formulation in healthy adult volunteers. Current Therapeutic Research. Aug. 1997; 58(8):492-503.
Vale, et al. Amantadine in depression. Lancet. 1971; 11:437.
Vippagunta, et al. Crystalline Solids, Advanced Drug Delivery Reviews 48:3-26 (2001).
Vitale, et al. Unawareness of dyskinesias in Parkinson's and Huntington's diseases. Neural Sci. Feb. 2001;22(1):105-6.
Wakelkamp, M. et al. (1998). "The influence of drug input rate on the development of tolerance to frusemide," Br. J. Clin. Pharmacol. 46:479-487.
Walker, et al. A qualitative and quantitative evaluation of amantadine in the treatment of Parkinson's disease. J Chronic Dis. Mar. 1972;25(3):149-82.
Walker, et al. Amantadine and levodopa in the treatment of Parkinson's disease. Clin Pharmacol Ther. Jan.-Feb. 1972;13(1):28-36.
Walsh, et al. Parkinson's Disease and Anxiety. Postgraduate Medical Journal, Feb. 2001; 77:89-93.
Warren, et al. The use of amantadine in Parkinson's disease and other Akinetic-rigid disorders. ACNR 2004; 4(5):38-41.
Wessell, et al. NR2B selective NMDA receptor antagonist CP-101,606 prevents levodopa-induced motor response alterations in hemi-parkinsonian rats. Neuropharmacology. Aug. 2004; 47(2): 184-94.
Wilkinson, GR. Chapter 1: Pharmacokinetics. Goodman and Gilman's The Pharmacological Basis of Therapeutics 10th Ed., Hardman Limbird and Gilman Eds., McGraw-Hill, New York, 2001.
Williams, et al. Calcium gradients in single smooth muscle cells revealed by the digital imaging microscope using Fura-2. Nature. 1985; 318:558-561.
Wilson, et al. Combination drug regimens hold great promise for Alzheimer treatment. Science Blog. Available at http://www.scienceblog.com/community/older/archives/K/5/pub5611.html.
Wimo, et al. Pharmacoeconomics and dementia. Abstracts from the 8th International Conference on Alzheimer's Disease and Related Disorders. Stockholm, Sweden. Jul. 20-25, 2002. No. 541.
Wolf, et al. Long-term antidyskinetic efficacy of amantadine in Parkinson's disease. Mov Disord. Published on line Mar. 2, 2010.
Written Opinion of the International Searching Authority dated Sep. 30, 2014, for PCT Application No. PCT/US2014/42690, filed on Jun. 17, 2014, 6 pages.
Written opinion dated Feb. 7, 2011 for PCT/US2010/058789.
Written opinion dated Aug. 8, 2006 for PCT Application No. PCT/US2005/42780.
Yamada, el at. Changes in symptoms and plasma homovanillic acid with amantadine hydrochloride in chronic schizophrenia. Biol. Psychiatry. May 15, 1997; 41 (10):1062-64.
Zesiewicz, T.A. et al. (2007). "Levodopa-induced Dyskinesia in Parkinson's Disease: Epidemiology, Etiology, and Treatment," Movement Disorders, pp. 302-310.
Ziemann, et al. Pharmacological control of facilitatory I-wave interaction in the human motor cortex. A paired transcranial magnetic stimulation study. Electroencephalogr. Clin. Neurophysiol. 1998; 109(4):321-330.
Co-pending U.S. Appl. No. 15/397,200, filed Jan. 3, 2017.
Co-pending U.S. Appl. No. 15/400,179, filed Jan. 6, 2017.
Co-pending U.S. Appl. No. 15/408,213, filed Jan. 17, 2017.
Co-pending U.S. Appl. No. 15/416,409, filed Jan. 26, 2017.
Co-pending U.S. Appl. No. 15/419,809, filed Jan. 30, 2017.
Co-pending U.S. Appl. No. 15/432,866, filed Feb. 14, 2017.
Co-pending U.S. Appl. No. 15/434,491, filed Feb. 16, 2017.
U.S. Appl. No. 60/701,857, filed Jul. 22, 2005.
U.S. Appl. No. 15/941,803, filed Mar. 30, 2018, by Went et al

(56) References Cited

OTHER PUBLICATIONS

U.S. Appl. No. 16/203,384, filed Nov. 28, 2018, by Went et al.
U.S. Appl. No. 16/677,431, filed Nov. 7, 2019, by Went et al.
U.S. Appl. No. 16/727,263, filed Dec. 26, 2019, by Went et al.

FIG. 7

| | | Placebo (N=22) | 260 mg ADS-5102 (N=20) | 340 mg ADS-5102 (N=21) | 420 mg ADS-5102 (N=20) |
|---|---|---|---|---|---|
| Age (yrs), Mean (SD) | | 65.5 (10.2) | 67.5 (8.6) | 64.7 (10.0) | 66.4 (9.4) |
| Sex n (%) | Male | 14 (63.6) | 8 (40.0) | 13 (61.9) | 10 (50.0) |
| Ethnicity n (%) | Hispanic | 1 (4.5) | 2 (10.0) | 0 | 2 (10.0) |
| | Not Hispanic | 21 (95.5) | 18 (90.0) | 21 (100) | 18 (90.0) |
| Race n (%) | White | 20 (90.9) | 18 (90.0) | 20 (95.2) | 17 (85.0) |
| Time since PD Diagnosis (yrs), Mean (SD) | | 10.7 (7.1) | 8.9 (3.4) | 9.3 (4.9) | 9.0 (3.5) |
| Duration of Levodopa Treatment (yrs), Mean (SD) | | 9.0 (7.0) | 6.9 (3.7) | 8.2 (5.3) | 8.3 (3.2) |
| Duration of LID (yrs), Mean (SD) | | 4.1 (4.1) | 3.3 (2.6) | 4.4 (3.4) | 3.6 (2.0) |
| FSS, Mean (SD) | | 4.9 (1.2) | 4.4 (1.5) | 4.8 (1.4) | 4.8 (1.1) |
| MMSE, Mean (SD) | | 28.6 (1.8) | 28.6 (2.0) | 28.8 (1.5) | 28.2 (2.0) |
| Hoehn and Yahr, Mean (SD) | | 2.5 (0.74) | 2.5 (0.89) | 2.5 (0.69) | 2.4 (0.75) |
| UDysRS, Total, Mean (SD) | | 39.2 (17.8) | 39.8 (13.5) | 43.8 (12.1) | 41.9 (12.0) |

FIG. 8

| Outcome Measure | 360 mg ADS-5102 (N=19) | 340 mg ADS-5102 (N=20) | 420 mg ADS-5102 (N=19) |
|---|---|---|---|
| | LS Mean Treatment Difference vs. Placebo (95% CI) | | |
| 24-Hour PD Diary: | | | |
| ON Time w/o Troublesome Dyskinesia, hours | 3.3 (1.1, 5.5) p=0.004 | 3.0 (0.8, 5.2) p=0.008 | 2.7 (0.5, 5.0) p=0.018 |
| ON Time w/ Troublesome Dyskinesia, hours | -1.3 (-3.1, 0.6) p=0.169 | -1.8 (-3.6, 0.0) p=0.055 | -2.8 (-4.6, -0.9) p=0.003 |
| ON Time w/ Dyskinesia, hours | -1.1 (-3.7, 1.5) p=0.408 | -2.1 (-4.8, 0.5) p=0.117 | -3.1 (-5.8, -0.5) p=0.021 |
| OFF Time, hours | -1.3 (-2.7, 0.1) p=0.074 | -0.9 (-2.3, 0.5) p=0.199 | 0.1 (-1.4, 1.5) p=0.934 |
| Sleep Time, hours | -0.8 (-1.8, 0.2) p=0.099 | -0.4 (-1.4, 0.6) p=0.387 | -0.3 (-1.2, 0.7) p=0.573 |
| MDS-UPDRS (part I, II, III) | 1.2 (-7.7, 10.1) p=0.786 | -2.2 (-11.3, 6.9) p=0.636 | 1.7 (-7.2, 10.6) p=0.705 |
| MDS-UPDRS (part IV, Item 4.1) - Time Spent with Dyskinesia | -0.2 (-0.8, 0.5) p=0.630 | -0.6 (-1.2, 0.1) p=0.100 | -0.6 (-1.3, 0.0) p=0.057 |
| MDS-UPDRS (part IV, Item 4.2) - Functional Impact of Dyskinesia | -0.8 (-1.4, -0.2) p=0.014 | -1.0 (-1.6, -0.4) p=0.002 | -1.3 (-2.0, -0.7) p<0.001 |

No significant treatment group differences vs. placebo were noted in the Fatigue Severity Scale (FSS) or the PDQ-39.

FIG. 9

| Safety Overview | Placebo (N=22) | 260 mg ADS-5102 (N=20) | 340 mg ADS-5102 (N=21) | 420 mg ADS-5102 (N=20) |
|---|---|---|---|---|
| Number (%) of Subjects with any AEs | 18 (82) | 16 (80) | 20 (95) | 18 (90) |
| Serious AEs | 0 | 1 (5) | 0 | 4 (20) |
| Severe AEs | 3 (14) | 1 (5) | 3 (14) | 7 (35) |
| Discontinued due to AE | 0 | 3 (15) | 3 (14) | 8 (40) |

FIG. 10

Treatment Emergent Adverse Events in >10% (>2 subjects) in any Active Treatment Group

| Preferred Term, n (%) | Placebo (N=22) | 260 mg ADS-5102 (N=20) | 340 mg ADS-5102 (N=21) | 420 mg ADS-5102 (N=20) |
|---|---|---|---|---|
| Constipation | 2 (9.1) | 7 (35.0) | 5 (23.8) | 3 (15.0) |
| Dizziness | 1 (4.5) | 3 (15.0) | 6 (28.6) | 3 (15.0) |
| Dry mouth | 0 | 3 (15.0) | 4 (19.0) | 2 (10.0) |
| Hallucination, visual | 0 | 3 (15.0) | 3 (14.3) | 2 (10.0) |
| Fall | 3 (13.6) | 1 (5.0) | 3 (14.3) | 3 (15.0) |
| Confusional state | 1 (4.5) | 1 (5.0) | 3 (14.3) | 2 (10.0) |
| Headache | 1 (4.5) | 1 (5.0) | 3 (14.3) | 1 (5.0) |
| Nausea | 1 (4.5) | 1 (5.0) | 3 (14.3) | 1 (5.0) |
| Asthenia | 1 (4.5) | 0 | 3 (14.3) | 1 (5.0) |

METHODS OF ADMINISTERING AMANTADINE

CROSS-REFERENCE TO RELATED APPLICATIONS

This application is a continuation application of U.S. patent application Ser. No. 14/307,195, filed Jun. 17, 2014, now issued as U.S. Pat. No. 10,154,971, which claims priority to U.S. Provisional Patent Application No. 61/836,082, filed Jun. 17, 2013, the entire contents of which applications are incorporated herein by reference in their entireties.

BACKGROUND OF THE INVENTION

Amantadine is indicated for various conditions that can be treated by NMDA receptor antagonists including the treatment of idiopathic Parkinson's disease (Paralysis Agitans), post-encephalitic Parkinsonism, and symptomatic Parkinsonism which may follow injury to the nervous system by carbon monoxide intoxication. Amantadine also has activity as a viral M2 channel inhibitor and is used for the prophylaxis and treatment of infection of viral diseases, especially influenza A virus.

Levodopa, the most commonly prescribed and effective drug treatment for symptomatic relief in Parkinson's disease (PD) is associated with dose-limiting motor side-effects, including abnormal involuntary movements known as levodopa-induced dyskinesia (LID). With continued levodopa treatment, and as PD progresses to moderate and severe stages, dyskinesias can become severely disabling and have been associated with a decrease in the quality of life. Encarnacion, E. V. and Hauser, R. A., Levodopa-induced dyskinesias in Parkinson's disease: etiology, impact on quality of life, and treatments. Eur Neurol, 2008. 60(2): p. 57-66. There are currently no medications approved for the treatment of LID, thus there is a significant unmet medical need.

LID may require a reduction in the levodopa dose causing patients to receive sub-optimal PD treatment. The treatment of LID that becomes severely disabling resulting in a decrease in the quality of life is an unmet medical need. Encarnacion et al., supra.

Amantadine HCl (amantadine) is a weak, non-competitive N-methyl d-aspartate (NMDA) receptor antagonist that promotes release of dopamine. Guttman, M., Kish, S. J., Furukawa, Y., Current concepts in the diagnosis and management of Parkinson's disease. Cmaj, 2003. 168(3): p. 293-301. Amantadine has shown efficacy in animal models of LID and is used off-label by neurologists and movement disorder specialists to treat LID in patients with PD. Blanchet, P. J., Konitsiotis, S., Chase, T. N., Amantadine reduces levodopa-induced dyskinesias in parkinsonian monkeys. Mov Disord, 1998. 13(5): p. 798-802. Fox, S. H., Lang, A. E., Brotchie, J. M., Translation of non-dopaminergic treatments for levodopa-induced dyskinesia from MPTP-lesioned nonhuman primates to phase IIa clinical studies: keys to success and roads to failure. Mov Disord, 2006. 21(10): p. 1578-94.

A number of small studies with different designs and outcome measures in PD patients have shown amantadine (IR formulation) to be effective in the treatment of LID. At amantadine doses of 200 mg/day, an approximately 25% reduction in LID was reported (da Silva-Junior, F. P., Braga-Neto, P., Monte, F. S., et al., Amantadine reduces the duration of levodopa-induced dyskinesia: a randomized, double-blind, placebo-controlled study. Parkinsonism Relat Disord, 2005. 11(7): p. 449-52; Snow, B. J., Macdonald, L., Mcauley, D., et al., The effect of amantadine on levodopa-induced dyskinesias in Parkinson's disease: a double-blind, placebo-controlled study. Clin Neuropharmacol, 2000. 23(2): p. 82-85) and at doses of 300 mg/day, the reduction of LID was reported to be ~40% (Luginger, E., Wenning, G. K., Bosch, S., et al., Beneficial effects of amantadine on L-dopa-induced dyskinesias in Parkinson's disease. Mov Disord, 2000. 15(5): p. 873-8; Paci, C., Thomas, A., Onofrj, M., Amantadine for dyskinesia in patients affected by severe Parkinson's disease. Neurol Sci, 2001. 22(1): p. 75-6; Thomas, A., Iacono, D., Luciano, A. L., et al., Duration of amantadine benefit on dyskinesia of severe Parkinson's disease. J Neurol Neurosurg Psychiatry, 2004. 75(1): p. 141-3.) In one study conducted at 300 to 400 mg/day, the reduction was reported to be ~60% (Metman, L. V., Del Dotto, P., Lepoole, K., et al., Amantadine for levodopa-induced dyskinesias: a 1-year follow-up study. Arch Neurol, 1999. 56(11): p. 1383-6.) In general, the reduction in LID appears to increase with increasing amantadine dose.

Despite amantadine's reported utility in the treatment of LID, the drug has not been extensively studied in well-controlled clinical trials that meet regulatory standards of acceptance, nor has the optimal dose for this indication been established. Moreover, while amantadine has shown benefits in treating the symptoms of early PD, it has been shown to have no effect on motor fluctuations (i.e., ON/OFF) in later stages. (Luginger E, Wenning G K, Bösch S, Poewe W., "Beneficial effects of amantadine on L-dopa-induced dyskinesias in Parkinson's disease." *Mov. Disord.* 2000 September; 15(5):873-8.) Doses of 200 mg/day of amantadine (IR formulation) have been generally tolerated by the majority of PD patients. However, at this dose level, amantadine efficacy in LID is sub-optimal for many patients. Doses of 300 mg/day or higher amantadine IR produce greater reduction in LID symptoms but are associated with central nervous system (CNS) side effects including hallucinations, insomnia, nausea and dizziness (lightheadedness) (Jackson et al., supra; [Hayden, Jackson]. Currently marketed forms of amantadine are immediate release formulations that are typically administered two or more times a day. Amantadine's use is limited by dose related CNS side effects including dizziness, confusion, hallucinations, insomnia and nightmares (Gracies J M, Olanow C W; Current and Experimental Therapeutics of Parkinson's Disease; *Neuropsychopharmacology: the Fifth Generation of Progress* pp 1802; American College of Neuropsychopharmacology 2002), which can be particularly exacerbated when amantadine is administered late in the day (Jackson et al., Bull Pan Am Health Org, 147, 595-603 (1967)); Jackson, JAMA, 235 (25), (1976), 2739-2742; and Hayden, AAC, 23(3) 1983, pp. 458-464).

It is known that immediate release amantadine can act as a stimulant, causing insomnia and sleep disturbance. Therefore, the last dose is typically administered no later than 4 pm in order to minimize these side effects. Such dosing of amantadine results in peak plasma amantadine concentrations occurring in the evening or night, and very low plasma concentrations in the morning.

Extended release forms of amantadine have been described in the art. U.S. Pat. No. 5,358,721, to Guittard et al., and U.S. Pat. No. 6,217,905, to Edgren et al., each disclose an oral osmotic dosage form comprising an antiviral or anti-Parkinson's drug, respectively, where in each case amantadine is listed as a possible drug to be utilized in the dosage form. U.S. Pat. No. 6,194,000, to Smith et al., discloses analgesic immediate and controlled release pharmaceutical compositions utilizing NMDA receptor antagonists, such as amantadine, as the active agent. U.S. Patent Appl. Publication Nos. US 2006/0252788, US 2006/0189694 (U.S. Pat. No. 8,389,578), US 2006/0142398, US 2008/0227743, and US2011/0189273 (U.S. Pat. No. 8,741,343), all to Went et al., each disclose the administration of an NMDA receptor antagonist, such as amantadine, optionally in controlled release form.

SUMMARY OF THE INVENTION

The inventors have developed methods of administering amantadine, wherein administration of amantadine, or a pharmaceutically acceptable salt thereof (such as amantadine hydrochloride) at 260-420 mg once nightly to Parkinson's disease patients is well tolerated, provides an improvement in Parkinson's symptoms, motor fluctuations, levodopa induced dyskinesia (LID), and provides an improvement in physician's Clinical Global Impression of Change (CGIC). Doses at 420 mg result in higher discontinuation rates, but comparable frequency of side effects. The effectiveness measures for 260-420 mg once nightly amantadine (or a pharmaceutically acceptable salt thereof) are superior to higher and lower doses of amantadine. The 340 mg dose administered once nightly was the only dose tested which provided the benefits of being well tolerated, providing benefits in PD symptoms; motor fluctuations; significant improvement in LID; and significant improvement in CGIC. In some aspects of the invention, amantadine, or a pharmaceutically acceptable salt thereof (such as the hydrochloride) is administered at 260-420 mg once nightly, 0 to 4 hours before bedtime without sleep related adverse effects in patients with Parkinson's disease, and one (or more) of the following: A. LID in the patients is significantly improved; B. the PD symptoms are improved; C. the Clinical Global Impression of Change is significantly improved (relative to placebo); and/or D. the Clinical Global Impression of Change is significant, whereas higher and lower doses are not significantly different from placebo. In some aspects of the invention, the dyskinesia metrics in A can be from UDysRS or some of other form of metrics, infra.

In some aspects of the invention, amantadine, or a pharmaceutically acceptable salt thereof (such as the hydrochloride) is administered at 260 to 420 mg (preferably 340 mg) once nightly, 0 to 4 hours before bedtime to subjects with Parkinson's disease, resulting in one or more of the following: A. the daily ON time without troublesome dyskinesia is increased relative to placebo; B. the daily ON time without dyskinesia is increased relative to placebo; C. the daily ON time with dyskinesia is decreased relative to placebo (or in a dose responsive manner); D. the daily ON time with troublesome dyskinesia is decreased relative to placebo (or in a dose responsive manner); and/or E. the daily OFF time is decreased relative to placebo and/or higher amantadine dosage strengths. Thus, in some embodiments, administration of this drug once nightly before bedtime provides marked improvement on following day measurements of efficacy (e.g., increase in ON time without dyskinesia, decrease in OFF time, improvement in dyskinesia) and/or tolerability. The inventors have identified a need in the art for improved formulations, and methods of treatment with such formulations, of amantadine (or a pharmaceutically acceptable salt thereof) that result in a patient having higher plasma concentrations of amantadine upon waking in the morning without adversely affecting sleep compared with conventional amantadine therapy. In particular, the inventors have identified a need in the art for a method of administering amantadine, or a pharmaceutically acceptable salt thereof, in the late afternoon or evening, e.g., after 4 pm, which reduces side effects of insomnia and sleep disturbance and provides effective plasma concentrations of amantadine upon waking.

Therefore, there exists a need in the art for improved methods of amantadine therapy for the treatment of Parkinson's disease, LID in Parkinson's Disease, and the overall symptoms of Parkinson's Disease, including motor fluctuations, which can be administered to a patient shortly before they wish to sleep (e.g., at bedtime) without causing insomnia or sleep disturbance. In addition, there is a need for an amantadine therapy which can be taken by the patient before they go to sleep and then provides a suitable plasma concentration of amantadine when they wake up, e.g., in the morning, after a full night's sleep.

In some aspects of the invention, a method of administering amantadine to a patient in need thereof is provided, said method comprising orally administering certain extended release (ER) compositions comprising amantadine, or a pharmaceutically acceptable salt thereof, less than three hours before bedtime (i.e., the time at which the subject wishes to go to sleep for the night). This aspect also includes the use of such compositions and the use of amantadine for the manufacture of a medicament as described below. Alternatively, the composition is administered less than about 4 hours before bedtime.

In some aspects, administration occurs less than two and a half, less than two, less than one and a half, less than one or less than half hour before bedtime.

In some aspects, the invention provides a method of reducing sleep disturbance in a human subject undergoing treatment with amantadine, said method comprising administering an extended release (ER) composition comprising amantadine, or a pharmaceutically acceptable salt thereof, less than about three hours before bedtime (i.e., the time at which the subject wishes to go to sleep for the night). This aspect also includes the use of such compositions and the use of amantadine for the manufacture of a medicament as described below. Alternatively, the composition is administered less than about 4 hours before bedtime.

In some aspects of the invention, amantadine, or a pharmaceutically acceptable salt thereof (such as the hydrochloride) is administered at a reduced amount, i.e. 85 to 260 mg per day, for at least one week prior to once daily administration of the maintenance dose. This titration period may improve tolerability of the maintenance dose. In one aspect of the invention, patients are administered 85 or 170 mg per day for at least one week prior to increasing the dose to 170 or 340 mg per day.

In some aspects, the invention provides a method of treating levodopa induced dyskinesia, or fatigue, or dementia, or any other symptom of Parkinson's disease, said method comprising administering an extended release (ER) composition comprising amantadine, or a pharmaceutically acceptable salt thereof, less than about three hours before bedtime (i.e., the time at which the subject wishes to go to sleep for the night). This aspect also includes the use of such compositions and the use of amantadine for the manufacture of a medicament as described below.

In some aspects, the invention provides a method of treating brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders, said method comprising administering certain extended release (ER) compositions comprising amantadine, or a pharmaceutically acceptable salt thereof, less than about three hours before bedtime (i.e., the time at which the subject wishes to go to sleep for the night). This aspect also includes the use of such compositions and the use of amantadine for the manufacture of a medicament as described below.

In some embodiments of any of the above aspects the patient has been diagnosed with Parkinson's disease.

In some embodiments of any of the above aspects, the composition is administered once nightly. In another aspect, the daily dose is from 260 to 340 mg (preferably 340 mg). In some embodiments, the daily dose of 260 to 340 mg is given in 1, 2 or 3 capsules of size 0, 1 or 2, in normal and/or EL formats.

In some embodiments of any of the above aspects, administration of the composition to a Parkinson's disease patients results in a significant reduction in levodopa induced dyskinesia (LID). In a specific embodiment, administration of the composition results in about 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by the FDA to evaluate effectiveness of drugs indicated to reduce LID. In further specific embodiments, the scale used in measuring the reduction in LID could be UDysRS, UPDRS Part IV (subscores 32, 33), MDS-UPDRS Part IV and subscores 4.1 and 4.2, Dyskinesia Rating Scale (DRS), Abnormal Involuntary Movement Scale (AIMS), or other scales developed for this purpose.

In some embodiments of any of the above aspects, administration of the composition to a Parkinson's disease patients results in a significant reduction in Parkinson's disease symptoms, including motor fluctuations. In a specific embodiment, administration of the composition results in about 5%, 10%, 15%, 20%, 25%, 30%, 35%, or 40% reduction in Parkinson's symptoms, including motor fluctuations. In further specific embodiments, the reduction in Parkinson's symptoms is measured on a numeric scale that is used by the FDA to evaluate effectiveness of drugs indicated to reduce Parkinson's symptoms, including motor fluctuations. In further specific embodiments, the scale used in measuring the reduction in Parkinson's symptoms, including motor fluctuations, could be the Unified Parkinson's Disease Rating Scale (UPDRS), MDS-UPDRS, or analysis of PD Diary data (for motor fluctuations).

In some embodiments of any of the above aspects, administration of the composition to a patient results in a significant improvement in Clinician Global Impression (CGI) or any other physician measurement of a patient's overall condition. In a specific embodiment, administration of the composition results in about 5%, 10%, 15%, 20%, 25%, 30%, 35%, or 40% improvement in CGI. In further specific embodiments, the improvement in CGI is measured on a numeric scale that is used by the FDA to evaluate effectiveness of drugs indicated to treat CNS disorders.

In some embodiments of any of the above aspects, there is no increase in plasma concentration of amantadine for at least one hour after the administration at steady state plasma concentrations.

In some embodiments of any of the above aspects, there is no increase in the plasma concentration of amantadine for at least two hours after the administration at steady state plasma concentrations.

In some embodiments of any of the above aspects, the administration of the composition to a human subject at steady state amantadine plasma concentrations increases the amantadine plasma concentration by less than 5%, 10%, 15%, 20% or 25% at 1, 2, 2.5 or 3 hours following such administration. For example, administration of the composition to a human subject at steady state amantadine plasma concentrations increases the amantadine plasma concentration by less than 5% at 1, 2, 2.5 or 3 hours following such administration; or by less than 10% at 1, 2, 2.5 or 3 hours following such administration; or by less than 15% at 1, 2, 2.5 or 3 hours following such administration; or by less than 20% at 1, 2, 2.5 or 3 hours following such administration; or by less than 25% at 1, 2, 2.5 or 3 hours following such administration.

In some embodiments of any of the above aspects the amantadine has a single dose T max of 9 to 18 hours. In more specific embodiments, the amantadine has a single dose T max of 12 to 18 hours after administration.

In some embodiments of any of the above aspects the amantadine has a steady state T max of 7 to 13 hours. In more specific embodiments, the amantadine has a steady state T max of 8 to 12 hours after administration.

In some embodiments of any of the above aspects, a once nightly oral administration of the composition to a human subject provides a steady state plasma concentration profile characterized by a concentration increase of amantadine of less than 25% at three hours after the administration. In more specific embodiments, the steady state plasma concentration profile is characterized by a concentration increase of amantadine of less than 25% at four hours after the administration.

In some embodiments of any of the above aspects, the composition is administered once a day and the ratio of Cmax to Cmin at steady state is 1.3 to 1.8, or, more specifically, 1.4 to 1.7, or, more specifically, about 1.6.

In embodiments of any of the above aspects, the steady state plasma concentration profile following multiple administrations to a human subject of the composition at bedtime is—characterized by an average plasma concentration during the day ("C-ave-day", defined as the average day time amantadine plasma concentration as measured in a human PK study) that is 1.4 to 1.7 times the average plasma concentration during the night ("C-ave-night", defined as the average night time amantadine plasma concentration as measured in a human PK study). In more specific embodiments the C-ave-day is the average amantadine plasma concentration as measured between the hours of 5 am, 6 am, 7 am, 8 am or 9 am to the hours of 4 pm, 5 pm, 6 pm, 7 pm or 8 pm; for example, between the hours of 6 am and 4 pm, between the hours of 7 am and 6 pm, or between the hours of 7 am and 5 pm. The C-ave-night is the average amantadine plasma concentration as measured between the hours of 4 pm, 5 pm, 6 pm, 7 pm, 8 pm, 9 pm, 10 pm or 11 pm to the hours of 5 am, 6 am, 7 am, 8 am or 9 am; for example, between the hours of 10 pm and 6 am, between the hours of 7 pm and 6 am, or between the hours of 8 pm and 6 am.

In some embodiments of any of the above aspects the amantadine is administered as a pharmaceutically acceptable salt. In a more specific embodiment, the amantadine is administered as amantadine hydrochloride or amantadine sulfate.

In some embodiments of any of the above aspects, the once nightly dose of amantadine, or pharmaceutically acceptable salt thereof, may be in the range of 260 to 420 mg. In other embodiments, the once nightly dose of amantadine, or pharmaceutically acceptable salt thereof, exceeds 300 mg per day, e.g., is between 320 and 360 mg per day, more specifically is between 330 and 350 mg per day. In various specific embodiments, the daily dose of amantadine or pharmaceutically acceptable salt thereof may be 300 to 315 mg, 310 to 325 mg, 320 to 335 mg, 330 to 345 mg, 340 to 355 mg, or 350 to 365 mg. In some particularly preferred embodiments, the once nightly dose of amantadine, or pharmaceutically acceptable salt thereof, is 340 mg.

In some embodiments of any of the above aspects, the once nightly composition is administered as one, two, three or four unit dosage forms in unequally or, preferably, equally divided units. In some more specific embodiments, the composition is administered as two or three unit dosage forms each comprising 85 to 175 mg amantadine, or a pharmaceutically acceptable salt thereof.

In some embodiments of any of the above aspects, the composition is administered as two or three unit dosage forms of unequal, or preferably equal, dosage, each comprising 85 to 250 mg amantadine, or a pharmaceutically acceptable salt thereof. In some more specific embodiments, the composition is administered as two unit dosage forms each comprising 150 to 180 mg amantadine, or a pharmaceutically acceptable salt thereof.

In some embodiments of any of the above aspects, oral administration of a single dose of the composition to a cohort of human healthy volunteer subjects in a fasted state provides an average maximum plasma concentration (Cmax) of 1.1 to 1.7 ng/ml per mg of amantadine. In more specific embodiments, oral administration of a single dose of the composition to a cohort of human subject in a fasted state provides an average maximum plasma concentration (Cmax) of 1.2 to 1.5 ng/ml per mg of amantadine and an $AUC_{0\text{-}inf}$ (Area under the concentration-curve curve from t=0 to t=infinity) of 46 to 56 ng*h/mL per mg of amantadine.

In some embodiments of any of the above aspects, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0\text{-}24}$ of 46 to 56 ng*h/mL per mg of amantadine. In more specific examples, all three criteria of (i), (ii) and (iii) are met.

In more specific embodiments, the steady state plasma concentration profile is further characterized by: (iv) no increase in concentration of amantadine for at least one hour after the administration; and (v) Cmax/Cmin ratio of 1.4 to 1.7. In more specific embodiments, both criteria of (iv) and (v) are met.

In other aspects, the present invention provides a method of treating Parkinson's disease and/or LID in a human subject in need thereof, said method comprising orally administering a composition of any of the above aspects. In a preferred aspect, the present invention provides a method of treating disease in a human subject in need thereof, said method comprising orally administering a composition of any of the above aspects once nightly at nighttime, administering 1, 2 or 3 dosage forms.

References to administering amantadine to a subject in need thereof include treating a patient with a disease or condition, including an iatrogenic condition (e.g., LID), which may be treated, prevented or cured by a NMDA antagonist. More specifically, administering amantadine to a subject in need thereof includes treating a patient with Parkinson's Disease, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders and other CNS disorders.

Some embodiments described herein provide a method of improving CGI in a patient with Parkinson's disease, comprising administering to said patient once nightly, 0 to 4 hours before bedtime a composition comprising 260 to 420 mg amantadine, or a pharmaceutically acceptable salt thereof, and at least one release modifying excipient. In some embodiments, the composition comprises 260 to 340 mg amantadine, or a pharmaceutically acceptable salt thereof. In some embodiments, the composition comprises 260 mg amantadine, or a pharmaceutically acceptable salt thereof. In some embodiments, the composition comprises 340 mg amantadine, or a pharmaceutically acceptable salt thereof. In some embodiments, the change in CGI is determined in a placebo controlled, double blind clinical study.

Some embodiments described herein provide a method resulting in at least one, preferably at least two, of the results selected from the group consisting of (A) increasing ON time without troublesome dyskinesia; and (B) reducing OFF time; and (C) improving CGI; in a patient with a CNS disorder, comprising administering to said patient once nightly, 0 to 4 hours before bedtime a composition comprising 260 to 420 mg amantadine, or a pharmaceutically acceptable salt thereof, and at least one release modifying excipient. In some embodiments, the composition comprises 260 to 340 mg amantadine, or a pharmaceutically acceptable salt thereof. In some embodiments, the composition comprises 260 mg amantadine, or a pharmaceutically acceptable salt thereof. In some embodiments, the composition comprises 340 mg amantadine, or a pharmaceutically acceptable salt thereof. In some embodiments, the change in ON time without dyskinesia, the OFF time and/or the CGI are determined in a placebo controlled, double blind clinical study using the PD Home diary. In some embodiments, the CGI is determined by a question completed by the investigator.

Some embodiments described herein provide a method resulting in at least one, preferably at least two, of the results selected from the group consisting of (A) increasing ON time without troublesome dyskinesia; and (B) reducing OFF time; and (C) improving CGI; in a patient with a CNS disorder, comprising administering to said patient once daily, a composition comprising 260 to 420 mg amantadine, or a pharmaceutically acceptable salt thereof, and at least one release modifying excipient. In some embodiments, the composition comprises 260 to 340 mg amantadine, or a pharmaceutically acceptable salt thereof. In some embodiments, the composition comprises 260 mg amantadine, or a pharmaceutically acceptable salt thereof. In some embodiments, the composition comprises 340 mg amantadine, or a pharmaceutically acceptable salt thereof. In some embodiments, the change in ON time without dyskinesia, the OFF time and/or the CGI are determined in a placebo controlled, double blind clinical study using the PD Home diary. In some embodiments, the CGI is determined by a question completed by the investigator. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0\text{-}inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine; in more specific methods, all three criteria of (i), (ii) and (iii) are met.

The PD home diary is described in Hauser, et al., "A Home Diary to Assess Functional Status in Patients with Parkinson's Disease with Motor Fluctuations and Dyskinesia", Clin. Neuropharmacol., 23(3), pp. 75-81 (2000), which is incorporated herein by reference in its entirety. As used herein, the terms "ON time" and "OFF time," have the meanings described by Hauser et al. Id. Briefly, ON time is the period during which Parkinson's medication is providing benefit with regard to mobility, slowness, and stiffness; and OFF time is the period during which Parkinson's medication has worn off and is no longer providing benefit with regard to mobility, slowness, and stiffness. Id. These measures of time are separate from the scales used to measure reduction in LID, which primarily assess the change in dyskinesia severity or intensity. As such, these scales capture the benefit throughout the day and night of a given treatment for all four motor states. A preferred product profile includes benefits across this measure.

Dyskinesia is involuntary twisting, turning movements. Id. These movements are an effect of medication (i.e., levodopa) and occur during ON time. Id. Dyskinesia is distinct from tremor, which is shaking back and forth, a symptom of the underlying Parkinson's disease. Troublesome dyskinesia is dyskinesia that causes at least some difficulty with function. Id.

BRIEF DESCRIPTION OF THE DRAWINGS

FIG. 7 is a table showing demographics and baseline characteristics of subjects from Example 11.

FIG. 8 is a table showing additional analyses: changes from baseline to week 8 versus placebo; from Example 11.

FIG. 9 is a table providing a safety overview for subjects from Example 11.

FIG. 10 is a table showing treatment emergent adverse effects (AEs) in >10% (>2 subjects) in any active treatment group from Example 7.

DETAILED DESCRIPTION OF THE INVENTION

Figure 1:
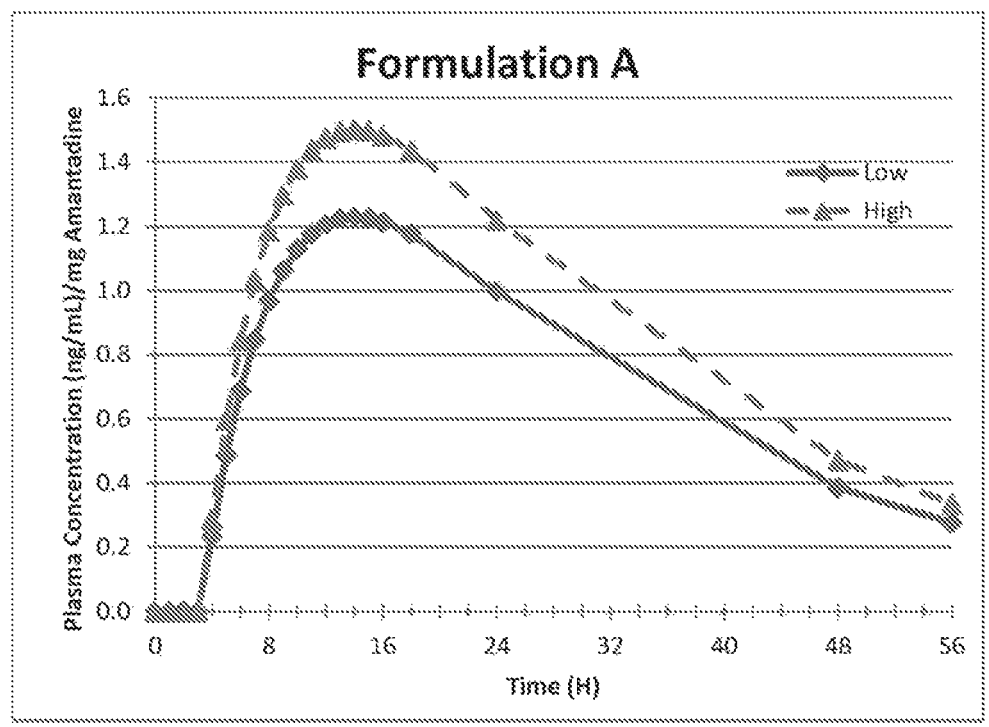
FIG. 1 shows a plot of mean (SD) plasma amantadine concentrations versus scheduled time for Formulation A.

Some embodiments described herein provide a method of increasing the ON time without dyskinesia in a patient with Parkinson's disease, comprising administering to the patient once nightly, 0 to 4 hours before bed time, a composition comprising 260 to 420 mg amantadine, or a pharmaceutically acceptable salt thereof (e.g., amantadine hydrochloride) and at least one release modifying excipient. In some such methods, the change in ON time without dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of reducing the ON time with dyskinesia in a patient with Parkinson's disease comprising administering to said patient once nightly, 0 to 4 hours before bed time a composition comprising 260 to 420 mg amantadine, or a pharmaceutically acceptable salt thereof (e.g., amantadine hydrochloride), and at least one release modifying excipient. In some such methods, the change in ON time with dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of reducing the ON time with troublesome dyskinesia in a patient with Parkinson's disease, comprising administering to said patient once nightly, 0 to 4 hours before bed time, a composition comprising 260 to 420 mg amantadine, or a pharmaceutically acceptable salt thereof (e.g., amantadine hydrochloride), and at least one release modifying excipient. In some such methods, the change in ON time without troublesome dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of reducing the OFF time in a patient with Parkinson's disease comprising administering to said patient once nightly, 0 to 4 hours before bed time, a composition comprising 260 to 340 mg amantadine, or a harmaceutically acceptable salt thereof (e.g., amantadine hydrochloride), and at least one release modifying excipient. In some such methods, the change in OFF time is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of increasing the ON time without troublesome dyskinesia without increasing sleep disturbances in a patient with Parkinson's disease comprising administering to said patient once nightly, 0 to 4 hours before bed time a composition comprising 260 to 420 mg amantadine, or a pharmaceutically acceptable salt thereof (e.g., amantadine hydrochloride), and at least one release modifying excipient. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of improving Clinician's Global Impression without increasing sleep disturbances in a patient with Parkinson's disease comprising administering to said patient once nightly, 0 to 4 hours before bed time a composition comprising 260 to 420 mg amantadine, or a pharmaceutically acceptable salt thereof (e.g., amantadine hydrochloride), and at least one release modifying excipient. In some such methods, the dose of amantadine, or pharmaceutically acceptable salt thereof, is from 300 to 360 mg per day, particularly 330 to 350 mg per day, and in particular 340 mg per day.

Some embodiments described herein provide a method of increasing the ON time without dyskinesia in a patient with Parkinson's disease, comprising administering to the patient once daily, a composition comprising 260 to 420 mg amantadine, or a pharmaceutically acceptable salt thereof (e.g., amantadine hydrochloride) and at least one release modifying excipient. In some such methods, the change in ON time without dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0-inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine; in more specific methods, all three criteria of (i), (ii) and (iii) are met.

Some embodiments described herein provide a method of reducing the ON time with dyskinesia in a patient with Parkinson's disease comprising administering to said patient once daily, a composition comprising 260 to 420 mg amantadine, or a pharmaceutically acceptable salt thereof (e.g., amantadine hydrochloride), and at least one release modifying excipient. In some such methods, the change in ON time with dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0-inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine; in more specific methods, all three criteria of (i), (ii) and (iii) are met.

Some embodiments described herein provide a method of reducing the ON time with troublesome dyskinesia in a patient with Parkinson's disease, comprising administering to said patient once daily, a composition comprising 260 to 420 mg amantadine, or a pharmaceutically acceptable salt thereof (e.g., amantadine hydrochloride), and at least one release modifying excipient. In some such methods, the change in ON time without troublesome dyskinesia is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0-inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine; in more specific methods, all three criteria of (i), (ii) and (iii) are met.

Some embodiments described herein provide a method of reducing the OFF time in a patient with Parkinson's disease comprising administering to said patient once daily, a composition comprising 260 to 340 mg amantadine, or a pharmaceutically acceptable salt thereof (e.g., amantadine hydrochloride), and at least one release modifying excipient. In some such methods, the change in OFF time is determined in a placebo controlled, double blind clinical study using the PD Home Diary. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0-inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0\text{-}24}$ of 46 to 56 ng*h/mL per mg of amantadine; in more specific methods, all three criteria of (i), (ii) and (iii) are met.

Some embodiments described herein provide a method of increasing the ON time without troublesome dyskinesia without increasing sleep disturbances in a patient with Parkinson's disease comprising administering to said patient once daily, a composition comprising 260 to 420 mg amantadine, or a pharmaceutically acceptable salt thereof (e.g., amantadine hydrochloride), and at least one release modifying excipient. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0\text{-}inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0\text{-}24}$ of 46 to 56 ng*h/mL per mg of amantadine; in more specific methods, all three criteria of (i), (ii) and (iii) are met.

Some embodiments described herein provide a method of improving Clinician's Global Impression without increasing sleep disturbances in a patient with Parkinson's disease comprising administering to said patient once daily, a composition comprising 260 to 420 mg amantadine, or a pharmaceutically acceptable salt thereof (e.g., amantadine hydrochloride), and at least one release modifying excipient. In some such methods, the dose of amantadine, or pharmaceutically acceptable salt thereof, is from 300 to 360 mg per day, particularly 330 to 350 mg per day, and in particular 340 mg per day. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0\text{-}inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0\text{-}24}$ of 46 to 56 ng*h/mL per mg of amantadine; in more specific methods, all three criteria of (i), (ii) and (iii) are met.

The invention also provides a method of reducing sleep disturbances in a patient undergoing treatment with amantadine. The method comprises administering amantadine to a patient in need thereof, such that the amantadine does not interfere with sleep, yet provides maximum benefit in morning hours when often needed most by many patients who take amantadine and further, provides nighttime coverage of symptoms of Parkinson's disease if needed. Nighttime coverage includes providing benefit if the patient wakes up and wishes to return to sleep. In some such methods, the C-ave-day is 1.4 to 1.7 times the C-ave-night; in preferred methods the C-ave-day is measured between the hours of 8 am to 8 pm and the C-ave-night is measured between the hours of 8 pm to 8 am. In some such methods, administration of a single dose of the composition to a cohort of human healthy volunteer subjects in a fasted state provides an average maximum plasma concentration (Cmax) of 1.1 to 1.7 ng/ml per mg of amantadine or an $AUC_{0\text{-}inf}$ (Area under the concentration-curve curve from t=0 to t=infinity) of 46 to 56 ng*h/mL per mg of amantadine or both. In some such methods, the daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0\text{-}24}$ of 46 to 56 ng*h/mL per mg of amantadine; in more specific methods, all three criteria of (i), (ii) and (iii) are met.

The method of the invention comprises orally administering to the patient an extended release (ER) amantadine composition designed for nighttime administration. The composition is taken less than three hours before bedtime, and preferably less than two and a half, less than two, less than one and a half, or less than one hour before bedtime. Most preferably the ER amantadine composition is taken less than half hour before bedtime (i.e., the time at which the subject wishes to go to sleep for the night). Alternatively, the composition is administered less than about 4 hours before bedtime.

As used herein, a reference to amantadine is intended to encompass pharmaceutically acceptable salts thereof (e.g., amantadine hydrochloride, amantadine sulfate, etc.).

As used herein, "extended release" includes "controlled release", "modified release", "sustained release", "timed release", "delayed release", and also mixtures of delayed release, immediate release, enteric coated, etc. with each of the above.

The patient may be diagnosed with any disease or disorder for which amantadine is prescribed, such as Parkinson's disease, multiple sclerosis, drug-induced extrapyramidal reactions, levodopa-induced dyskinesia, and viral diseases (e.g., influenza, HBV, and HCV). In a specific embodiment, the patient has Parkinson's disease, which, as used herein, also encompasses a diagnosis of parkinsonism. In one embodiment, the patient has early stage Parkinson's disease, and the amantadine is used as a monotherapy or in combination with a monoamine oxidase type B (MAO-B) inhibitor without concomitant use of levodopa. In another embodiment, the patient has late stage Parkinson's disease and the patient takes levodopa in addition to the amantadine. In another embodiment, the patient has multiple sclerosis and the amantadine is used for the treatment of fatigue. In other embodiments, the patient has a brain injury, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, or a neuropsychiatric disorder.

An ER amantadine composition for use in the invention is adapted for nighttime administration by providing a plasma concentration profile that does not interfere with the subject's sleep. The composition of the invention will, upon administration to a human subject, result in a gradual initial increase in plasma concentration of amantadine such that, at steady state conditions, administration of a dose of the composition results in an increase in plasma concentration of amantadine of less than 25% at three hours after the dose is administered. For example, if a subject's steady state plasma concentration of amantadine is 500 ng/ml at the time a dose of the composition is administered, three hours later the subject's plasma concentration of amantadine will be less than 625 ng/ml. Preferably, the increase in plasma concentration of amantadine three hours after administration is less than 15%, and most preferably, less than 10%. Particularly preferred compositions have a plasma concentration profile further characterized by no increase in amantadine plasma concentration, or even a decrease (at steady state conditions), for at least one or, in a preferred embodiment, two hours after the administration. The composition for use in the invention is further adapted for bedtime (i.e. the time at which the subject wishes to go to sleep for the night) administration by providing a maximum concentration of amantadine (Cmax) in the morning hours. The time to reach Cmax (T max), as measured after single dose administration in the fasted state, is at least, 9 hours and up to 15, 16, 17, or 18 hours, or at least 10 hours and up to 14, 15, 16, 17, or 18 hours, or at least 12 hours, and up to 14, 15, 16, or 17 hours. In specific embodiments, the T max is 9 to 18 hours, most preferably 12 to 18 hours. At steady state, with once nightly administration of the composition, the T max is 7 to 13 hours, most preferably 8 to 12 hours. A suitable ER amantadine composition may be further characterized by having a steady-state Cmax/Cmin ratio of 1.3 to 1.8, and preferably 1.4 to 1.7, resulting in a composition with daily profile.

In more specific, preferred embodiments, the plasma concentration profile is further characterized by having an AUC profile after administration of a single dose of the composition characterized by: a fractional AUC from 0 to 4 hours that is less than 5%, and preferably less than 3% of $AUC_{0-inf}$; a fractional AUC from 0 to 8 hours that is about 5 to 15%, and preferably about 8 to 12% of $AUC_{0-inf}$; a fractional AUC from 0 to 12 hours that is about 10 to 40%, and preferably about 15 to 30% of $AUC_{0-inf}$; a fractional AUC from 0 to 18 hours that is about 25 to 60%, and preferably about 30 to 50% of $AUC_{0-inf}$; and a fractional AUC from 0 to 24 hours that is about 40 to 75%, and preferably about 50 to 70% of $AUC_{0-inf}$.

In a further preferred embodiment, the plasma concentration profile is further characterized by having an AUC profile after once nightly dosing of the composition at steady state conditions characterized by: a fractional AUC from 0 to 4 hours that is about 2 to 25%, and preferably about 5 to 20% of $AUC_{0-24}$; a fractional AUC from 0 to 8 hours that is about 15 to 50%, and preferably about 20 to 40% of $AUC_{0-24}$; a fractional AUC from 0 to 12 hours that is about 30 to 70%, and preferably about 40 to 60% of $AUC_{0-24}$: and a fractional AUC from 0 to 18 hours that is about 60 to 95%, and preferably about 75 to 90% of $AUC_{0-24}$.

In some embodiments of any of the above aspects, the steady state plasma concentration profile following multiple administrations to a human subject of the composition at bedtime is characterized by an average plasma concentration during the day ("C-ave-day", defined as the average day time amantadine plasma concentration as measured in a human PK study) that is 1.1 to 2.0 times the average plasma concentration during the night ("C-ave-night", defined as the average night time amantadine plasma concentration as measured in a human PK study). In some embodiments, the ratio of C-ave-day/C-ave-night at steady state is within one of the ranges 1.3 to 1.9, 1.3 to 1.8, 1.3 to 1.7, 1.3 to 1.6, 1.4 to 1.9, 1.4 to 1.8, 1.4 to 1.7, 1.5 to 1.9, 1.5 to 1.8, 1.5 to 1.7, or 1.6 to 1.9. In some embodiments, the ratio of C-ave-day/C-ave-night at steady state is 1.3, 1.35, 1.4, 1.45, 1.5, 1.55, 1.6, 1.65, 1.7, 1.75, 1.8, 1.85, or 1.9. In some embodiments, the C-ave-day is the average amantadine plasma concentration as measured between the hours of 5 am, 6 am, 7 am, 8 am or 9 am to the hours of 4 pm, 5 pm, 6 pm, 7 pm or 8 pm and the C-ave-night is the average amantadine plasma concentration as measured between the hours of 4 pm, 5 pm, 6 pm, 7 pm, 8 pm, 9 pm, 10 pm or 11 pm to the hours of 5 am, 6 am, 7 am, 8 am or 9 am. In some embodiments, the C-ave-day is the average amantadine plasma concentration as measured within any four to twelve hour period between the hours of 5 am and 8 pm; and the C-ave-night is the average amantadine plasma concentration as measured within any four to twelve hour period between the hours of 8 pm and 5 am. In some embodiments, the C-ave-day is the average amantadine plasma concentration as measured within any four, five, six, seven, eight, nine, ten, eleven or twelve hour period between the hours of 5 am and 8 pm; and the C-ave-night is the average amantadine plasma concentration as measured within any four, five, six, seven, eight, nine, ten, eleven or twelve hour period between the hours of 8 pm and 5 am.

In some embodiments described herein an amantadine composition is administered to a patient from 0 to 4 hours prior to bedtime. In some embodiments, the amantadine composition is administered to a patient from 0 to 3, 0 to 2, or 0 to 1 hours prior to bedtime. In some embodiments, the amantadine composition is administered to a patient from 0 to 240 minutes, from 0 to 180 minutes, e.g., from 0 to 120 minutes, from 0 to 60 minutes, from 0 to 45 minutes, from 0 to 30 minutes, from 0 to 15 minutes or from 0 to 10 minutes prior to bedtime. In some embodiments, the amantadine composition is administered to a patient from 60 to 240 minutes, from 60 to 180 minutes, from 60 to 120 minutes or from 60 to 90 minutes prior to bedtime.

It is to be understood that administration to a patient includes administration by a healthcare professional and self-administration by the patient.

Unless otherwise specified herein, the term "bedtime" has the normal meaning of a time when a person retires for the primary sleep period during a twenty-four hour period of time. While for the general populace, bedtime occurs at night, there are patients, such as those who work nights, for whom bedtime occurs during the day. Thus, in some embodiments, bedtime may be anytime during the day or night.

As used herein, unless otherwise indicated, reference to a plasma concentration profile or a specific pharmacokinetic property (e.g., Cmax, Cmin, AUC, T max, etc.) in a human subject refers to a mean value obtained from healthy adults determined in a typical phase I clinical trial designed to measure pharmacokinetic properties of a drug (see e.g., Examples 2 and 3, below). References herein to T max and $T_{1/2}$ refer to values obtained after administration of a single dose at fasted states, unless otherwise indicated.

As described herein, the unit doses of the amantadine administered in accordance with the present invention are generally higher than the ranges normally prescribed for immediate release compositions of amantadine. For example, the recommended dose of amantadine for the treatment of Parkinson's disease is 100 mg immediate release amantadine administered twice daily. In limited cases of the patient not deriving sufficient benefit at that dose and subject to the patient being able to tolerate such higher dose, the daily dose may be increased to 300 mg or 400 mg, which is always administered in divided doses. Prior to the current invention, the most commonly prescribed dose of amantadine is 200 mg per day, always administered in divided doses. Prior to the current invention, more than 200 mg (for example 300 mg) was always given in divided doses. For the present invention, doses of 260 to 420 mg are administered for treatment of Parkinson's patients, and the methods and compositions of the invention may comprise once-nightly administration of a dose as defined by any of these ranges, particularly at doses from 260 mg to 420 mg, and most preferably 340 mg, once nightly. In some such embodiments the administration of such higher doses is at night, i.e., after 4 p.m. and/or within 4 hours of bedtime. In additional embodiments the administration of such higher doses may be in the form of 1, 2 or 3 capsules of size 0, 1 or 2 in the normal or EL format administered once nightly.

In some embodiments of any of the above aspects the amantadine is administered as a pharmaceutically acceptable salt. In a more specific embodiment, the amantadine is administered as amantadine hydrochloride or amantadine sulfate.

In some embodiment of any of the above aspects, a total daily dose of 260 mg to 420 mg is administered as a once nightly formulation after 4 p.m. and/or within 4 hours of bedtime. In some embodiments, the once nightly dose of amantadine or pharmaceutically acceptable salt thereof administered exceeds 300 mg per day. In various specific embodiments, the once nightly dose of amantadine or pharmaceutically acceptable salt thereof may be 260 to 275 mg, 270 to 285 mg, 280 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, or 410 to 420 mg. In some preferred embodiments, the once nightly dose of amantadine or pharmaceutically acceptable salt thereof is 260 mg to 360 mg, 300 to 360 mg, 330 to 350 mg or 340 mg.

In some embodiments of any of the above aspects, the once nightly composition of amantadine or pharmaceutically acceptable salt thereof comprises from about 260 mg, 265 mg, 270 mg, 275 mg, 280 mg, 285 mg, 290 mg, 295 mg, or 300 mg of amantadine, or a pharmaceutically acceptable salt thereof to about 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, or 420 mg of amantadine, or a pharmaceutically acceptable salt thereof.

In specific embodiments described herein, a subject's entire daily dose of amantadine is administered once, during a period of less than about four, three, two or one hours before bedtime (i.e., after 4 p.m. and/or the time at which the subject wishes to go to sleep for the night).

In some embodiments of any of the above aspects, administration of the composition to a Parkinson's disease patient results in a significant reduction in Parkinson's disease symptoms. In some specific embodiments, administration of the composition results in about 5%, 10%, 15%, 20%, 25%, 30%, 35%, or 40% reduction in Parkinson's symptoms or motor fluctuations. In further specific embodiments, the reduction in Parkinson's symptoms or motor fluctuations is measured on a numerical scale used by or accepted by the FDA or other regulatory agencies to evaluate the effectiveness of and to approve for licensure drugs for the treatment of Parkinson's symptoms or motor fluctuations. In further specific embodiments, the scale used in measuring the reduction in Parkinson's symptoms motor fluctuations could be the Unified Parkinson's Disease Rating Scale (UPDRS). Unified Parkinson's Disease Rating Scale (UPDRS, MDS revision)—Part I: non-motor aspects of experiences of daily living (13 items),—Part II: motor aspects of experiences of daily living (13 items)—Part III: motor examination (33 scored items), Hoehn and Yahr Staging Scale (Original or Modified), or PD Home Diary: total ON time or total OFF time.

In some embodiments of any of the above aspects, administration of the composition to a Parkinson's disease patient results in a significant reduction in levodopa induced dyskinesia. In a specific embodiment, administration of the composition results in about 5%, 10%, 15%, 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by or accepted by the FDA or other regulatory agencies to evaluate effectiveness of and to approve for licensure drugs for the treatment of LID. In further specific embodiments, the scale used in measuring the reduction in LID could be UDysRS, UPDRS Part IV (subscores 32, 33), MDS-UPDRS Part IV, total and items 4.1 and 4.2, Dyskinesia Rating Scale (DRS), Abnormal Involuntary Movement Scale (AIMS), Rush Dyskinesia Rating Scale, Parkinson Disease Dyskinesia Scale (PDYS-26), Obeso Dyskinesia Rating Scale (CAPIT), Clinical Dyskinesia Rating Scale (CDRS), Lang-Fahn Activities of Daily Living Dyskinesia or other scales developed for this purpose. In other specific embodiments, the reduction in LID is measured relative to placebo in a controlled clinical trial. In other embodiments, the reduction in LID is measured relative to baseline in a controlled clinical trial.

In some embodiments of any of the above aspects, administration of the composition to a Parkinson's disease patients results in a significant reduction in Parkinson's disease fatigue. In a specific embodiment, administration of the composition results in about 5%, 10%, 15%, 20%, 25%, 30%, 35%, or 40%, 45%, 50%, 55%, or 60% reduction in Parkinson's disease fatigue. In further specific embodiments, the reduction fatigue is measured on a numeric scale that is used by or accepted by the FDA or other regulatory agencies to evaluate the effectiveness of and to approve for licensure drugs for the treatment of fatigue. In further specific embodiments, the scale used in measuring the reduction in fatigue could be the Fatigue Severity Scale (FSS), Fatigue Assessment Inventory, Functional Assessment of Chronic Illness Therapy-Fatigue (FACIT Fatigue), Multidimensional Fatigue Inventory (MFI-20), Parkinson Fatigue Scale (PFS-16) and the Fatigue Severity Inventory. In other specific embodiments, the reduction in fatigue is measured relative to placebo in a controlled clinical trial. In other embodiments, the reduction in fatigue is measured relative to baseline in a controlled clinical trial.

In some embodiments of any of the above aspects, administration of the composition to patients results in a significant improvement in clinicians overall impression. In some specific embodiments, administration of the composition results in about a 0.5, 1.0, 1.5, 2.0, 2.5 or 3.0 point improvement in clinicians overall impression using a 7 point scale (or proportionate changes using a different scale). In further specific embodiments, the improvement in clinicians overall impression is measured on a numeric scale that is used by or accepted by the FDA or other regulatory agencies to evaluate the effectiveness of and to approve for licensure drugs indicated for patients with Parkinson's disease. In further specific embodiments, the scale used in measuring the improvement in clinicians overall impression could be the Clinicians Global Impression of Change Rating Scale (CGIC). In other specific embodiments, the improvement in clinicians overall impression is measured relative to placebo in a controlled clinical trial. In other embodiments, the improvement in clinicians overall impression is measured relative to baseline in a controlled clinical trial.

Extended Release Formulations

Extended release amantadine compositions suitable for use in the method of the invention can be made using a variety of extended release technologies, such as those described in the patent publications referenced in the above background section, which publications are incorporated herein by reference in their entireties. In some embodiments, the invention is a pellet in capsule dosage form. In some embodiments, the pellets comprise a pellet core, which is coated with at least one drug layer and at least one extended release coating layer. In some embodiments, the pellets are coated with at least one drug layer, an intermediate layer such as a seal coat and an extended release coating layer. In some embodiments, the pellet, the drug layer or both comprise one or more binders.

In some embodiments, the dosage unit comprises a plurality of coated pellets. In some embodiments, the pellets have a diameter of for example 300 to 1700 microns, in some cases 500 to 1200 microns. The pellets will comprise, for example, inert substrates, such as sugar spheres, microcrystalline cellulose (MCC) spheres, starch pellets. In some embodiments, pellets can be prepared by other processes such as pelletization, extrusion, spheronization, etc. or combinations thereof. The core pellets will comprise of amantadine hydrochloride and pharmaceutically acceptable excipients.

Coated Pellets

The pellet cores are coated with the active ingredient, e.g., amantadine or a pharmaceutically acceptable salt and/or polymorph thereof. In some embodiments, in addition to the active ingredient, the pellets also comprise one or more binders, such as for example hydroxypropyl methyl cellulose, copovidone, povidone, hydroxypropyl cellulose, hydroxyethyl cellulose, methyl cellulose, carboxymethyl cellulose etc. In some embodiments, the pellets also contain one or more additional excipients, such as anti-tack agents (e.g. talc, magnesium stearate etc.)

In some embodiments, the pellets cores are coated with a drug layer comprising active ingredient, and optionally one or more binders, anti-tack agents and/or solvents by conventional coating techniques such as fluidized bed coating, pan coating.

Intermediate Layer Coating

In some embodiments, the pellets are coated with an intermediate layer, such as a seal coat. In some embodiments, the seal coat is adapted to prevent ingredients in the extended release coating from interacting with ingredients in the pellet core, to prevent migration of the ingredients in the pellet core from diffusing out of the pellet core into the extended release layer, etc. As described herein, the seal coat of the present invention can comprise one or more film forming polymers including but not limited to hydroxypropylmethyl cellulose (HPMC), copovidone, povidone, polyvinyl pyrrolidone, hydroxypropyl cellulose, hydroxyethyl cellulose, methyl cellulose, carboxymethyl cellulose or any combination thereof and the like.

The seal coat can further comprise other additives like plasticizers, such as, propylene glycol, triacetin, polyethylene glycol, tributyl citrate and optionally anti-tacking agents, such as, magnesium stearate, calcium silicate, magnesium silicate, and colloidal silicon dioxide or talc.

Apart from plasticizers and anti-tacking agents as mentioned above, the seal coat can optionally contain buffers, colorants, opacifiers, surfactants or bases, which are known to those skilled in the art.

Seal coating can be applied to the core using conventional coating techniques such as fluidized bed coating, pan coating etc. In some embodiments, the drug coated pellets cores are coated with a seal coat layer that optionally comprises one or more binders, anti-tack agents and/or solvents by fluidized bed coating or pan coating.

Binders

In some embodiments, the pellet cores, the intermediate coating layer, or both may comprise one or more binders (e.g., film forming polymers). Suitable binders for use herein include, e.g.: alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Extended Release Coating

The pellets are coated with an extended release coating. The extended release coating is adapted to delay release of the drug from the coated drug cores for a period of time after introduction of the dosage form into the use environment. In some embodiments, the extended release coating includes one or more pH-dependent or non-pH-dependent extended release excipients. Examples of non-pH dependent extended release polymers include ethyl cellulose, hydroxypropylmethyl cellulose, hydroxyethyl cellulose, hydroxypropyl cellulose, carboxymethyl cellulose, copolymer of ethyl acrylate, methyl methacrylate (e.g., Eudragit RS) etc. Examples of pH dependent extended release excipients include methacrylic acid copolymers, hydroxypropylmethyl cellulose acetate succinate, hydroxypropylmethyl cellulose phthalate, and cellulose acetate phthalate etc. The extended release coating may also include a pore former, such as povidone, polyethylene glycol, hydroxypropyl cellulose, hydroxypropylmethyl cellulose, etc., sugars such as sucrose, mannitol, lactose, and salts, such as sodium chloride, sodium citrate, etc., a plasticizer, such as acetylated citrated esters, acetylated glycerides, castor oil, citrate esters, dibutylsebacate, glyceryl monostearate, diethyl phthalate, glycerol, medium chain triglycerides, propylene glycol, polyethylene glycol. The extended release coating may also include one or more additional excipients, such as lubricants (e.g., magnesium stearate, talc etc.).

Extended release coating can be applied using conventional coating techniques such as fluidized bed coating, pan coating etc. The drug coated pellets cores, which optionally comprise a seal coat, are coated with the extended release coating by fluidized bed coating.

Extended Release Excipients (Coating Polymers)

As described herein, exemplary extended release excipients include, but are not limited to, insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl celluloses such as hydroxypropyl cellulose, hydroxypropylmethyl cellulose, sodium carboxymethyl cellulose, and cross-linked acrylic acid polymers like Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material can be a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain other embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In still other embodiments, the acrylic polymer is an acrylic resin lacquer such as that which is commercially available from Rohm Pharma under the trade name Eudragit®. In further embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit RL30D and 1:40 in Eudragit® RS30D. The mean molecular weight is about 150,000. Eudragit® S-100 and Eudragit® L-100 are also suitable for use herein. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain an extended release formulation having a desirable dissolution profile. One skilled in the art will recognize that other acrylic polymers may also be used, such as, for example, Eudragit® L.

Pore Formers

In some embodiments, the extended release coating includes a pore former. Pore formers suitable for use in the extended release coating can be organic or inorganic agents, and include materials that can be dissolved, extracted or leached from the coating in the environment of use. Examples of pore formers include but are not limited to organic compounds such as mono-, oligo-, and polysaccharides including sucrose, glucose, fructose, mannitol, mannose, galactose, lactose, sorbitol, pullulan, dextran; polymers soluble in the environment of use such as water-soluble hydrophilic polymers, such as povidone, crospovidone, polyethylene glycol, hydroxypropyl cellulose, hydroxypropylmethyl cellulose, hydroxyalkyl celluloses, carboxyalkyl celluloses, cellulose ethers, acrylic resins, polyvinylpyrrolidone, cross-linked polyvinylpyrrolidone, polyethylene oxide, carbowaxes, Carbopol®, and the like, diols, polyols, polyhydric alcohols, polyalkylene glycols, polyethylene glycols, polypropylene glycols, or block polymers thereof, polyglycols, poly($\alpha$-$\Omega$) alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like. In certain embodiments, plasticizers can also be used as a pore former.

Capsules

The extended release pellets may be introduced into a suitable capsule by using an encapsulator equipped with pellet dosing chamber. The capsule sizes may be 00, 0, 0EL, 1, 1EL, 2, 2EL, 3, 4 or 5. A particularly preferred composition that provides ideal pharmacokinetic properties and plasma concentration profiles is a pellet-in-capsule composition that comprises a plurality of pellets, typically having a diameter of about 500 µm to 1.2 mm, and preferably about 700 µm to 1000 µm, where each pellet comprises a core comprising amantadine and a binder, and an extended release coating surrounding the core that extends release of the amantadine so as to provide the desired pharmacokinetic properties and amantadine plasma concentration profiles described above.

In some embodiments, the pellets in the pellet-in-capsule are in a size 0 or smaller, preferably a size 1 or smaller capsule. Mean pellet diameters in some embodiments may be in a range of 500 µm to 1200 µm, e.g., from 500 µm to 1100 µm, from 500 µm to 1000 µm, from 500 µm to 900 µm, from 500 µm to 800 µm, from 500 µm to 700 µm, from 600 µm to 1100 µm, from 600 µm to 1000 µm, from 600 µm to 900 µm, from 600 µm to 800 µm, from 600 µm to 700 µm, from 700 µm to 1100 µm, from 700 µm to 1000 µm, from 700 µm to 900 µm, or from 700 µm to 800 µm. In some embodiments the mean particle diameters are, ±10%, e.g.: 500 µm, 550 µm, 600 µm, 650 µm, 700 µm, 750 µm, 800 µm, 850 µm, 900 µm, 950 µm, 1000 µm, 1050 µm, 1100 µm, 1150 µm or 1200 µm.

One preferred composition of the invention is a pellet-in-capsule composition wherein each pellet comprises a core that comprises a core seed with a mixture of amantadine and a binder coated onto the core seed, and an extended release coating surrounding the core comprising ethyl cellulose, a pore forming agent such as hydroxypropyl methyl cellulose or povidone, and a plasticizer. In some embodiments, the pellets may further comprise a seal coating between the pellet core and the extended release coating. The pellets are formulated using methods known in the art, such as those described in Example 1 below. In a specific embodiment, based on the combined weight of the pellet core and extended release coating, the amantadine is present in amounts from 20-80 wt %, 45-70 wt %, 40-50 wt %, 45-55 wt %, 50-60 wt %, 55-65 wt %, 60-70 wt %, 65-75 wt %, 70-80 wt %, or 40 to 60 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g., Celphere®), is present in amounts from 8 to 25 wt %, the ethyl cellulose is present in amounts from 10 to 20 wt %, the pore forming agent, preferably povidone, is present in amounts from 1 to 4 wt %, and the plasticizer is present in amounts from 1 to 4 wt %. In another specific embodiment, based on the combined weight of the pellet core and extended release coating, the amantadine is present in amounts from 50 to 70 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g., Celphere®), is present in amounts from 5 to 15 wt %, the ethyl cellulose is present in amounts from 1 to 15 wt %, the pore forming agent, preferably povidone, is present in amounts from 0.25 to 4 wt %, and the plasticizer is present in amounts from 0.25 to 4 wt %.

Additional embodiments of the invention are illustrated in the Table 1, below, entitled "Various Amantadine ER Capsule Size 1 Formulations". By means of methods and compositions described herein, formulations can be made that achieve the desired dissolution characteristics and target pharmacokinetic profiles described herein. More specifically, therapeutically effective doses of amantadine can be administered once nightly in no more than two size 1 (or smaller, e.g., size 2 or 3) capsules using the manufacturing methods and compositions that have been described herein to achieve these results. In particular, higher drug loading can be achieved using compositions and manufacturing methods described herein. In some embodiments, higher drug loading may be achieved, with the required dissolution profile, using smaller core pellet sizes and concomitantly increased drug layering on smaller cores, but with no change in the extended release coat. In some embodiments, using alternative manufacturing approaches described herein, e.g., extrusion and spheronization, even higher drug loads can be achieved to realize the desired dissolution profile, enabling high amantadine drug loads with suitable pharmacokinetic profiles, resulting in compositions that are therapeutically more effective, and at least as well tolerated, and can be filled in relatively small sized capsules (e.g., size 1, 2 or 3), enabling ease of administration to patients.

TABLE 1

Various Amantadine ER Capsule Size 1 Formulations

| AMT Strength (mg) | Manufacture Method | Inert Core Pellet Size (mm) | Active Drug % w/w | Extended Release Coating % w/w | Bulk Density (g/cm³) | % Fill in Size 1 Capsule |
|---|---|---|---|---|---|---|
| 85 mg | Fluid bed coating | 0.3-0.5 | 40-50% | 10-30% | 0.6-1.0 | 60-70% |
| 110 mg | Fluid bed coating | 0.3-0.5 | 40-50% | 10-30% | 0.6-1.0 | 60-70% |
| 140 mg | Fluid bed coating | 0.3-0.5 | 45-50% | 10-30% | 0.6-1.0 | 80-90% |
| 150 mg | Fluid bed coating | 0.3-0.5 | 50-55% | 10-30% | 0.6-1.0 | 80-90% |
| 170 mg | Fluid bed coating | 0.2-0.3 | 50-55% | 10-30% | 0.6-1.0 | 80-90% |
| 170 mg | Extrusion spheronization, pan or fluidized bed coating | N/A | 55-75% | 10-30% | 0.6-1.0 | 65-75% |
| 190 mg | Extrusion spheronization, pan or fluidized bed coating | N/A | 55-75% | 10-30% | 0.6-1.0 | 75-85% |
| 210 mg | Extrusion spheronization, pan or fluidized bed coating | N/A | 55-75% | 10-30% | 0.6-1.0 | 80-90% |
| 230 mg | Extrusion spheronization, pan or fluidized bed coating | N/A | 55-75% | 10-30% | 0.6-1.0 | 85-95% |

Suitable plasticizers include medium chain triglycerides, diethyl phthalate, citrate esters, polyethylene glycol, glycerol, acetylated glycerides, castor oil, and the like. The pellets are filled into capsules to provide the desired strength of amantadine. An advantage of this composition is it provides the desired release properties that make the composition suitable for administration during said period before bedtime. A further advantage is that the extended release coating is sufficiently durable so that the capsule can be opened and the pellets sprinkled onto food for administration to patients who have difficulty swallowing pills, without adversely affecting the release properties of the composition. When the composition is administered by sprinkling onto food, it is preferred to use a soft food such as applesauce or chocolate pudding, which is consumed within 30 minutes, and preferably within 15 minutes. A yet further advantage of the above-described composition is that it has very good batch-to-batch reproducibility and shelf-life stability.

A preferred pellet-in-capsule composition of the invention, in addition to having the above in vitro dissolution properties and any of the above-described pharmacokinetic properties (e.g., in vivo release profile, T max, Cmax/Cmin ratio, etc) that make the composition suitable for administration in said period before bedtime. The composition is further characterized by providing a Cmax of 1.6-2.4 ng/ml per mg of amantadine and an $AUC_{0-inf}$ of 40-75 ng*h/mL per mg of amantadine after oral administration of a single dose of the capsule to a human subject in a fasted state. A preferred pellet-in-capsule composition is further characterized by a steady state plasma concentration in which once nightly oral administration of the capsule to a human subject provides a Cmax of 2.4 to 4.2 ng/ml per mg of amantadine, a Cmin of 1.1 to 2.6 ng/ml per mg of amantadine, and an $AUC_{0-24}$ of 48-73 ng*h/mL per mg of amantadine.

The above-described pellet-in-capsule compositions may be provided at a strength suitable for amantadine therapy. Typical strengths range from at least about 50 mg to about 250 mg. In a specific embodiment, the capsule strength is 70 mg, 80 mg, 85 mg, 90 mg, 110 mg, 120 mg, 125 mg, 130 mg, 140 mg, 150 mg, 160 mg, 160 mg, 170 mg, 180 mg, 190 mg, 210 mg, and 220 mg, that provides a single dose $AUC_{0\text{-}inf}$ per mg that is equivalent to a 100 mg tablet of an immediate release formulation of amantadine HCl (e.g., Symmetrel®, or other FDA Orange Book reference listed drug). One, two, or three, of such capsules can be administered to a subject in the period before bedtime. In a preferred embodiment, between 220 mg and 650 mg of amantadine is adminstered using 2 capsules of a suitable ER formulations once nightly.

Other Extended Release Dosage Forms

The person of skill in the art will recognize that other embodiments of extended release compositions may be envisioned, in addition to the capsule formulation described above. Such other embodiments include extended release solid dosage forms, such as tablets, capsules, gel caps, powders, pellets, beadlets, etc. Included in such extended release compositions are those that have the release characteristics and in vivo pharmacokinetic profile to be employed in the methods of the invention. In some embodiments, the person skilled in the art may employ, with appropriate adjustment of design characteristics to achieve the necessary pharmacokinetic profile described herein, the extended release technology described in U.S. Pat. No. 5,358,721, to Guittard et al., or U.S. Pat. No. 6,217,905, to Edgren et al., each of which disclose an oral osmotic dosage form of amantadine, and each of which is incorporated herein by reference in its entirety. In other embodiments, the person of skill in the art may employ, again with appropriate adjustment of design characteristics, the technology described in U.S. Pat. No. 6,194,000, to Smith et al. or U.S. Patent Appl. Publication Nos. US 2006/0252788, US 2006/0189694, US 2006/0142398, US 2008/0227743 and US2011/0189273, all to Went et al., each of which disclose the administration of an NMDA receptor antagonist, such as amantadine, optionally in controlled release form, and each of which is incorporated herein by reference in its entirety.

Aspects of the invention may also be described in terms of the following numbered embodiments:

1. A method of increasing ON time without dyskinesia in a patient with Parkinson's disease (PD), comprising administering to said patient once daily a composition comprising 260 to 420 mg amantadine, or a pharmaceutically acceptable salt thereof, and at least one release modifying excipient.
2. 2. A method of reducing ON time with dyskinesia in a patient with Parkinson's disease (PD), comprising administering to said patient once daily a composition comprising 260 to 420 mg amantadine, or a pharmaceutically acceptable salt thereof, and at least one release modifying excipient.
3. A method of reducing ON time with troublesome dyskinesia in a patient with Parkinson's disease (PD), comprising administering to said patient once daily a composition comprising 260 to 420 mg amantadine, or a pharmaceutically acceptable salt thereof, and at least one release modifying excipient.
4. A method of increasing ON time without troublesome dyskinesia and without increasing sleep disturbances in a patient with Parkinson's disease (PD), comprising administering to said patient once daily a composition comprising 260 to 420 mg amantadine, or a pharmaceutically acceptable salt thereof, and at least one release modifying excipient.
5. A method of reducing OFF time in a patient with Parkinson's disease (PD), comprising administering to said patient once daily a composition comprising 260 to 340 mg amantadine, or a pharmaceutically acceptable salt thereof, and at least one release modifying excipient.
6. A method of improving CGI in a patient with a CNS disorder, comprising administering to said patient once daily a composition comprising 260 to 420 mg amantadine, or a pharmaceutically acceptable salt thereof, and at least one release modifying excipient.
7. A method of achieving any two results selected from the group consisting of (A) increasing ON time without troublesome dyskinesia, (B) reducing OFF time, and (C) improving CGI, in a patient with a CNS disorder, comprising administering to said patient once daily a composition comprising 260 to 420 mg amantadine, or a pharmaceutically acceptable salt thereof, and at least one release modifying excipient.
8. A method of (A) increasing ON time without troublesome dyskinesia and (B) reducing OFF time in a patient with a CNS disorder, comprising administering to said patient once daily a composition comprising 260 to 340 mg amantadine, or a pharmaceutically acceptable salt thereof, and at least one release modifying excipient.
9. A method of (A) increasing ON time without troublesome dyskinesia and (B) improving CGI in a patient with a CNS disorder, comprising administering to said patient once daily a composition comprising 260 to 420 mg amantadine, or a pharmaceutically acceptable salt thereof, and at least one release modifying excipient.
10. A method of (A) reducing OFF time and (B) improving CGI in a patient with a CNS disorder, comprising administering to said patient once daily a composition comprising 260 to 340 mg amantadine, or a pharmaceutically acceptable salt thereof, and at least one release modifying excipient.
11. A method comprising administering once daily 260 to 340 mg dose of amantadine, or a pharmaceutically acceptable salt thereof, to a patient in need thereof without increasing insomnia.
12. A method comprising administering once daily 260 to 340 mg dose of amantadine, or a pharmaceutically acceptable salt thereof, to a patient in need thereof without increasing sleep disturbance.
13. The method of one of embodiments 1-4, 6, 7, and 9, wherein the composition comprises 260 to 340 mg amantadine, or a pharmaceutically acceptable salt thereof
14. The method of one of embodiments 1-12, wherein the composition comprises 260 mg amantadine, or a pharmaceutically acceptable salt thereof
15. The method of one of embodiments 1-12, wherein the composition comprises 340 mg amantadine, or a pharmaceutically acceptable salt thereof
16. The method of one of embodiments 1-10, wherein the method does not increase insomnia.
17. The method of one of embodiments 1-3 or 5-10, wherein the method does not increase sleep disturbance.
18. A method of administering once daily a dosage form comprising a therapeutically effective amount of a drug selected from the group consisting of amantadine and a pharmaceutically acceptable salt thereof, and at least one release modifying excipient to a patient in need thereof, wherein said method comprises administering to said patient a reduced amount of the drug once daily for a period of at least one week immediately preceding the once daily administration of the dosage form comprising a therapeutically effective amount of the drug.

19. The method of embodiment 18, wherein the therapeutically effective amount of drug comprises 260 to 420 mg amantadine, or a pharmaceutically acceptable salt thereof 20. The method of embodiment 18, wherein the therapeutically effective amount of drug comprises 260 to 340 mg amantadine, or a pharmaceutically acceptable salt thereof 21. The method of embodiment 18, wherein the therapeutically effective amount of drug comprises 260 mg amantadine, or a pharmaceutically acceptable salt thereof 22. The method of embodiment 18, wherein the therapeutically effective amount of drug comprises 340 mg amantadine, or a pharmaceutically acceptable salt thereof 23. The method of one of embodiments 1-12 or embodiment 18, wherein the composition is administered 0 to 4 hours before bedtime.

24. The method of one of embodiments 1-12 or embodiment 18, wherein the C-ave-day is 1.4 to 1.7 times the C-ave-night.

25. The method of one of embodiments 1-12 or embodiment 18, wherein administration of a single dose of the composition to a cohort or human healthy volunteer subjects in a fasted state provides an average Cmax of 1.1 to 1.7 ng/ml per mg of amantadine or an $AUC_{0-inf}$ of 46 to 56 ng*h/mL per mg of amantadine.

26. The method of one of embodiments 1-12 or embodiment 18, wherein once daily oral administration of a dose of the composition to a cohort of human subjects provides a steady state plasma concentration profile characterized by at least one of: (i) a mean Cmax of 2.2 to 2.7 ng/ml per mg of amantadine, (ii) a mean Cmin of 1.4 to 1.7 ng/ml per mg of amantadine, and (iii) a mean $AUC_{0-24}$ of 46 to 56 ng*h/mL per mg of amantadine.

27. The method of embodiment 1, wherein the change in ON time without dyskinesia is determined in a placebo controlled, double blind clinical study using the PD Home diary.

28. The method of embodiment 2, wherein the change in ON time with dyskinesia is determined in a placebo controlled, double blind clinical study using the PD Home diary.

29. 29. The method of embodiment 3, wherein the change in ON time with troublesome dyskinesia is determined in a placebo controlled, double blind clinical study using the PD Home diary.

30. The method of one of embodiments 4, 7, 8, or 9, wherein the change in ON time without troublesome dyskinesia is determined in a placebo controlled, double blind clinical study using the PD Home diary.

31. The method of one of embodiments 5, 7, 8, or 10, wherein the change in OFF time is determined in a placebo controlled, double blind clinical study using the PD Home diary.

32. The method of one of embodiments 6, 7, 9, or 10, wherein the improvement in CGI is determined in a placebo controlled, double blind clinical study.

33. Use of amantadine, or a pharmaceutically acceptable salt thereof, in the manufacture of a medicament for the treatment of a disease mediated by the NMDA receptor to a subject in need thereof, said medicament being an extended release (ER) composition, and said treatment comprising orally administering said composition less than three hours before bedtime (i.e. the time at which the subject wishes to go to sleep for the night).

34. Use of amantadine, or a pharmaceutically acceptable salt thereof, in the manufacture of a medicament for reducing sleep disturbance in a human subject undergoing treatment with amantadine, said medicament being an extended release (ER) composition and being adapted for administration less than three hours before bedtime (i.e. the time at which the patient wishes to go to sleep for the night).

35. The use or composition of any one of embodiments 33-34 wherein administration occurs less than 1 hour before bedtime.

36. The use or composition of any one of embodiments 33-35, wherein the patient has been diagnosed with Parkinson's disease.

37. The use or composition of any one of embodiments 33-36, wherein the composition is administered once nightly.

38. The use or composition of any one of embodiments 33-37, wherein the composition is added to food prior to administration.

39. The use or composition of any one of embodiments 33-38, wherein there is no increase in plasma concentration of amantadine for at least one hour after the administration at steady state.

40. The use or composition of any one of embodiments 33-39, wherein there is no increase in plasma concentration of amantadine for at least two hours after the administration at steady state.

41. The use of composition of any one of embodiments 33-40, wherein, the amantadine has a single dose T max of 9 to 18 hours and/or a steady state T max of 7 to 13 hours after administration.

42. The use or composition of any one of embodiments 33-41, wherein the amantadine has a single dose T max of 12 to 18 hours after administration, and/or a steady state T max of 8 to 12 hours after administration.

43. The use or composition of any one of embodiments 33-42, wherein a once nightly oral administration of the composition to a human subject provides a steady state plasma concentration profile characterized by a concentration increase of amantadine of less than 25% at three hours after the administration.

44. The use or composition of any one of embodiments 33-43 having a Cmax/Cmin ratio of 1.3 to 1.8.

45. The use or composition of any one of embodiments 33-43 having a Cmax/Cmin ratio of 1.4 to 1.7.

46. The use or composition of any one of embodiments 33-45, wherein the amantadine is amantadine hydrochloride or amantadine sulfate.

47. The use or composition of any one of embodiments 33-46 wherein the composition comprises 260 to 420 mg of amantadine, or a pharmaceutically acceptable salt thereof 48. The use or composition of embodiment 47, wherein the composition is administered as one, two, or three or four unit dosage forms each comprising 85 to 175 mg amantadine, or a pharmaceutically acceptable salt thereof 49. The use or composition of any one of embodiments 33-48 wherein the composition comprises 260 to 420 mg of amantadine, or a pharmaceutically acceptable salt thereof 50. The use or composition of embodiment 49, wherein the composition is administered as two unit dosage forms each comprising 85 to 175 mg amantadine, or a pharmaceutically acceptable salt thereof 51. The use or composition of any one of embodiments 33 to 50, wherein the composition comprises 50 to 200 mg amantadine or a pharmaceutically acceptable salt thereof 52. The use or composition of any one of embodiments 33-51, wherein oral administration of a single dose of the composition to a human subject in a fasted state provides a maximum plasma concentration (Cmax) of amantadine of 1.1 to 1.7 ng/ml per mg of amantadine and an $AUC_{0-inf}$ of 46 to 56 ng*h/mL per mg of amantadine.

53. The use or composition of any one of embodiments 33-52, wherein once daily oral administration of a dose of the composition to a human subject (or to a healthy human subject population) provides a steady state plasma amantadine concentration profile characterized by:
    (i) a Cmax of 2.2 to 2.7 ng/ml per mg of amantadine,
    (ii) a Cmin of 1.4 to 1.7 ng/ml per mg of amantadine, and
    (iii) an $AUC_{0-24}$ of 46 to 56 ng*h/mL per mg of amantadine.

54. The use or composition of embodiment 53, wherein the steady state plasma concentration profile is further characterized by:
    (iv) no increase in plasma concentration of amantadine for at least one hour after the administration; and
    (v) a Cmax/Cmin ratio of 1.4 to 1.7.

55. The use or composition of embodiment 53, wherein the steady state plasma concentration profile is further characterized by:
    (iv) no increase in concentration of amantadine for at least two hours after the administration; and
    (v) a Cmax/Cmin ratio of 1.4 to 1.7.

56. The use of any one of embodiments 33-55, wherein the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$.

57. The use of any one of embodiments 33-56, wherein the composition has an AUC profile after once daily dosing of the composition at steady state conditions characterized by: a fractional AUC from 0 to 4 hours that is about 2 to 25% of $AUC_{24}$; a fractional AUC from 0 to 8 hours that is about 15 to 50% of $AUC_{24}$; a fractional AUC from 0 to 12 hours that is about 30 to 70% of $AUC_{24}$: and a fractional AUC from 0 to 18 hours that is about 60 to 95% of $AUC_{24}$.

58. The use or composition of any one of embodiments 33 to 57, for use in a method of treating Parkinson's disease in a human subject in need thereof, said method comprising orally administering said composition.

59. The use or composition of any of the above enumerated embodiments, in which the composition or use achieves an increase in ON time without dyskinesia (e.g., as determined in a placebo controlled, double blind clinical study using the PD Home diary) for a Parkinson's disease patient.

60. The composition or use of embodiment 59, said composition or use comprising 260 to 420 mg amantadine or a pharmaceutically acceptable salt thereof 61. The composition or use of embodiment 59, said composition or use comprising 260 to 340 mg amantadine or a pharmaceutically acceptable salt thereof 62. The composition or use of embodiment 59, said composition or use comprising 340 mg amantadine or a pharmaceutically acceptable salt thereof 63. The composition or use of any of the above enumerated embodiments, in which the composition or use achieves a reduction in ON time with troublesome dyskinesia (e.g., as determined in a placebo controlled, double blind clinical study using the PD Home diary) in a Parkinson's disease patient.

64. The composition or use of embodiment 63, said composition or use comprising 260 to 420 mg amantadine or a pharmaceutically acceptable salt thereof 65. The composition or use of embodiment 63, said composition or use comprising 260 to 340 mg amantadine or a pharmaceutically acceptable salt thereof 66. The composition or use of embodiment 63, said composition or use comprising 340 mg amantadine or a pharmaceutically acceptable salt thereof 67. A composition or use of any of the above enumerated embodiments, in which the composition or use achieves a decrease in OFF time in the Parkinson's disease patient.

68. The composition or use of embodiment 67, said composition or use comprising 260 to 420 mg amantadine or a pharmaceutically acceptable salt thereof 69. The composition or use of embodiment 67, said composition or use comprising 260 to 340 mg amantadine or a pharmaceutically acceptable salt thereof 70. The composition or use of embodiment 67, said composition or use comprising 340 mg amantadine or a pharmaceutically acceptable salt thereof 71. A composition or use of any of the above enumerated embodiments, in which the composition or use achieves an increase in ON time without troublesome dyskinesia (e.g., as determined in a placebo controlled, double blind clinical study using the PD Home diary) and without increasing sleep disturbance in the Parkinson's disease patient.

72. A composition or use of any of the above enumerated embodiments, in which the composition or use achieves a decrease in OFF time for a Parkinson's disease patient.

73. The composition or use of embodiment 72, said composition or use comprising 260 to 420 mg amantadine or a pharmaceutically acceptable salt thereof 74. The composition or use of embodiment 72, said composition or use comprising 260 to 340 mg amantadine or a pharmaceutically acceptable salt thereof 75. The composition or use of embodiment 74, said composition or use comprising 340 mg amantadine or a pharmaceutically acceptable salt thereof.

Some embodiments herein provide a method of once nightly administering amantadine (or a pharmaceutically acceptable salt thereof, such as amantadine hydrochloride) to a subject in need thereof, said method comprising orally administering an extended release (ER) composition comprising amantadine, or a pharmaceutically acceptable salt thereof, less than four hours before bedtime (and/or after 4 p.m.). In some embodiments, administration occurs less than four hours before bedtime. In some such methods, the method increases the ON time without dyskinesia experienced by the Parkinson's disease patient. In some such methods, the method reduces the ON time with dyskinesia experienced by the Parkinson's disease patient. In some such methods, the method reduces the ON time with troublesome dyskinesia experienced by the Parkinson's disease patient. In some embodiments, the method reduces the OFF time experienced by the Parkinson's disease patient. In some embodiments, the method increases ON time without troublesome dyskinesia, and does so without inducing or increasing sleep disturbances in the Parkinson's disease patient. In some embodiments, the method improves clinician global impression, and does so without inducing or increasing sleep disturbances in the patient. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration. In some embodiments, the amantadine has a single dose T max of 9 to 18 hours, and/or a steady state T max of 7 to 13 hours. In some embodiments, the amantadine has a single dose T max of 12 to 18 hours after administration, and/or a steady state T max of 8 to 12 hours. In some embodiments, the amantadine has a single dose T max of 12 to 16 hours after administration, and/or a steady state T max of 9 to 12 hours. In some embodiments, a once nightly oral administration of the composition to a human subject provides a steady state plasma concentration profile characterized by a concentration increase of amantadine of less than 25% at three hours after the administration. In some embodiments, the PK curve has a Cmax/Cmin ratio of 1.4 to 1.7. In some embodiments, the ratio of C-ave-day/C-ave night at steady state is 1.4 to 1.7. In some embodiments, the average amantadine plasma concentration during the day (C-ave-day) at steady state is 500-2000 ng/ml. In some embodiments, the amantadine is amantadine hydrochloride or amantadine sulfate. In some embodiments, the composition comprises 260 to 420 mg of amantadine, or a pharmaceutically acceptable salt thereof. In some embodiments, the composition is administered as two, or three or four unit dosage forms each comprising 85 to 175 mg amantadine, or a pharmaceutically acceptable salt thereof. In some embodiments, the composition is administered as two unit dosage forms each comprising 130 to 210 mg of extended release amantadine, or a pharmaceutically acceptable salt thereof. In some embodiments, the composition is within a capsule of capsule size #1. In some embodiments, the composition comprises 260 mg to 340 mg of amantadine or pharmaceutically acceptable salt thereof. In some embodiments, the composition comprises 340 mg of amantadine or pharmaceutically acceptable salt thereof. In some embodiments, the composition comprises 170 mg amantadine hydrochloride. In some embodiments, oral administration of a single dose of the composition to a human subject in a fasted state provides a maximum plasma concentration (Cmax) of 1.1 to 1.7 ng/ml per mg of amantadine, and an $AUC_{0-inf}$ of 46 to 56 ng*h/mL per mg of amantadine. In some embodiments, once nightly oral administration of a dose of the composition to a human subject provides a steady state plasma concentration profile characterized by: (a) a Cmax of 2.0 to 3.1 ng/ml per mg of amantadine; (b) a Cmin of 1.3 to 2.0 ng/ml per mg of amantadine, and (c) an $AUC_{0-24}$ of 46 to 56 ng*h/mL per mg of amantadine. In some embodiments, the steady state plasma concentration profile is further characterized by: (d) no increase in plasma concentration of amantadine for at least one hour after the administration; and (e) a Cmax/Cmin ratio of 1.4 to 1.7. In some embodiments, the steady state plasma concentration profile is further characterized by: (f) no increase in concentration of amantadine for at least two hours after the administration; and (g) a Cmax/Cmin ratio of 1.4 to 1.7.

In some embodiments, the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$. In some embodiments, the composition has an AUC profile after once nightly dosing of the composition at steady state conditions characterized by: a fractional AUC from 0 to 4 hours that is about 2 to 25% of $AUC_{0-24}$; a fractional AUC from 0 to 8 hours that is about 15 to 50% of $AUC_{0-24}$; a fractional AUC from 0 to 12 hours that is about 30 to 70% of $AUC_{0-24}$; and a fractional AUC from 0 to 18 hours that is about 60 to 95% of $AUC_{0-24}$. In some such embodiments, the method increases ON time without troublesome dyskinesia. In some such embodiments, the method decreases OFF time experienced by a Parkinson's patient.

Some embodiments herein provide a method of reducing sleep disturbance in a human subject undergoing treatment with amantadine, said method comprising once nightly administering an extended release (ER) composition comprising amantadine, or a pharmaceutically acceptable salt thereof, less than four hours before bedtime (and/or after 4 p.m.) In some such methods, the method reduces the ON time the Parkinson's disease patient experiences with dyskinesia. In some such methods, the method reduces the ON time with troublesome dyskinesia experienced by the Parkinson's disease patient. In some embodiments, the method reduces the OFF time the Parkinson's disease patient experiences. In some embodiments, the method increases ON time without troublesome dyskinesia, and does so without inducing or increasing sleep disturbances in the Parkinson's disease patient. In some embodiments, the composition is added to food prior to administration. In some embodiments, there is no increase in plasma concentration of amantadine for at least one hour after the administration. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration.

The present invention may be better understood by reference to the following examples, which are not intended to limit the scope of the claims.

Example 1: Amantadine Extended Release Coated Pellet Formulations

Amantadine HCl extended release coated pellet compositions designed for nighttime administration were prepared using the components and relative amounts shown in Table 3, below. For each composition, the drug coating solution was prepared by adding HPMC 5 cps and Copovidone to isopropyl alcohol with continuous stirring. Purified water was added to this dispersion and stirring continued until a clear solution is formed. Drug (Amantadine HCl) was then added to this binder solution and stirring continued until the drug was completely dissolved. Finally, talc was added and dispersed uniformly by stirring.

Celphere beads (screen sizes #35 to #50 i.e., 300 to 500 micron) were loaded in a Wurster coating unit. The drug coating dispersion was sprayed onto the beads followed by a period of drying. The resulting drug coated pellets were sieved to retain the fraction between screens #18 and #24 (approximately 700 μm to 1 mm diameter).

The seal coating solution was prepared by adding HPMC 5 cps to isopropyl alcohol with continuous stirring. Purified water was added to this dispersion and stirring continued until a clear solution was formed. Talc was added and dispersed uniformly by stirring. The sieved drug coated pellets were loaded in a Wurster coating unit. The seal coating dispersion was sprayed over the drug coated pellets followed by a period of drying to remove the residual solvent and water in the pellets. The resulting seal coated pellets were sieved to retain the fraction between screens #18 and #24.

The ER coating solution was prepared by dissolving ethyl cellulose (viscosity 7 cps) in isopropyl alcohol and purified water and stirring until a clear solution was formed. Povidone K-90 was then dissolved in this clear solution followed by addition of plasticizer Miglyol 812N with continuous stirring to form a clear solution. The sieved seal coated pellets were loaded in a Wurster coating unit. The ER coating solution was sprayed over the seal coated pellets followed by a period of drying to affect the ER coat and remove the residual solvent and water in the pellets. After drying, magnesium stearate was spread on the top bed of the coated pellets in the annulus region followed by recirculation of the pellets in the Wurster unit to blend the magnesium stearate with the coated pellets. The resulting ER coated pellets were sieved to retain the fraction between screens #18 and #24.

The desired weight of the ER coated pellets containing the unit dose were filled into empty 1 hard gelatin capsule shell (size 1 for 60-140 mg strength) using an encapsulator equipped with pellet dosing chamber.

Example 2: Amantadine Extended Release Coated Pellet Formulations

Amantadine HCl extended release coated pellet compositions suitable for nighttime administration were prepared using the components and relative amounts shown in Table 3 below and the manufacturing process described in Example 1.

TABLE 3

Composition of amantadine HCl ER capsules

| Component | Function | combined w/w of capsule |
| --- | --- | --- |
| Pellet Core | | |
| Amantadine Hydrochloride USP | Active | 45.15% |
| Microcrystalline cellulose spheres (Celphere ®) | Core seeds | 12.90% |
| Hydroxypropyl methyl cellulose USP | Binder/Coating polymer | 18.89% |
| Copovidone | Binder | 3.01% |
| Ethyl cellulose | Coating polymer | 13.53% |
| Povidone | Pore former | 1.84% |
| Medium chain triglycerides | Plasticizer | 1.62% |
| Talc USP | Anti-tack | 2.95% |
| Magnesium Stearate NF | Lubricant | 0.10% |
| Isopropyl alcohol | Solvent | —[1] |
| Water | Solvent | —[1] |

NF = National Formulary
[1]Purified water and isopropyl alcohol are removed during processing.

The desired weight of the ER coated pellets containing the unit dose was filled into empty #1 hard gelatin capsule shells (60, 140 mg strengths) using an encapsulator equipped with pellet dosing chamber. These dosage forms were used to provide the amantadine for the study described in Example 4 below according to the combinations in Table 4, as follows:

TABLE 4

| Dose for Study | 60 mg Capsules | 140 mg Capsules |
| --- | --- | --- |
| 260 mg | 2 | 1 |
| 340 mg | 1 | 2 |
| 420 mg | 0 | 3 |

Example 3: Pharmacokinetic Measurement of the Formulation of Amantadine ER Compared to IR Amantadine Objective: The primary objective of the study is to evaluate the pharmacokinetic profile, safety and tolerability of a prototype formulation of ER amantadine HCl (Formulation A), relative to a 100 mg film-coated IR amantadine HCl tablet (SYMMETREL®) given as single doses to healthy adult subjects under fasting conditions.

Study design: This is a Phase 1, randomized, single dose, open-label, two-period, two-treatment crossover, fasting pharmacokinetic study in which single 340 mg doses of formulation A of Amantadine ER capsules is compared to single 100 mg doses of marketed amantadine IR tablets (SYMMETREL®).

Methods: Subjects are admitted to the unit for the first period of dosing within 21 days of study screening. There will be a 7 day washout between dosing in period 1 and 2. In each dosing period subjects will be dosed on the day after checking into the unit and discharged 72 hours post dose. A final follow up end of study will be conducted within 14 days of dosing in the second period.

After an overnight fast, the formulation is administered to the subjects while in a sitting position with 240 mL of water. Blood samples were collected at 0 (pre-dose), 1, 2, 3, 4, 6, 7, 8, 9, 10, 11, 12, 13, 14, 15, 16, 18, 24, 30, 36, 48, 60, 72 hours following each dose. Plasma samples are assayed for amantadine by a validated liquid chromatography/tandem mass spectroscopy (LC/MS/MS) method. Pharmacokinetic parameters are calculated using a non-compartmental analysis with WinNonlin software (version 5.3 or higher; Pharsight Corporation).

An analysis of variance (ANOVA) is performed on the natural logarithms of Cmax and $AUC_{0\text{-}inf}$ determined from the data following a single dose of study drug using linear mixed effects model. The model will include sequence, period, and regimen as fixed effects and subject with sequence as random effect. Ratio of ER to IR for both AUC (relative bioavailability for ER formulation) and Cmax will be calculated. (Adverse events will be monitored throughout the study. Vital signs (pulse rate, blood pressure and body temperature), clinical laboratory measures (biochemistry, hematology, and urinalysis) and ECGs will be collected at various times during the study.

Expected Results: A total of 20 subjects comprising healthy male and female adults are expected to participate in the study.

The PK results from this study are expected to provide a reduced Cmax (on a dose proportionate basis) for the Amantadine ER relative to the IR form (about 1.1 to 1.7 ng/ml/mg amantadine for the ER form versus about 2.7 ng/ml/mg amantadine for the IR form). Also, the T max for the Amantadine ER is expected to be 9 to 18 hours vs about 4 hours for the IR form. Total amantadine exposure, as measured by $AUC_{0-inf}$ for the Amantadine ER formulation is expected to be 80 to 100 percent of SYMMETREL® on a dose adjusted basis.). FIG. 1 shows a plot of estimated amantadine plasma concentrations per mg amantadine dosed versus scheduled time for the ER formulation. The high and low curves bracket the range of mean values predicted at various times after dosing.

TABLE 5

Single Dose Pharmacokinetic Parameters of Three Formulations of Amantadine ER (Formulation A), as Compared to SYMMETREL ® (Formulation IR)

| Parameter[a] | Amantadine ER Formulation A | SYMMETREL Formulation IR |
|---|---|---|
| $C_{max}$ (ng/mL)/mg amantadine | 1.1 to 1.7 | 2.0 to 3.5 |
| $T_{max}$ (h) [range] | 12 to 18 | 2 to 6 |
| $AUC_{0-inf}$ (ng * h/mL)/mg amantadine | 46 to 56 | 54 to 65 |

Example 4: Steady State Plasma Amantadine Concentration (ng/mL) Following Once Daily Dosing of 260 mg, 340 mg and 420 mg Doses of ER Amantadine HCl (Formulation A)

Figure 2:
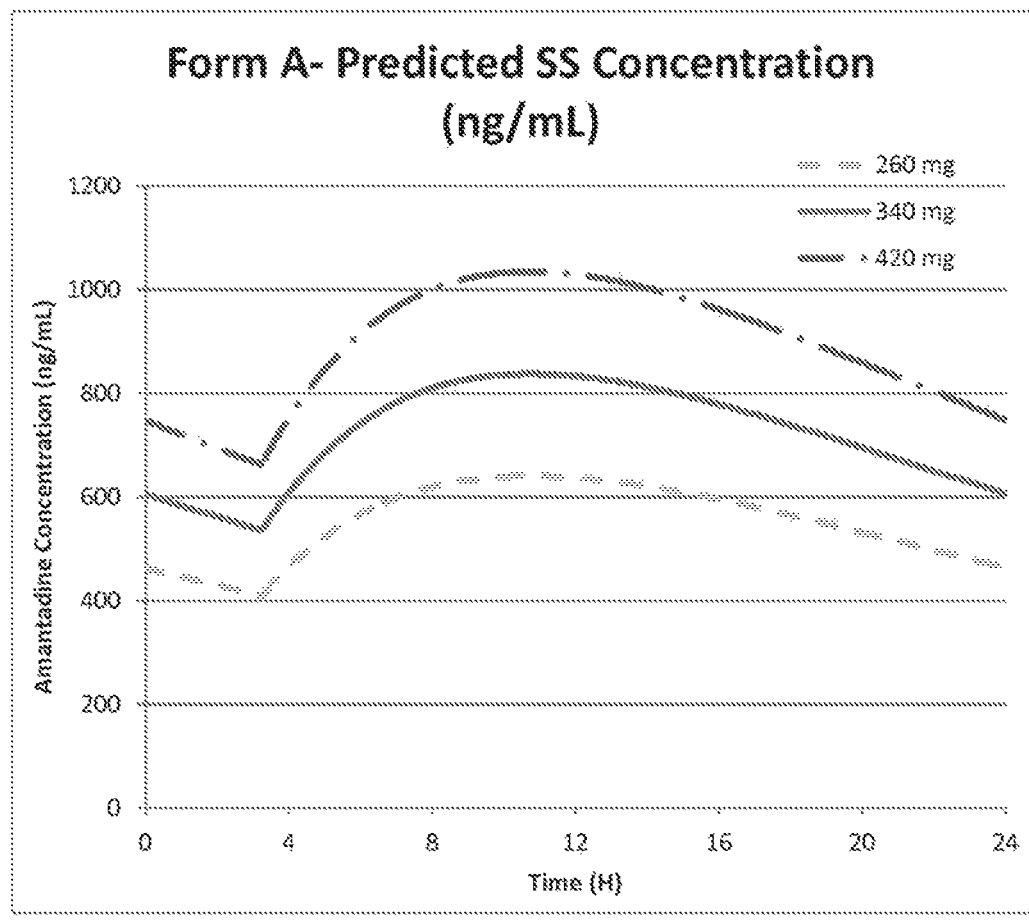
FIG. 2 shows the simulated mean plasma concentration of amantadine versus time curves following multiple dose administration of various strengths of amantadine ER administered once nightly. Shown is the steady state plasma amantadine concentration (ng/mL) predicted from single dose data following once daily dosing of 260 ng, 340 mg and 420 mg doses of ER Amantadine HCl (Formulation A).
Figure 3:
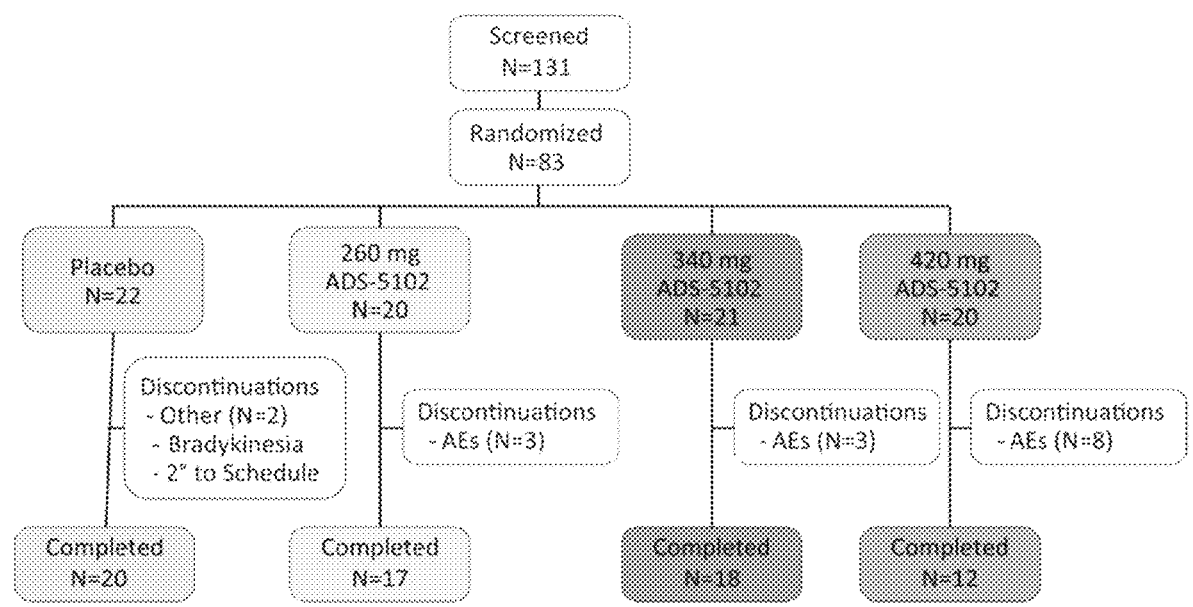
FIG. 3 shows the subject disposition for a randomized trial of extended release amantadine in Parkinson's disease patients with levodopa-induced dyskinesia.
Figure 4:
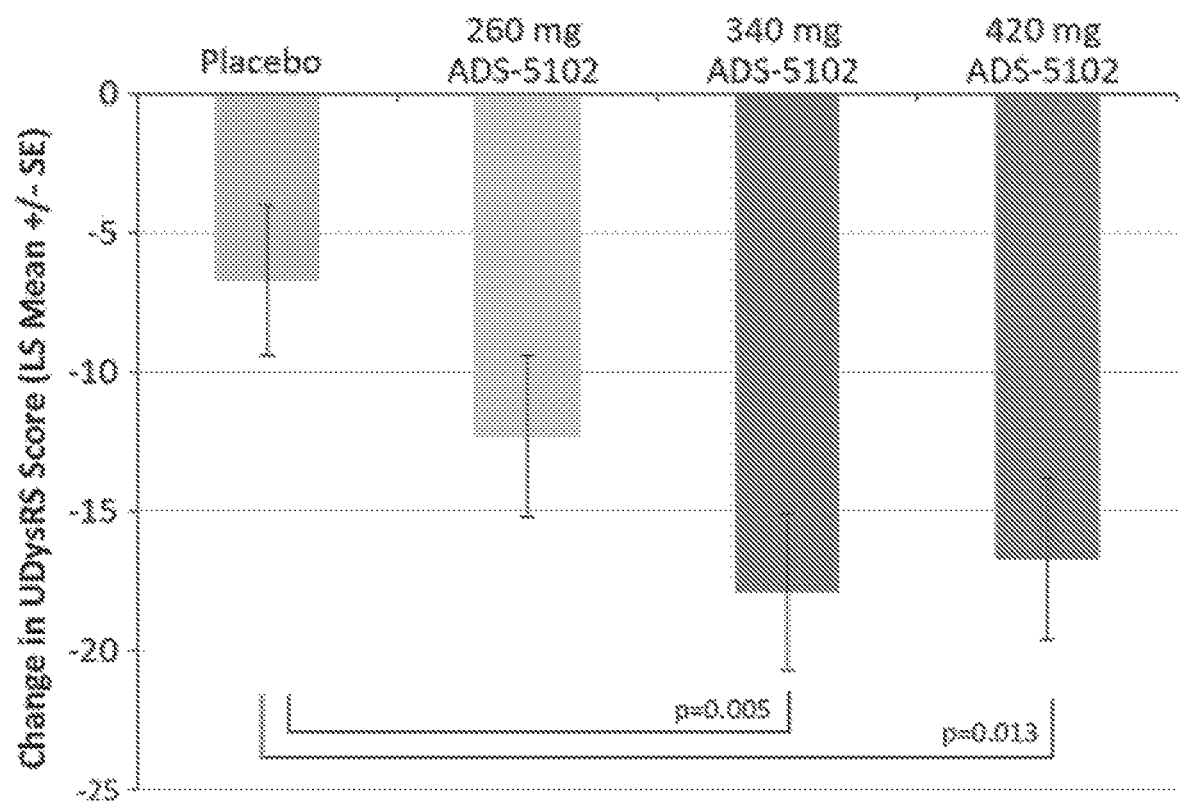
FIG. 4 shows change in UDysRS total score from baseline to week 8 of the randomized trial of extended release amantadine in Parkinson's disease patients with levodopa-induced dyskinesia.
Figure 5:
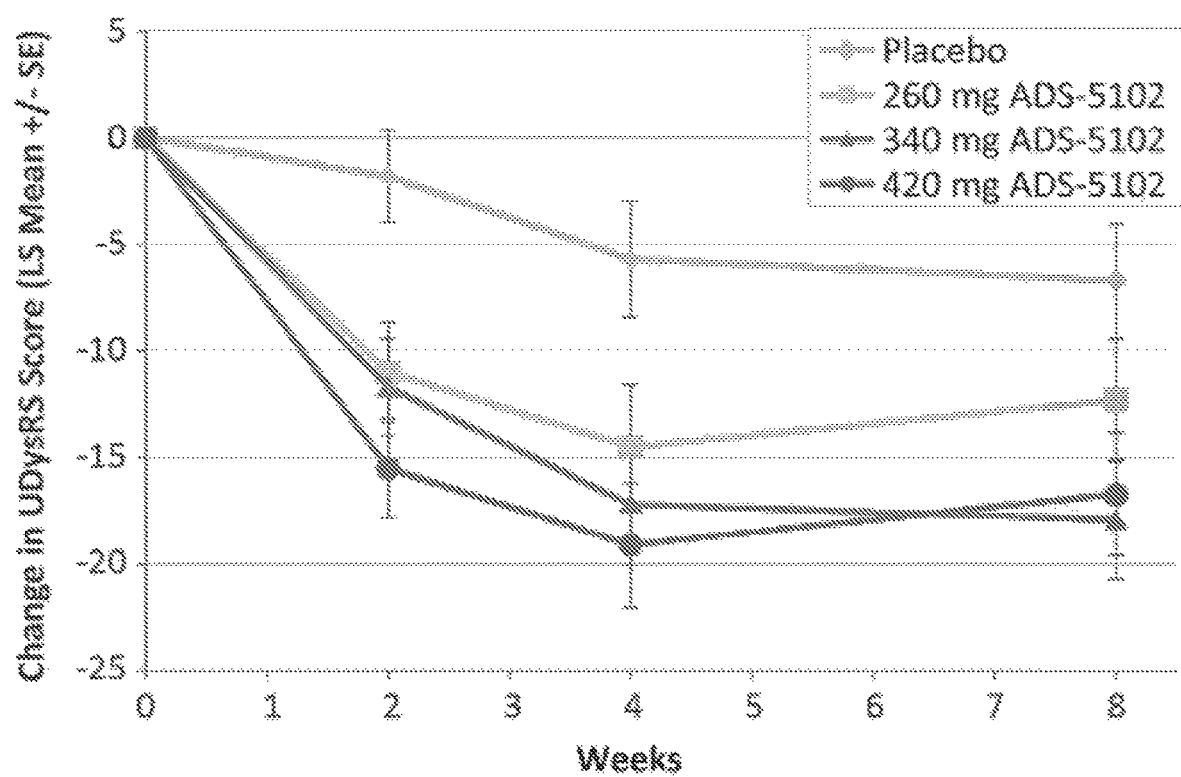
FIG. 5 shows the change in total UDysRS over time by treatment group in the randomized trial of extended release amantadine in Parkinson's disease patients with levodopa-induced dyskinesia.
Figure 6:
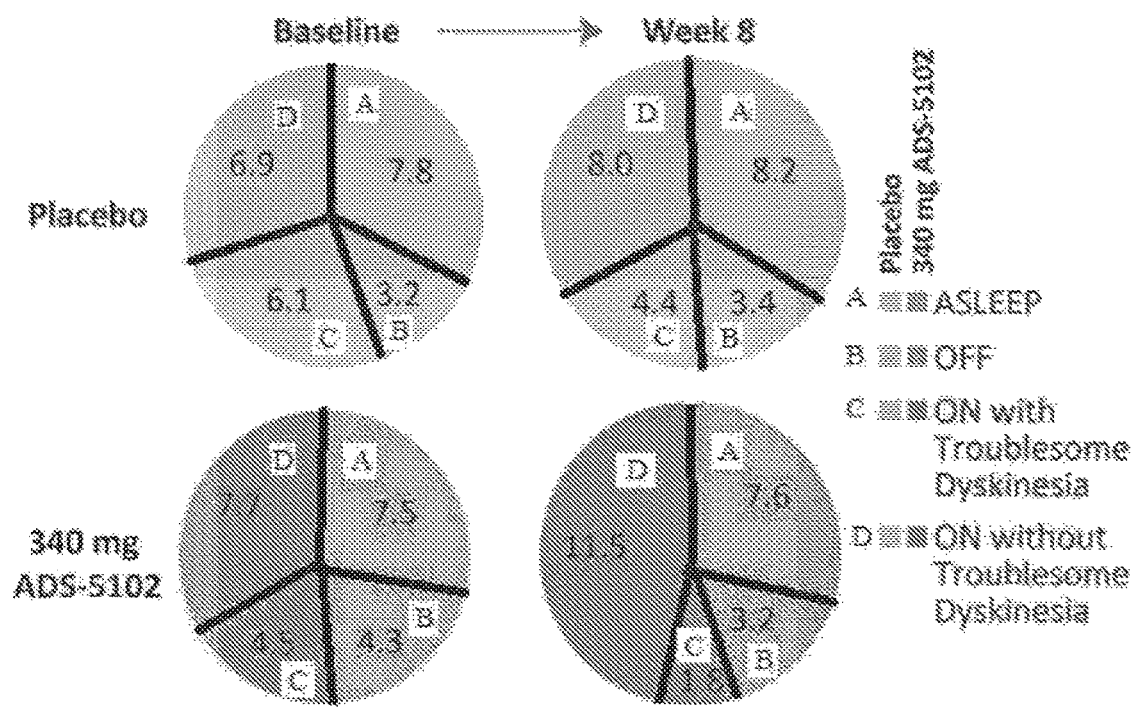
FIG. 6 shows 24-Hour PD Home Diary Parameters (Mean Hours) at Baseline and Week 8 (340 mg Formulation A and Placebo) in the randomized trial of extended release amantadine in Parkinson's disease patients with levodopa-induced dyskinesia.

The steady state plasma amantadine concentration were predicted for ER amantadine formulation A (260 mg, 340 mg and 420 mg) given once a day based on a model obtained using WINNONLIN from the observed data from a previous single dose study (Study 5103-C-101). The steady state predictions were done using the principles of superposition using the observed single dose data and linear kinetics was assumed to generate the profiles at various dose levels (260 mg, 340 mg and 420 mg). FIG. 2 shows the profiles for ER amantadine formulation A (260 mg, 340 mg and 420 mg) given once a day.

Example 5: A Randomized, Double-blind, Placebo-controlled Study of the Efficacy and Safety of Amantadine Extended Release Oral Capsules for the Treatment of Levodopa-induced Dyskinesia in Parkinson's Disease Study Objectives: This study was designed to evaluate the efficacy of three dose levels of Amantadine Extended Release (ER) oral capsules dosed once nightly at nighttime for the treatment of levodopa-induced dyskinesia (LID) in subjects with Parkinson's Disease (PD). In addition, the study was designed to demonstrate the safety and tolerability of Amantadine ER oral capsules dosed once nightly for the treatment of LID in subjects with PD. Study design: This was a multi-center, randomized, double-blind, placebo-controlled, 4-arm parallel group study of Amantadine ER in subjects with PD who have LID. Consenting subjects who met eligibility criteria were be randomized 1:1:1:1 to receive one of the following 4 treatments, each administered as once nightly, dosed at night:
Treatment A: Placebo,
Treatment B: 260 mg Amantadine ER (FORMULATION A),
Treatment C: 340 mg Amantadine ER (FORMULATION A)
Treatment D: 420 mg Amantadine ER (FORMULATION A)
Subjects who were randomized to Treatment C received, in double-blind fashion, 260 mg Amantadine ER once nightly during week 1, with an increase to 340 mg once nightly at the beginning of week 2. Subjects who were randomized to Treatment D, in double-blind fashion, 260 mg Amantadine ER once nightly during week 1, with an increase to 340 mg Amantadine ER once nightly during week 2, with a further increase to 420 mg once nightly at the beginning of week 3. Dosing for all groups continued at the nominal dose through week 8.

Following completion of the baseline visit and randomization, subjects returned to the clinic after 1, 2, 4, 6, and 8 weeks of dosing, with a follow-up visit 14 days following the last dose of study drug. Study visits and assessments were scheduled during the hours between 10 am through 4 pm. A set of two 24-hour diaries were be completed during 48 hours prior to randomization and 48 hours prior to selected study visits. The diary was used to score five different conditions in 30-minute intervals: Sleep, OFF, ON without dyskinesias, ON with nontroublesome dyskinesias, ON with troublesome dyskinesias.

Blood samples were collected at selected study visits for determination of amantadine plasma concentrations, and evaluation of steady-state population pharmacokinetics. Subject participation during the study was up to 12 weeks including a 2-week (maximum) screening period, 8-week (maximum) treatment period, and a 2-week follow-up period. Subjects unable to tolerate their assigned study drug assignment permanently discontinued study drug and continued to be followed for safety through 2 weeks following the last dose of study drug.

Patient Eligibility Criteria:
Subjects were eligible to take part in the study if they met the inclusion and did not meet the exclusion criteria. Selected key criteria were as follows:
Inclusion Criteria:
Male or female adults
Between 30 and 85 years of age, inclusive
Ambulatory or ambulatory-aided (e.g. walker or cane) ability while ON, such that the subject can could complete study assessments
Knowledgeable and reliable caregiver/study partner, if appropriate, to accompany the subject to study visits and assist in completion of study instruments, as needed and allowed
Signed a current IRB/IEC-approved informed consent form
Following diary training, the subject was willing and able to understand and complete the 24-hour home diary (caregiver/study partner assistance allowed)
Parkinson's Disease, complicated per UK Parkinson's Disease Society (UKPDS) Brain Bank Clinical Diagnostic Criteria
On a stable regimen of antiparkinson's medications, including levodopa, for at least 30 days prior to screening, with any levodopa administered not less than three times daily, and willing to continue the same doses and regimens during study participation
A score of at least 2 on part IV, item 4.2 (functional impact of dyskinesias) of the Unified Parkinson's Disease Rating Scale (MDS-UPDRS), at screening and at Day 1 (baseline)
Using the 48-hour PD home diaries completed just prior to Day 1 (baseline), at least 2 half-hour time periods between 10 am and 4 pm of each 24-hour period are indicated as "ON with troublesome dyskinesia"

Key Exclusion Criteria:
History of deep brain simulation; history of exclusively diphasic, off state, myoclonic or akathetic dyskinesia without peak dose dyskinesia
History of other neurological disease that, in the opinion of the investigator, would affect cognition or motor function, including, but not limited to Alzheimer's dementia, Huntington's disease, Lewy body dementia, frontotemporal dementia, corticobasal degeneration, progressive supranuclear palsy, multiple system atrophy, motor or sensory dysfunction secondary to stroke or brain trauma, or multi-infarct dementia with lacunae.
Presence of cognitive impairment, as evidenced by a Mini-mental State Examination (MMSE) score of less than 24 during screening.
Presence of an acute or chronic major psychiatric disorder (e.g., Major Depressive Disorder) or symptom (e.g., hallucinations, agitation, paranoia) that, in the opinion of the investigator, would affect the subject's ability to complete study assessments
History of sensory impairments (e.g., hearing, vision) that, in the opinion of the investigator, would impair the subject's ability to complete study assessments
History of alcohol or drug dependence or abuse within 2 years prior to screening
History of seizures within 2 years prior to screening
History of stroke or TIA within 2 years prior to screening
History of myocardial infarction, or NYHA Functional Classification of Heart Failure Class 3 or 4 within 2 years prior to screening
History of cancer within 5 years prior to screening, with the following exceptions: adequately treated non-melanomatous skin cancers, localized bladder cancer, non-metastatic prostate cancer or in situ cervical cancer
Any of the following laboratory test results at screening: Hemoglobin <10 g/dL, WBC <$3.0 \times 10^9$/L, Neutrophils <$1.5 \times 10^9$/L, Lymphocytes <$0.5 \times 10^9$/L, Platelets <$100 \times 10^9$/L, Hemoglobin A1C >9%, or Aspartate aminotransferase (AST) and/or alanine aminotransferase (ALT) >2 times the upper limit of normal
Estimated GFR <50 mL/min/1.73 $m^2$ by Modification of Diet in Renal Disease (MDRD) equation
Any clinically significant ECG abnormalities, including any findings of abnormal ventricular conduction of rhythm other than isolated PVCs or first degree AV block
Inability to swallow oral capsules, or a history of gastrointestinal malabsorption that would preclude the use of oral medication Study Endpoints:
The primary efficacy endpoint is the change from baseline to week 8 in the Unified Dyskinesia Rating Scale (UDysRS) total score. Key secondary endpoints include change from baseline to week 8:
Total Objective Score (III, IV) of the UDysRS
ON time without troublesome dyskinesia (ON without dyskinesia plus ON with non-troublesome dyskinesia), based on the PD home diary
ON time with troublesome dyskinesia, based on a standardized PD home diary
Total ON time with dyskinesia (non-troublesome and troublesome)
Total OFF time
Unified Parkinson's Disease Rating Scale (MDS-UPDRS), combined score (Parts I, II and III)
Unified Parkinson's Disease Rating Scale (MDS-UPDRS), part IV, items 4.1 (time spent with dyskinesias) and 4.2 (functional impact of dyskinesias)
Unified Parkinson's Disease Rating Scale (MDS-UPDRS), individual part scores (I, II, III, and IV)
Clinician's Global Impression of Change in overall PD symptoms, determined by a question completed by the investigator
Health-related Quality of Life as measured by a PD-specific HRQoL instrument, the PDQ-39
Fatigue as measured by the Fatigue Severity Scale (FSS). This scale includes 9 questions that are completed by the patient using a rating scale from 1 (strongly disagree) to 7 (strongly agree). Safety, including adverse events, safety-related study drug discontinuations, vital signs, and laboratory tests.

The following mixture of traditional and new scales have been selected for this study:
Unified Dyskinesia Rating Scale (UDysRS) was used for primary outcome measure. This scale has four parts, and a total possible score of 104:
I: Historical Disability (patient perceptions) of On-Dyskinesia impact
II: Historical Disability (patient perceptions) of Off-Dystonia impact
III: Objective Impairment (dyskinesia severity, anatomic distribution, and type, based on 4 observed activities)
IV: Objective Disability based on Part III activities
ON time without troublesome dyskinesia, based on a standardized Parkinson's disease home diary.
MDS-Unified Parkinson's Disease Rating Scale (MDS-UPDRS), part IV, items 4.1 (duration of dyskinesias: 0=none, 4=76-100% of the waking day) and 4.2 (disability of dyskinesias: 0=not disabling, 4=completely disabling) was a secondary outcome measure.

Statistical Methods
Efficacy Analyses: The efficacy analysis population included all randomized and dosed subjects who provided at least one post-baseline efficacy assessment, and met pre-specified entry criteria. Unless specified otherwise, all efficacy endpoints were analyzed using analysis of covariance (ANCOVA) models with the change from baseline to Week 8 as the dependent variable, treatment group as a factor, and the baseline value of the corresponding endpoint as a covariate. These models will be used for both pair-wise comparisons between each amantadine ER dose group versus placebo and for testing for a linear dose-response relationship. The dose-response test will be carried out using the scores 0, 260, 340, and 420 and additionally using equally spaced scores for the treatment groups. For the efficacy endpoint of UDysRS score, the primary analysis compared the 340 mg amantadine ER group to the placebo group using a two-sided test at the 5% level of significance.

The secondary endpoints were analyzed using the same types of ANCOVA models as described for the primary endpoint, except for CGIC which was a CMH analysis. All secondary comparisons between treatment groups were performed using two-sided tests at the 5% level of significance. A last observation carried forward (LOCF) approach was utilized for missing data. The primary efficacy analysis was repeated for the per-protocol population, a subset of the efficacy analysis population who provided week 8 efficacy assessments. The CGI was a CMH analysis.

Results: selected study results are shown in the table below.

| Instruments | Mean values and LS Mean changes (by Group) | | | | | Effect |
|---|---|---|---|---|---|---|
| | Placebo | 260 mg | 340 mg | 420 mg | | |
| Unified Dyskinesia Rating Scale (UDysRS) total score | 39.2<br>−6.7<br>— | 40.2<br>−12.3<br>−14% | 44.1<br>−17.9<br>−25% | 41.2<br>−16.7<br>−24% | Baseline<br>LS change<br>(Active − Placebo)/Baseline | Reduction in total UDysRS greater for the treatment groups than placebo |
| Unified Dyskinesia Rating Scale (UDysRS) objective total (parts III, IV) | 13.5<br>−1.9<br>— | 16.7<br>−4.4<br>−15% | 18.7<br>−7.1<br>−28% | 15.8<br>−8.3<br>−41% | Baseline<br>LS change<br>(A − P)/base | Reduction in UDysRS total Objective greater for the treatment groups than placebo |
| Unified Parkinson's Disease Rating Scale (UPDRS, MDS revision), Part IV | 11.7<br>−1.5<br>— | 10.6<br>−2.2<br>−6.6% | 11.8<br>−3.9<br>−20% | 10.5<br>−4.9<br>−32% | Baseline<br>LS change<br>(A − P)/base | Reduction in MDS-UPDRS Part IV greater for the treatment groups than placebo |
| ON time without troublesome dyskinesia (hours) | 6.9<br>0.9<br>— | 6.6<br>4.1<br>48% | 7.7<br>3.8<br>38% | 9.0<br>3.6<br>30% | Baseline<br>LS change<br>(A − P)/base | Increase in ON time without troublesome dyskinesia for the treatment groups versus placebo |
| ON time with dyskinesia (hours) | 10.2<br>−1.9<br>— | 10.0<br>−3.0<br>−11% | 8.0<br>−4.0<br>−26% | 10.4<br>−5.0<br>−30% | Baseline<br>LS change<br>(A − P)/base | Decrease in ON time with dyskinesia for the treatment groups versus placebo |
| ON time with troublesome dyskinesia (hours) | 6.1<br>−1.4<br>— | 6.3<br>−2.7<br>−21% | 4.5<br>−3.2<br>−40% | 5.1<br>−4.2<br>−55% | Baseline<br>LS change<br>(A − P)/base | Decrease in ON time with troublesome dyskinesia for the treatment groups versus placebo |
| OFF time (hours) | 3.2<br>0.3<br>— | 2.7<br>−1.0<br>−48% | 4.3<br>−0.6<br>−21% | 2.2<br>0.4<br>5% | Baseline<br>LS change<br>(A − P)/base | Decrease in OFF time for the 260 mg and 340 mg treatment groups versus placebo |

| | Mean value at week 8 | | | | | |
|---|---|---|---|---|---|---|
| | Placebo | 260 mg | 340 mg | 420 mg | | |
| CGIC** | 0.8<br>— | 1.4<br>75% | 1.9<br>138% | 1.3<br>62% | Mean<br>(A − P)/P** | Improvement in CGIC for all treatment groups versus placebo |

*Baseline is the mean value at the study baseline for the treatment group. LS mean change is the least squares change in the value at the 8 week time point for the treatment group. (A − P)/base equals (the LS mean change for the active group less the LS mean change for the placebo group) divided by the mean baseline value for the active group multiplied by 100%.
**The Clinician's Global Impression of Change (CGIC) is assessed on a 7 point scale (+3 "Marked Improvement" to −3 "Marked worsening") based on a response to the following question: "Considering your observations and impression of the subject's clinical status related to overall Parkinson's disease, including but not limited to Levodopa-induced Dyskinesias, how much has the subject changed between baseline and this visit?"

ON time without dyskinesia increased in all groups from baseline to 8 weeks, however the increase in ON time without dyskinesia for the treatment groups, including the 340 mg treatment group was larger than the increase for the placebo group.

The Clinician's Global Impression of Change in Overall PD symptoms is summarized in the table below. The results for the MITT population show a statistically significant improvement for the 340 mg treatment group, but not for the other groups.

| Visit: Day 57/Visit 8 Category | Placebo (N = 22) | 260 mg ADS-5102 (N = 19) | 340 mg ADS-5102 (N = 20) | 420 mg ADS-5102 (N = 19) |
|---|---|---|---|---|
| Marked Improvement | 1 (4.5) | 2 (10.5) | 7 (35.0) | 4 (21.1) |
| Moderate Improvement | 6 (27.3) | 8 (42.1) | 8 (40.0) | 6 (31.6) |
| Minimal Improvement | 4 (18.2) | 5 (26.3) | 1 (5.0) | 5 (26.3) |
| No Change | 10 (45.5) | 3 (15.8) | 4 (20.0) | 2 (10.5) |
| Minimal Worsening | 1 (4.5) | 1 (5.3) | 0 | 0 |
| Moderate Worsening | 0 | 0 | 0 | 2 (10.5) |
| Marked Worsening | 0 | 0 | 0 | 0 |
| P-value[1] | | 0.1042 | 0.0036 | 0.2158 |

[1]The p-value is from the Cochran-Mantel-Haenszel mean score test (using equally spaced scores).

The CGI-C results indicated that 75% of patients in the 340 mg dose group had a moderate to marked improvement in their clinical status (related to overall PD, including but not limited to LID) at week 8, versus 32% of placebo patients. Additional summaries of the analysis are provided in the figures.

Example 6: Amantadine Extended Release Compositions

Amantadine HCl extended release coated pellet compositions suitable for nighttime administration were prepared from the ER coated pellets prepared as described in Example 1 and filled into empty hard gelatin capsule shells as described in the table below.

TABLE 6

Amantadine HCl ER capsules

| Capsule Strength (mg Amantadine) | Capsule Size | ER Coated Pellets (mg) |
|---|---|---|
| 85 mg | 2 | 188.3 |
| 100 mg | 2 | 221.5 |
| 160 mg | 1 el | 354.4 |

TABLE 6-continued

Amantadine HCl ER capsules

| Capsule Strength (mg Amantadine) | Capsule Size | ER Coated Pellets (mg) |
|---|---|---|
| 170 mg | 0 | 376.5 |
| 200 mg | 0 el | 443.0 |

What is claimed is:

1. A method of reducing OFF time and increasing ON time without troublesome dyskinesia in a patient with Parkinson's disease (PD), wherein the patient is being treated with levodopa, the method comprising:
  (1) orally administering to said patient once daily for at least one week a first composition comprising 85 mg to 170 mg amantadine, or a pharmaceutically acceptable salt thereof, and at least one excipient that modifies the release of at least a portion of the amantadine or pharmaceutically acceptable salt thereof to provide an extended release form; and thereafter
  (2) orally administering to said patient once daily a second composition comprising about 260 mg to 380 mg amantadine, or a pharmaceutically acceptable salt thereof, and at least one excipient that modifies the release of at least a portion of the amantadine or pharmaceutically acceptable salt thereof to provide an extended release form;
  wherein OFF time is reduced and ON time without troublesome dyskinesia is increased after at least 7 weeks of administering the second composition once daily to the patient; and
  wherein the plasma concentration of amantadine in the patient is increased less than 10% at 1 hour after administration of the second composition.

2. The method of claim 1, wherein the reduction of OFF time and increase of ON time without troublesome dyskinesia is determined in a placebo controlled, double blind clinical study.

3. The method of claim 1, wherein the total daily amount of OFF time in the patient with Parkinson's disease is reduced 10% to 40% as determined using a PD Home Diary, relative to before administering the first composition.

4. The method of claim 1, wherein the total daily amount of ON time without troublesome dyskinesia is increased by at least double the amount that the OFF time is decreased.

5. The method of claim 1, wherein the total daily amount of ON time with dyskinesia is not increased.

6. The method of claim 1, wherein the total daily amount of ON time with troublesome dyskinesia is not increased.

7. The method of claim 4, wherein the total daily amount of OFF time in the patient with Parkinson's disease is reduced 10% to 40% as determined using a PD Home Diary, relative to before administering the first composition.

8. The method of claim 2, wherein the total daily amount of OFF time is reduced by 10% to 40% relative to placebo, as determined using a PD Home Diary.

9. The method of claim 1, wherein the total daily amount of ON time without troublesome dyskinesia is increased by 38% to 48% relative to placebo, as determined using a PD Home Diary.

10. The method of claim 1, wherein said second composition is administered 0 to 4 hours before bedtime.

11. The method of claim 1, wherein when said second composition is dosed in a single dose, fasted, human pharmacokinetic study, a C-ave-day is determined from 9 am to 4 pm, and a C-ave-night is determined from 11 pm to 7 am, the C-ave-day is 1.4 to 1.7 times the C-ave-night.

12. The method of claim 1, wherein administration of a single dose of said second composition to a cohort of human healthy volunteer subjects in a fasted state provides an average Cmax of 1.1 to 2.4 ng/ml per mg of amantadine or an $AUC_{0\text{-}inf}$ of 40 to 75 ng*h/mL per mg of amantadine.

13. The method of claim 1, wherein the once daily oral administration of a dose of said second composition to a cohort of human volunteers provides a steady state plasma concentration profile characterized by at least one of: (i) an average Cmax of 2.2 to 4.2 ng/ml per mg of amantadine, (ii) an average Cmin of 1.1 to 2.6 ng/ml per mg of amantadine, and (iii) an average $AUC_{0\text{-}24}$ of 46 to 73 ng*h/mL per mg of amantadine.

14. The method of claim 1, wherein said second composition comprises 260 mg to 305 mg amantadine.

15. The method of claim 1, wherein said second composition comprises 270 mg to 285 mg amantadine.

16. The method of claim 1, wherein said second composition comprises 300 mg to 380 mg of a pharmaceutically acceptable salt of amantadine.

17. The method of claim 16, wherein said second composition comprises 300 mg to 380 mg of amantadine hydrochloride.

18. The method of claim 17, wherein said second composition comprises 340 mg of amantadine hydrochloride.

19. The method of claim 1, wherein said first composition comprises 85 mg to 170 mg of a pharmaceutically acceptable salt of amantadine.

20. The method of claim 19, wherein said first composition comprises 170 mg of a pharmaceutically acceptable salt of amantadine.

21. The method of claim 20, wherein said first composition comprises 170 mg of amantadine hydrochloride.

22. The method of claim 17, wherein said first composition comprises 170 mg of amantadine hydrochloride.

23. The method of claim 16, wherein said first composition comprises 85 mg to 170 mg of a pharmaceutically acceptable salt of amantadine.

24. The method of claim 23, wherein said first composition comprises 170 mg of a pharmaceutically acceptable salt of amantadine.

25. The method of claim 20, wherein said second composition comprises 340 mg of a pharmaceutically acceptable salt of amantadine.

26. The method of claim 1, wherein said second composition comprises 2 unit dosage forms.

27. The method of claim 22, wherein said second composition comprises 2 unit dosage forms.

28. The method of claim 1, wherein said first composition comprises 2 unit dosage forms.

29. The method of claim 1, wherein administration of a single dose of said second composition to a cohort of human healthy volunteer subjects in a fasted state provides an average $T_{max}$ of 9 to 18 hours.

30. The method of claim 29, wherein the average $T_{max}$ is 12 to 18 hours.

31. The method of claim 12, wherein the average Cmax is 1.1 to 1.7 ng/ml per mg of amantadine.

32. The method of claim 12, wherein the average Cmax is 1.6 to 2.4 ng/ml per mg of amantadine.

33. The method of claim 12, wherein the average Cmax is 1.7 to 2.4 ng/ml per mg of amantadine.

34. The method of claim 12, wherein the average $AUC_{0\text{-}inf}$ is 46 to 56 ng*h/mL per mg of amantadine.

35. The method of claim 12, wherein the average $AUC_{0\text{-}inf}$ is 46 to 75 ng*h/mL per mg of amantadine.

36. The method of claim 12, wherein the average $AUC_{0\text{-}inf}$ is 40 to 56 ng*h/mL per mg of amantadine.

37. The method of claim 13, wherein the average Cmax is 2.2 to 2.7 ng/ml per mg of amantadine.

38. The method of claim 13, wherein the average Cmax is 2.4 to 4.2 ng/ml per mg of amantadine.

39. The method of claim 13, wherein the average Cmax is 2.4 to 2.7 ng/ml per mg of amantadine.

40. The method of claim 13, wherein the average Cmin is 1.4 to 1.7 ng/ml per mg of amantadine.

41. The method of claim 13, wherein the average Cmin is 1.4 to 2.6 ng/ml per mg of amantadine.

42. The method of claim 13, wherein the average Cmin is 1.1 to 1.7 ng/ml per mg of amantadine.

43. The method of claim 13, wherein the average $AUC_{0\text{-}24}$ is 46 to 56 ng*h/mL per mg of amantadine.

44. The method of claim 13, wherein the average $AUC_{0\text{-}24}$ is 48 to 73 ng*h/mL per mg of amantadine.

45. The method of claim 13, wherein the average $AUC_{0\text{-}24}$ is 48 to 56 ng*h/mL per mg of amantadine.

46. The method of claim 2, wherein the subjects administered placebo in the placebo controlled, double blind clinical study were administered placebo for at least 8 weeks.

47. The method of claim 1, wherein the second composition is characterized by a fractional AUC from 0 to 8 hours that is about 5 to 15% of $AUC_{0\text{-}inf}$ after administration of a single dose.

48. The method of claim 1, wherein the second composition is characterized by a fractional AUC from 0 to 4 hours that is less than 5% of $AUC_{0\text{-}inf}$ after administration of a single dose.

49. The method of claim 48, wherein the second composition is characterized by a fractional AUC from 0 to 4 hours that is less than 3% of $AUC_{0\text{-}inf}$ after administration of a single dose.

50. A method of reducing OFF time and increasing ON time without troublesome dyskinesia in a patient with Parkinson's disease (PD), wherein the patient is being treated with levodopa, the method comprising:
(1) orally administering to said patient once daily for at least one week a first composition comprising 260 mg amantadine hydrochloride and at least one excipient that modifies the release of at least a portion of the amantadine hydrochloride to provide an extended release form; and thereafter
(2) orally administering to said patient once daily a second composition comprising 290 mg to 325 mg amantadine hydrochloride and at least one excipient that modifies the release of at least a portion of the amantadine hydrochloride to provide an extended release form;
wherein OFF time is reduced and ON time without troublesome dyskinesia is increased after at least 7 weeks of administering the second composition once daily to the patient; and
wherein the plasma concentration of amantadine in the patient is increased less than 10% at 1 hour after administration of second composition.

51. The method of claim 50, wherein the total daily amount of OFF time in the patient with Parkinson's disease is reduced 10% to 40% as determined using a PD Home Diary, relative to before administering the first composition.

52. The method of claim 50, wherein the total daily amount of ON time without troublesome dyskinesia is increased between 3.8 and 4.1 hours, as determined using a PD Home Diary, relative to before administering the first composition.

53. The method of claim 50, wherein the total daily amount of ON time with dyskinesia is not increased.

54. The method of claim 50, wherein the total daily amount of ON time with troublesome dyskinesia is not increased.

55. The method of claim 50, wherein the second composition is characterized by a fractional AUC from 0 to 4 hours that is less than 5% of $AUC_{0\text{-}inf}$ after administration of a single dose.

56. The method of claim 1, wherein the first and second compositions are formulated as one or two capsules comprising amantadine, or a pharmaceutically acceptable salt thereof, and at least one excipient that modifies the release of at least a portion of the amantadine or pharmaceutically acceptable salt thereof to provide an extended release form.

57. The method of claim 56, wherein the first composition comprises one of the capsules and the second composition comprises two of the capsules.

58. The method of claim 57, wherein each capsule comprises the same formulation.

* * * * *